(12) United States Patent
Wang

(10) Patent No.: US 11,866,407 B2
(45) Date of Patent: Jan. 9, 2024

(54) COMPOSITIONS AND METHODS FOR INHIBITING $M^{pro}$ AND $PL^{pro}$ PROTEASE ACTIVITY AND FOR PREVENTING AND TREATING SARS-COV-2 INFECTION

(71) Applicant: Arizona Board of Regents on Behalf of the University of Arizona, Tucson, AZ (US)

(72) Inventor: Jun Wang, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 17/724,125

(22) Filed: Apr. 19, 2022

(65) Prior Publication Data
US 2022/0332683 A1 Oct. 20, 2022

Related U.S. Application Data

(60) Provisional application No. 63/177,227, filed on Apr. 20, 2021.

(51) Int. Cl.
| | | |
|---|---|---|
| C07D 207/273 | (2006.01) | |
| C07D 207/46 | (2006.01) | |
| A61K 31/16 | (2006.01) | |
| A61P 11/00 | (2006.01) | |
| A61K 9/00 | (2006.01) | |
| C07D 209/02 | (2006.01) | |
| A61P 31/14 | (2006.01) | |

(52) U.S. Cl.
CPC ........ *C07D 207/273* (2013.01); *A61K 9/0014* (2013.01); *A61K 9/0019* (2013.01); *A61K 9/0053* (2013.01); *A61K 31/16* (2013.01); *A61P 11/00* (2018.01); *A61P 31/14* (2018.01); *C07D 207/46* (2013.01); *C07D 209/02* (2013.01)

(58) Field of Classification Search
CPC ..................... A61K 31/5377; C07D 207/273
See application file for complete search history.

(56) References Cited

U.S. PATENT DOCUMENTS

2014/0243341 A1* 8/2014 Chang ................ A61K 31/5377
514/424

OTHER PUBLICATIONS

Sacco et al. CAS: 175:335375, 2020.*
Beigel, J. H.; et al. Remdesivir for the Treatment of Covid-19—Final Report. N Engl J Med 2020, 383 (19), 1813-1826.
Bertram, S.; et al., TMPRSS2 and TMPRSS4 facilitate trypsin-independent spread of influenza virus in Caco-2 cells. J Virol 2010, 84 (19), 10016-25.
Boras, B.; et al. Discovery of a Novel Inhibitor of Coronavirus 3CL Protease as a Clinical Candidate for the Potential Treatment of COVID-19. bioRxiv 2020, 2020.09.12.293498.
Consortium, W. H. O. S. T.; et al., Repurposed Antiviral Drugs for Covid-19—Interim WHO Solidarity Trial Results. N Engl J Med 2021, 384 (6), 497-511.
Cox, R. M.; Wolf, J. D.; Plemper, R. K., Therapeutically administered ribonucleoside analogue MK-4482/EIDD-2801 blocks SARS-CoV-2 transmission in ferrets. Nat Microbiol 2021, 6 (1), 11-18.
Dampalla, C. S.; et al. Post-infection treatment with a protease inhibitor increases survival of mice with a fatal SARS-CoV-2 infection. bioRxiv 2021, 2021.02.05.429937.
De Rosa, M. F.; et al. Role of multiple drug resistance protein 1 in neutral but not acidic glycosphingolipid biosynthesis. J Biol Chem 2004, 279 (9), 7867-76.
Emsley, P.; Cowtan, K., Coot: model-building tools for molecular graphics. Acta Crystallogr D 2004, 60, 2126-2132.
Freitas, B. T.; et al., Characterization and Noncovalent Inhibition of the Deubiquitinase and deISGylase Activity of SARS-CoV-2 Papain-Like Protease. ACS Infect Dis 2020, 6 (8), 2099-2109.
Froggatt, H. M.; et al. Development of a Fluorescence-Based, High-Throughput SARS-CoV-2 3CLpro Reporter Assay. J Virol 2020, 94 (22), e01265-20.
Fu, L.; et al., Both Boceprevir and GC376 efficaciously inhibit SARS-CoV-2 by targeting its main protease. Nat Commun 2020, 11 (1), 4417.
Hoffmann, M. et al., SARS-CoV-2 Cell Entry Depends on ACE2 and TMPRSS2 and Is Blocked by a Clinically Proven Protease Inhibitor. Cell 2020, 181 (2), 271-280 e8.
Hu, Y.; et al. Inhibitors II and XII, and GC-376 Have Broad-Spectrum Antiviral Activity against Coronaviruses. ACS Infect Dis 2021, 7 (3), 586-597.
Hu, Y.; et al., The in vitro antiviral activity of lactoferrin against common human coronaviruses and SARS-CoV-2 is mediated by targeting the heparan sulfate co-receptor. Emerg Microbes Infect 2021, 10, 317-330.

(Continued)

*Primary Examiner* — Rei Tsang Shiao
(74) *Attorney, Agent, or Firm* — Casimir Jones, S.C.; Robert A. Goetz

(57) ABSTRACT

This invention is in the field of medicinal chemistry and relates to a new class of small-molecules having a pyrrolidinone-acetamide (or similar) structure (e.g.,

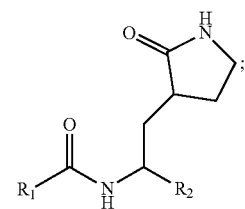

Formula I) which function as inhibitors of the SARS-CoV-2 papain-like protease ($PL^{pro}$), which function as inhibitors of the SARS-CoV-2 related viral 3CL protease ($MP^{pro}$), which function as therapeutics for the treatment of viral infection characterized with $PLP^{pro}$ and/or $M^{pro}$ protease activity and/or expression (e.g., COVID-19), and which function as therapeutics for the treatment of other conditions characterized with $PLP^{pro}$ and/or $M^{pro}$ protease activity and/or expression.

13 Claims, 13 Drawing Sheets
Specification includes a Sequence Listing.

(56) References Cited

OTHER PUBLICATIONS

Kim, Y.; et al., Reversal of the Progression of Fatal Coronavirus Infection in Cats by a Broad-Spectrum Coronavirus Protease Inhibitor. PLoS Pathog 2016, 12 (3), e1005531.

Klemm, T.; et al., Mechanism and inhibition of the papain-like protease, PLpro, of SARS-CoV-2. EMBO J 2020, 39 (18), e106275.

Kneller, D. W.; et al., Malleability of the SARS-CoV-2 3CL Mpro Active-Site Cavity Facilitates Binding of Clinical Antivirals. Structure 2020, 28 (12), 1313-1320.e3.

Li, X.; et al. Ethacridine inhibits SARS-CoV-2 by inactivating viral particles in cellular models. bioRxiv 2020, 2020.10.28.359042.

Ma, C.; Hu, Y.; Townsend, J. A.; Lagarias, P. I.; Marty, M. T.; Kolocouris, A.; Wang, J., Ebselen, Disulfiram, Carmofur, PX-12, Tideglusib, and Shikonin Are Nonspecific Promiscuous SARS-CoV-2 Main Protease Inhibitors. ACS Pharmacol Transl Sci 2020, 3 (6), 1265-1277.

Ma, C.; Sacco, M. D.; Hurst, B.; Townsend, J. A.; Hu, Y.; Szeto, T.; Zhang, X.; Tarbet, B.; Marty, M. T.; Chen, Y.; Wang, J., Boceprevir, GC-376, and calpain inhibitors II, XII inhibit SARS-CoV-2 viral replication by targeting the viral main protease. Cell Res 2020, 30 (8), 678-692.

Ma, C.; Wang, J., Dipyridamole, chloroquine, montelukast sodium, candesartan, oxytetracycline, and atazanavir are not SARS-CoV-2 main protease inhibitors. Proc Natl Acad Sci U S A 2021, 118 (8), e2024420118.

Morse, J. S.; Lalonde, T.; Xu, S.; Liu, W. R., Learning from the Past: Possible Urgent Prevention and Treatment Options for Severe Acute Respiratory Infections Caused by 2019-nCoV. Chembiochem 2020, 21 (5), 730-738.

Murshudov, G. N.; et al., REFMAC5 for the refinement of macromolecular crystal structures. Acta Crystallogr D 2011, 67, 355-367.

Naoya Kitamura; et al., An expedited approach towards the rationale design of non-covalent SARS-CoV-2 main protease inhibitors with in vitro antiviral activity bioRxiv 2021, 2020.12.19.423537.

Pedersen, N. C.; et al., Efficacy of a 3C-like protease inhibitor in treating various forms of acquired feline infectious peritonitis. J Feline Med Surg 2018, 20 (4), 378-392.

Petersen, E.; et. al., Comparing SARS-CoV-2 with SARS-CoV and influenza pandemics. Lancet Infect Dis 2020, 20 (9), e238-e244.

Qiao, J.; et al., SARS-CoV-2 M(pro) inhibitors with antiviral activity in a transgenic mouse model. Science 2021, 371, 1374-1378.

Rathnayake, A. D.; et al., 3C-like protease inhibitors block coronavirus replication in vitro and improve survival in MERS-CoV-infected mice. Sci Transl Med 2020, 12 (557), eabc5332.

Sacco, M. D.; et al., Structure and inhibition of the SARS-CoV-2 main protease reveal strategy for developing dual inhibitors against M(pro) and cathepsin L. Sci Adv 2020. 6 (50), eabe0751.

Sheahan, T. P.; et al. An orally bioavailable broad-spectrum antiviral inhibits SARS-CoV-2 in human ain/vay epithelial cell cultures and multiple coronaviruses in mice. Sci Transl Med 2020, 12 (541), eabb5883.

Shin, D.; et al., Papain-like protease regulates SARS-CoV-2 viral spread and innate immunity. Nature 2020, 587 (7835), 657-662.

Siklos, M.; BenAissa, M.; Thatcher, G. R. J., Cysteine proteases as therapeutic targets: does selectivity matter? A systematic review of calpain and cathepsin inhibitors. Acta Pharm Sin B 2015, 5 (6), 506-519.

Spinner, C. D.; et al. Investigators, f. t. G.-U.-.-. Effect of Remdesivir vs Standard Care on Clinical Status at 11 Days in Patients With Moderate COVID-19: A Randomized Clinical Trial. JAMA 2020, 324 (11), 1048-1057.

Stanifer, M. L.; et al., Critical Role of Type III Interferon in Controlling SARS-CoV-2 Infection in Human Intestinal Epithelial Cells. Cell Rep 2020, 32 (1), 107863.

Steuten, K.; et al. Challenges for Targeting SARS-CoV-2 Proteases as a Therapeutic Strategy for COVID-19. ACS Infect Dis Jun. 11, 2021;7(6):1457-1468.

Toots, M.; et al., Characterization of orally efficacious influenza drug with high resistance barrier in ferrets and human airway epithelia. Sci Transl Med 2019, 11 (515), eaax5866.

Vatansever, E. C.; et al., Bepridil is potent against SARS-CoV-2 in vitro. Proc Natl Acad Sci U S A 2021, 118 (10), e2012201118.

Vuong, W.; et al. Feline coronavirus drug inhibits the main protease of SARS-CoV-2 and blocks virus replication. Nat Commun 2020, 11 (1), 4282.

Zhang, L.; et al., alpha-Ketoamides as Broad-Spectrum Inhibitors of Coronavirus and Enterovirus Replication: Structure-Based Design, Synthesis, and Activity Assessment. J Med Chem 2020, 63 (9), 4562-4578.

\* cited by examiner

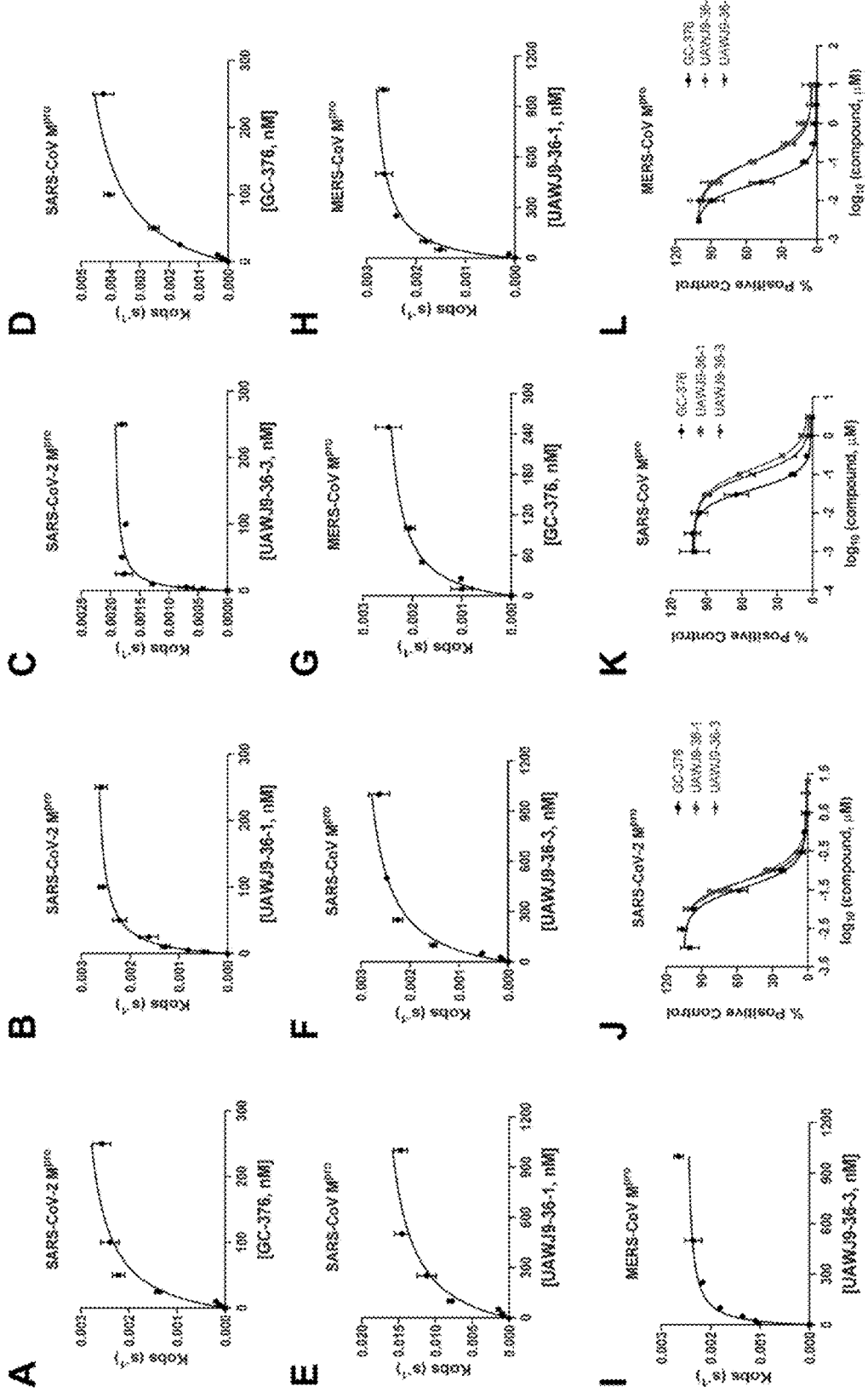
FIG. 4A-L

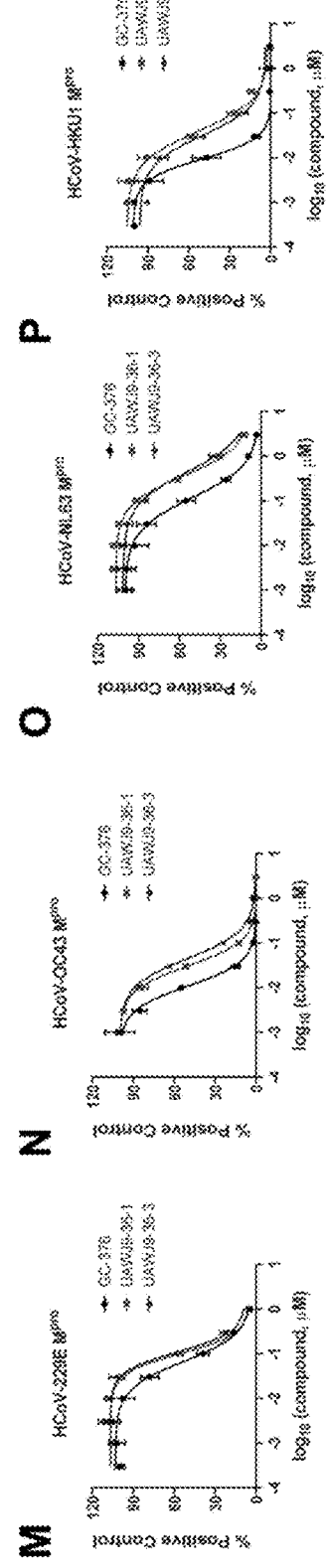
FIG. 4M-P

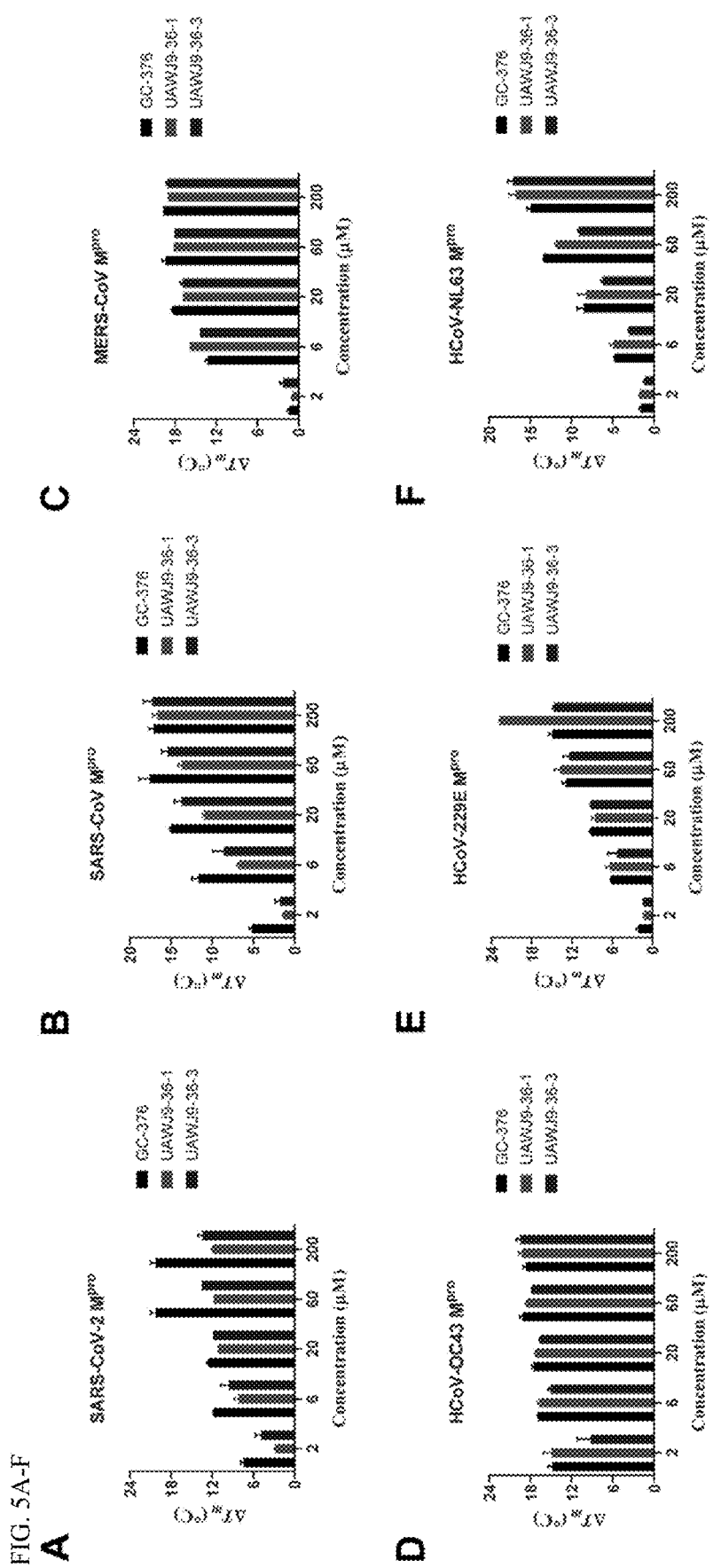
FIG. 5A-F

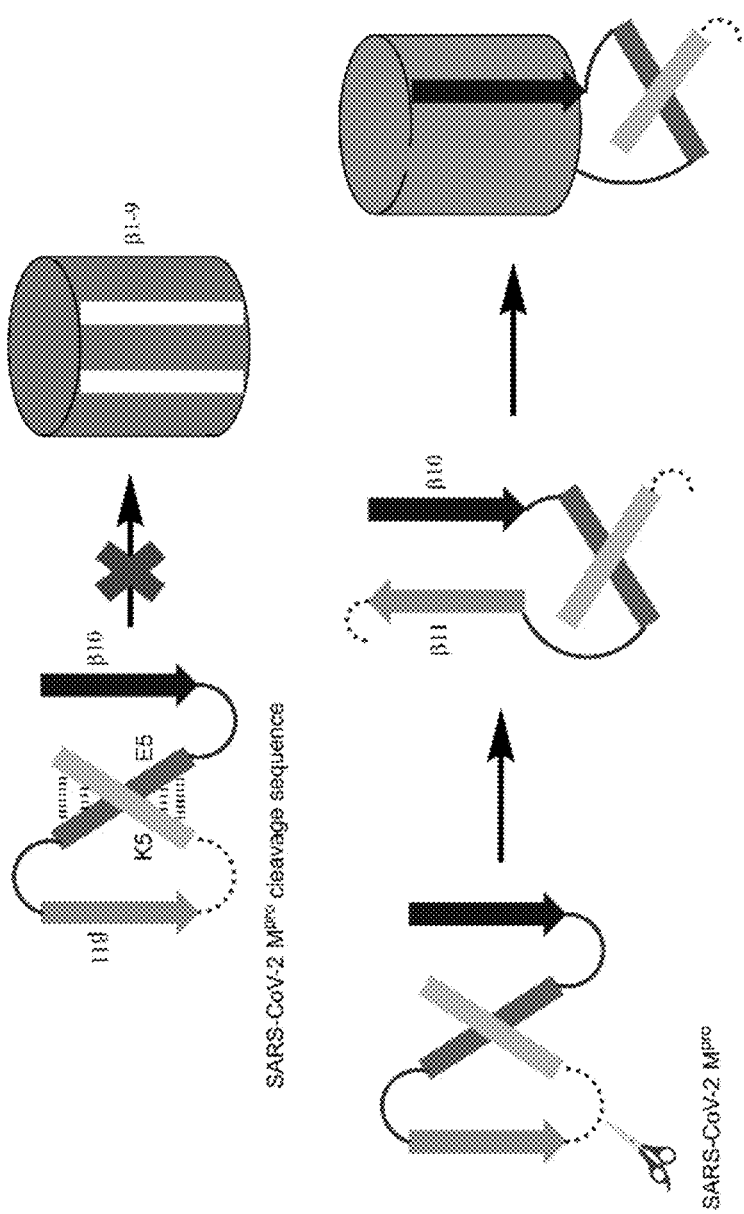
FIG. 6A-B

FIG. 6C-G
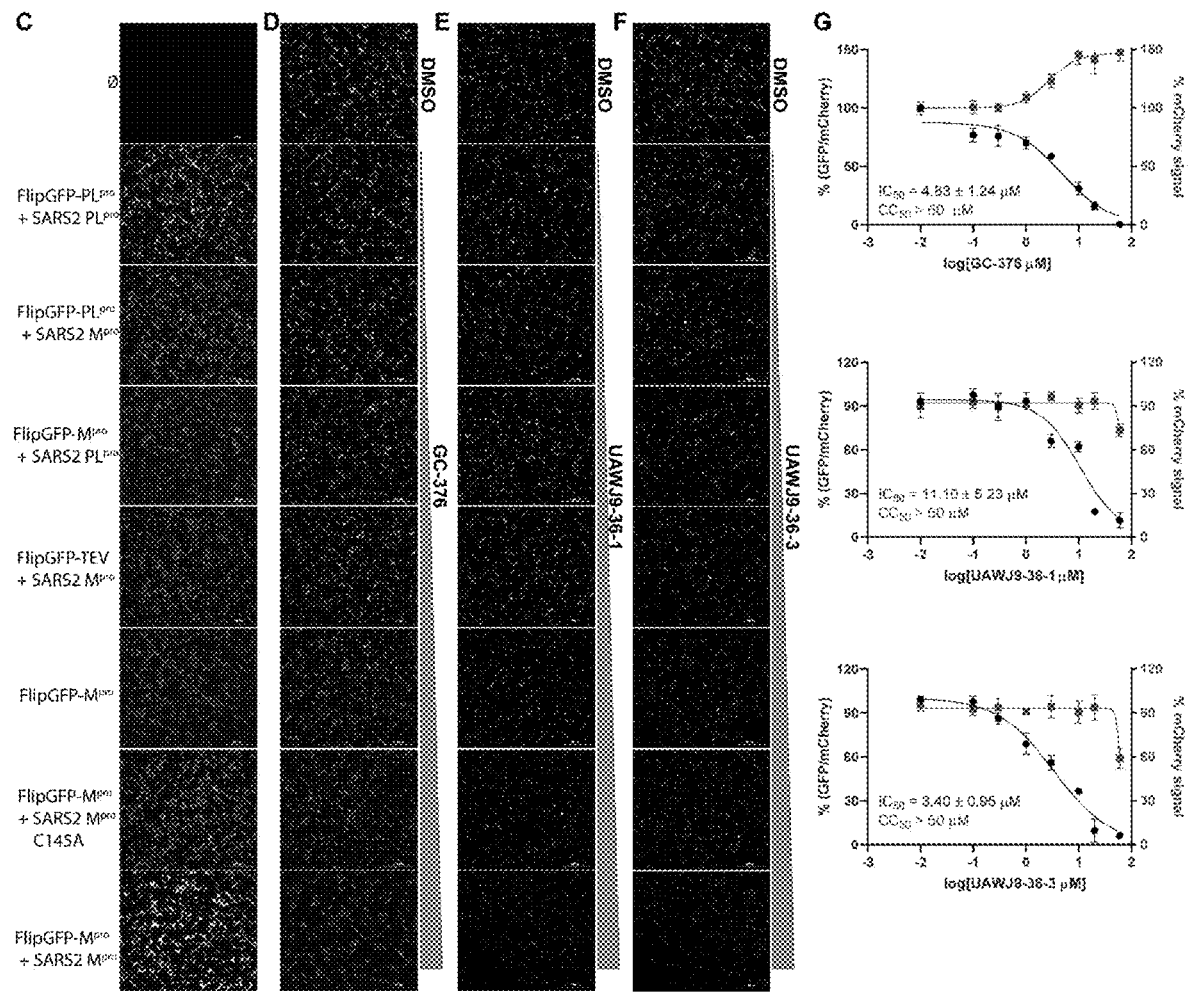

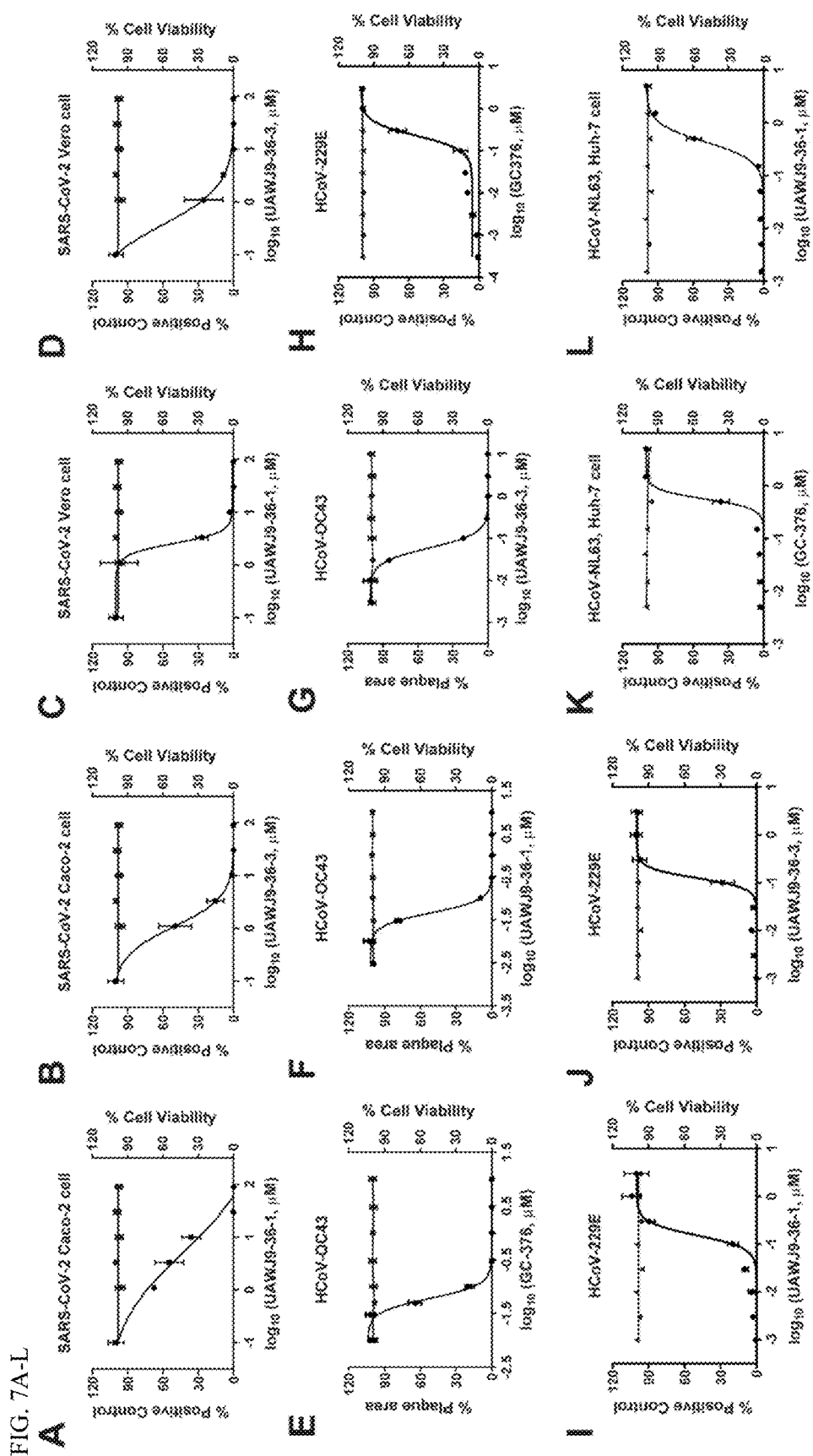
FIG. 7A-L

FIG. 7M-P
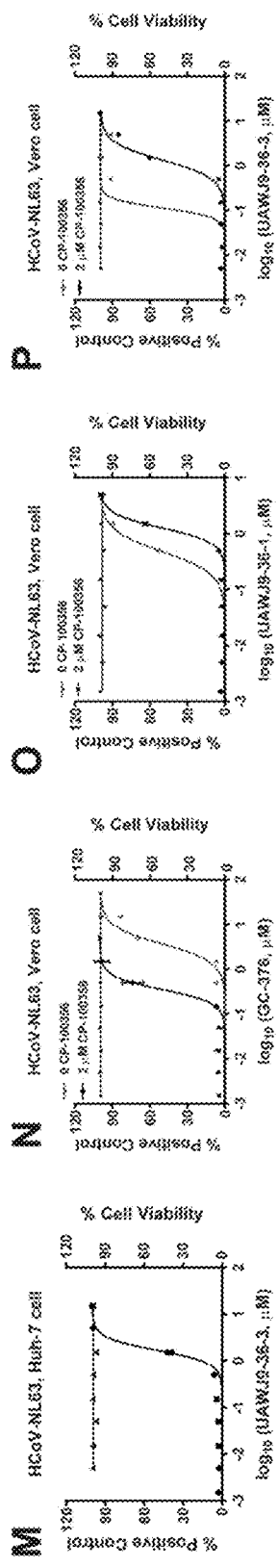

FIG. 8A-B
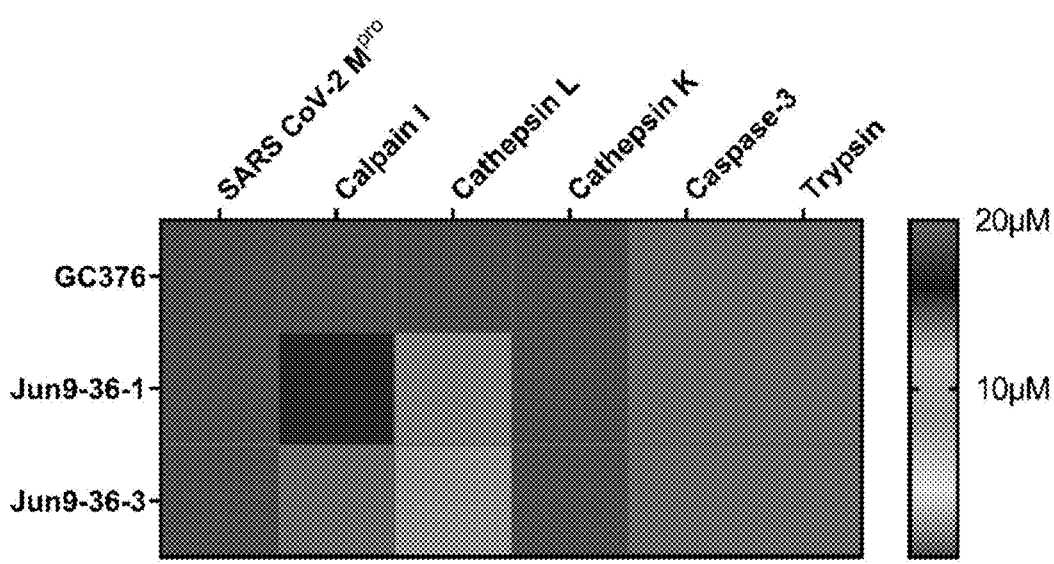

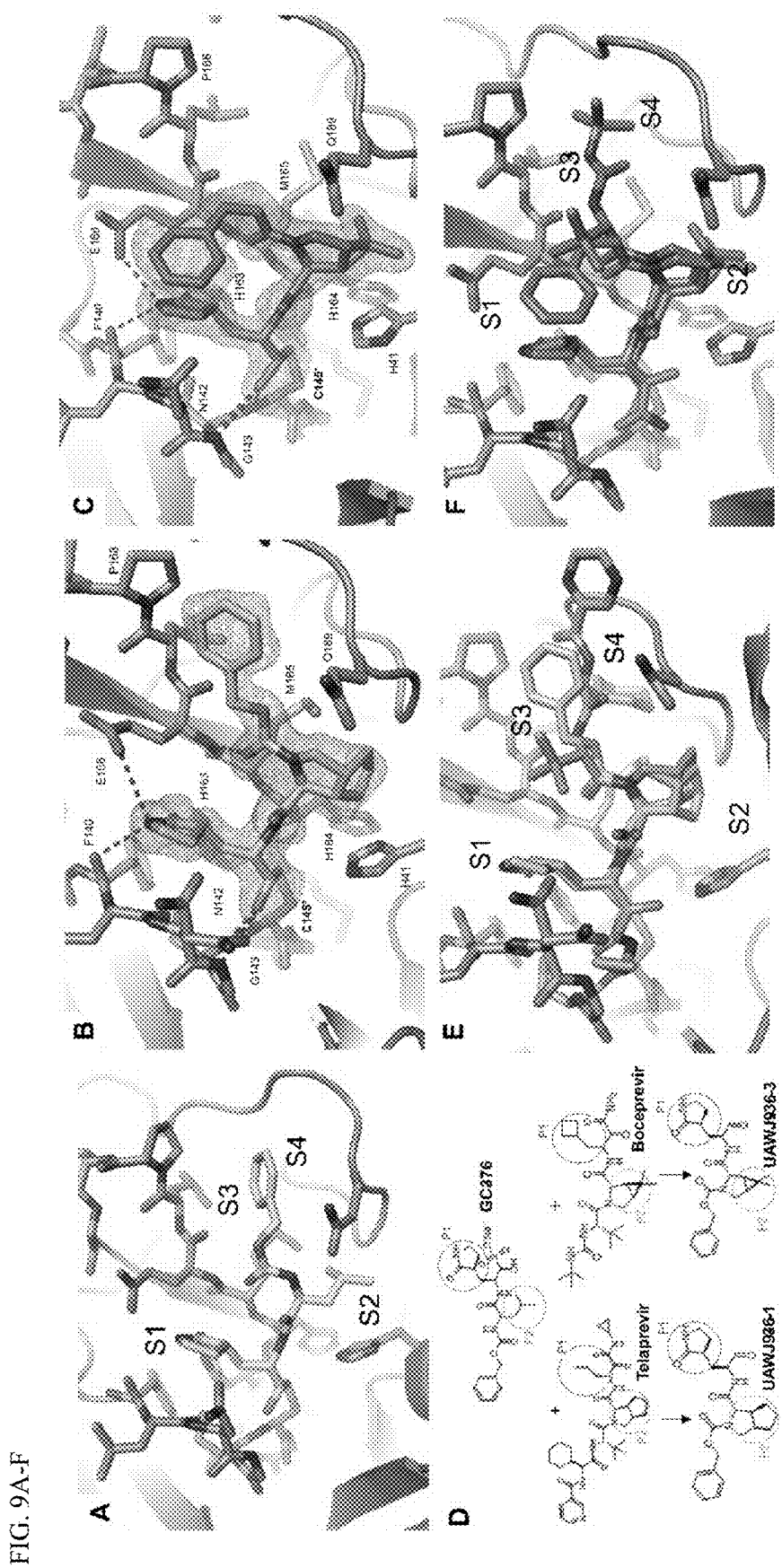
FIG. 9A-F

COMPOSITIONS AND METHODS FOR INHIBITING $M^{pro}$ AND $PL^{pro}$ PROTEASE ACTIVITY AND FOR PREVENTING AND TREATING SARS-COV-2 INFECTION

CROSS-REFERENCE TO RELATED APPLICATION

This application claims priority to and the benefit of U.S. Provisional Patent Application No. 63/177,227 filed Apr. 20, 2021, which is hereby incorporated by reference in its entirety.

STATEMENT REGARDING FEDERALLY SPONSORED RESEARCH OR DEVELOPMENT

This invention was made with government support under Grant Nos. R01 AI157046 and R01 AI147325 awarded by NIAID, NIH and DHHS. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 2,000 Byte ASCII (Text) file named "39482-202_ST25" created on Apr. 19, 2022.

FIELD OF THE INVENTION

This invention is in the field of medicinal chemistry and relates to a new class of small-molecules having a pyrrolidinone-acetamide (or similar) structure (e.g.,

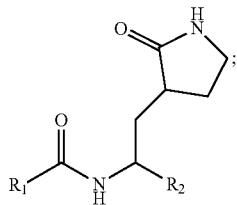

Formula I) which function as inhibitors of the SARS-CoV-2 papain-like protease ($PL^{pro}$), which function as inhibitors of the SARS-CoV-2 related viral 3CL protease ($MP^{pro}$), which function as therapeutics for the treatment of viral infection characterized with $PLP^{pro}$ and/or $MP^{pro}$ protease activity and/or expression (e.g., COVID-19), and which function as therapeutics for the treatment of other conditions characterized with $PLP^{pro}$ and/or $M^{pro}$ protease activity and/or expression.

INTRODUCTION

SARS-CoV-2 is the etiological agent of the COVID-19, and it is the third coronavirus that causes significant morbidity and mortality in humans. The other two highly pathogenic coronaviruses are SARS-CoV and MERS-CoV, with mortality rates of 9.7% and 34.3%,[1] respectively. In addition, four common human coronaviruses including HCoV-OC43, HCoV-229E, HCoV-NL63, and HCoV-HKU1 also circulate among humans and cause common colds. SARS-CoV-2 is a single-stranded, positive-sense RNA virus that shares ~80% sequence similarity with SARS-CoV. Although the previous SARS and MERS outbreaks failed to fuel the development of coronavirus antivirals, the current COVID-19 pandemic is a reminder that broad-spectrum antivirals are needed to combat not only existing coronaviruses, but also future emerging coronaviruses. In line with this, the viral polymerase and proteases are prominent targets for the development of broad-spectrum anti-coronavirus drugs.[2] The viral polymerase inhibitor remdesivir was the first drug that received FDA approval for the treatment of COVID-19 infection, although the results from several clinical trials were not consistent.[3-5] In addition, another viral polymerase inhibitor molnupiravir is currently in clinical trial.[6-7] Molnupiravir is an oral drug that was originally developed as an influenza drug.[8]

SARS-CoV-2 encodes two viral protease, the main protease ($MP^{pro}$) and the papain-like protease ($PL^{pro}$), both of which are validated antiviral drug targets.[9-10] $M^{pro}$ and $PL^{pro}$ are cysteine proteases that cleave the viral polyproteins during viral replication. $PL^{pro}$ plays additional roles in antagonizing host innate immune response through its deubiquitinating and deISG15ylating (interferon-induced gene 15) activities.[11-13] The active site residues of $M^{pro}$ across different members of coronaviruses are highly conserved, and $M^{pro}$ inhibitors have shown broad-spectrum antiviral activity. Among the $M^{pro}$ inhibitors reported to date, the most advanced ones are GC-376,[9-10] 6j 14 PF-07304814,[15] MI-09, MI-30[16], and the deuterated GC-376 (D2-GC376)[17] (FIG. 1A). GC-376 showed in vivo antiviral efficacy in treating cats infected with lethal feline infectious peritonitis virus.[18-19] A recent study found that GC-376 analog 6j protected mice from MERS-CoV infection.[14] The same group also reported that a deuterated analog of GC-376 (D2-GC-376, compound 2 in the original publication) had in vivo antiviral efficacy in SARS-CoV-2-infected mouse model.[17] PF-07304814 is an α-hydroxyl ketone prodrug that was originally being developed by Pfizer as an antiviral drug for SARS-CoV.[15] It has favorable pharmacokinetic properties and in vivo antiviral efficacy in SARS-CoV-infected mouse model. PF-07304814 is currently in phase I clinical trial for COVID-19.[15] Two additional GC-376 analogs MI-09 and MI-30 were recently reported to protect mice from lethal SARS-CoV-2 infection.[16] These promising results highlight the translational potential of $M^{pro}$ inhibitors as potent SARS-CoV-2 antivirals and validate $M^{pro}$ as an antiviral drug target for coronaviruses.

Improved pharmaceutical agents capable of inhibiting $M^{pro}$ protease activity and $PL^{pro}$ protease activity are desperately needed. Improved therapies for treating COVID-19 and conditions characterized with $PL^{pro}$ protease activity are desperately needed.

The present invention addresses these needs.

SUMMARY

Previous high-throughput screening identified GC-376 and boceprevir as SARS-CoV-2 $M^{pro}$ inhibitors with $IC_{50}$ values of 0.03 and 4.13 µM, respectively.[9] Telaprevir was less active and inhibited 31% of the $M^{pro}$ enzymatic activity at 20 µM. We subsequently solved the X-ray crystal structure of SARS-CoV-2 $M^{pro}$ with GC-376 and other hits including calpain inhibitors II and XII.[9-10] These results have been independently validated by others at about the same time. Fu et al reported that GC-376 and boceprevir inhibited SARS-CoV-2 $M^{pro}$ with $IC_{50}$ values of 0.15 and 8.0 µM, respectively,[20] and solved the X-ray crystal structure of SARS-CoV-2 $M^{pro}$ with boceprevir. Vuong et al showed that GC-376 and its active drug GC-373 inhibited SARS-CoV-2 $M^{pro}$ with $IC_{50}$ values of 0.40 and 0.19 μM, respectively.[21] Although telaprevir was reported as a weak inhibitor of SARS-CoV-2 $M^{pro}$ ($IC_{50}$>20 μM), Kneller et al showed that telaprevir inhibited SARS-CoV-2 $M^{pro}$ with an $IC_{50}$ of 18 μM and solved the X-ray co-crystal structure of SARS-CoV-2 $M^{pro}$ with telaprevir.[22]

Based on the available X-ray co-crystal structures, experiments conducted during the course of developing embodiments of the present invention aimed to further improve the enzymatic inhibition and cellular antiviral activity of SARS-CoV-2 $M^{pro}$ inhibitors by structure-based drug design. Specifically, the design was guided by overlaying different $M^{pro}$ inhibitors at the active site, and hybrid inhibitors were deigned to integrate optimal substitutions at each binding pocket. UAWJ9-36-1 was designed as a hybrid of GC-376 and telaprevir, and UAWJ9-36-3 was designed as a hybrid of GC-376 and boceprevir (FIG. 1B). Although UAWJ9-36-1 and UAWJ9-36-3 had similar enzymatic inhibition as GC-376 in the FRET assay, UAWJ9-36-3 had more potent enzymatic inhibition than GC-376 in the cell-based Flip-GFP $M^{pro}$ assay. The cellular antiviral activity with infectious SARS-CoV-2 further confirmed the superior potency of UAWJ9-36-3 compared to UAWJ9-36-1 and GC-376. The hybrid inhibitors UAWJ9-36-1 and UAWJ9-36-3 also inhibited the $M^{pro}$ from other known human coronaviruses including SARS-CoV, MERS-CoV, HCoV-OC43, HCoV-NL63, and HCoV-229E in the FRET-based enzymatic assay and the binding was confirmed in the thermal shift binding assay. The antiviral activity of UAWJ9-36-1 and UAWJ9-36-3 against HCoV-OC43 was tested in plaque assay, and against HCoV-NL63, and HCoV-229E in CPE assay. Selectivity profiling revealed that UAWJ9-36-1 and UAWJ9-36-3 had improved selectivity compared to GC-376 against host cysteine proteases calpain 1 and cathepsin L. Such experiments solved the X-ray co-crystal structures of SARS-CoV-2 $M^{pro}$ in complex with UAWJ9-36-1 and UAWJ9-36-3, which validate the design hypothesis. Overall, the designed hybrid inhibitors UAWJ9-36-1 and UAWJ9-36-3 represent promising drug candidates for further development as broad-spectrum coronavirus antivirals.

Accordingly, the present invention relates to a new class of small-molecules having a pyrrolidinone-acetamide (or similar) structure which function as inhibitors of the SARS-CoV-2 papain-like protease ($PL^{pro}$), which function as inhibitors of the SARS-CoV-2 related viral 3CL protease ($M^{pro}$), which function as therapeutics for the treatment of viral infection characterized with $PL^{pro}$ and/or $M^{pro}$ protease activity and/or expression (e.g., COVID-19), and which function as therapeutics for the treatment of other conditions characterized with $PL^{pro}$ and/or $M^{pro}$ protease activity and/or expression.

Certain pyrrolidinone-acetamide (or similar) compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

In a particular embodiment, compounds encompassed within Formula I are provided:

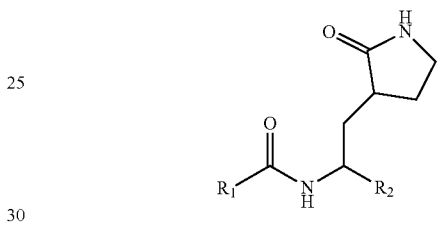

(Formula I), including pharmaceutically acceptable salts, solvates, and/or prodrugs thereof.

Formula I is not limited to a particular chemical moiety R1 and R2. In some embodiments, the particular chemical moiety for R1 and R2 independently include any chemical moiety that permits the resulting compound to inhibit $PL^{pro}$ protease activity. In some embodiments, the particular chemical moiety for R1 and R2 independently include any chemical moiety that permits the resulting compound to inhibit $M^{pro}$ protease activity. In some embodiments, the particular chemical moiety R1 and R2 independently include any chemical moiety that permits the resulting compound to prevent viral infection (e.g., COVID-19 infection).

Such embodiments are not limited to a particular definition for R1.

In some embodiments, R1 is selected from hydrogen,

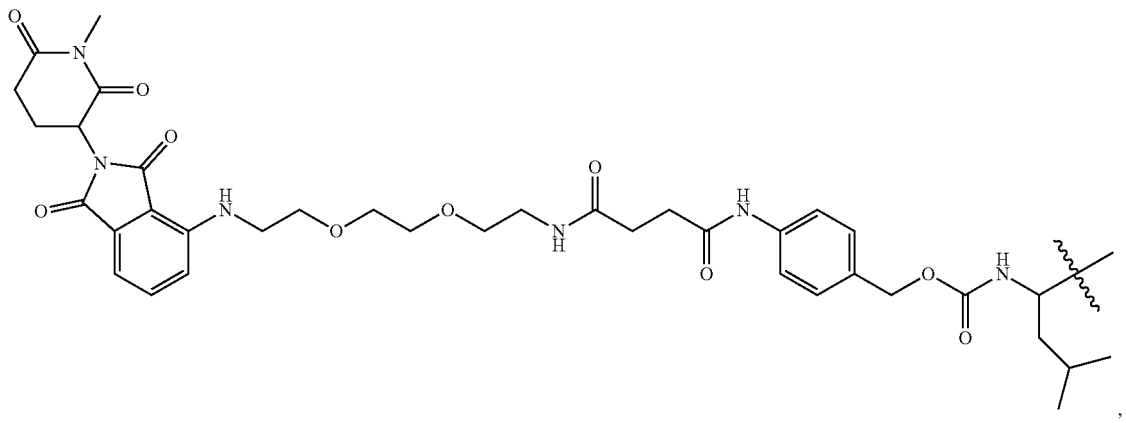

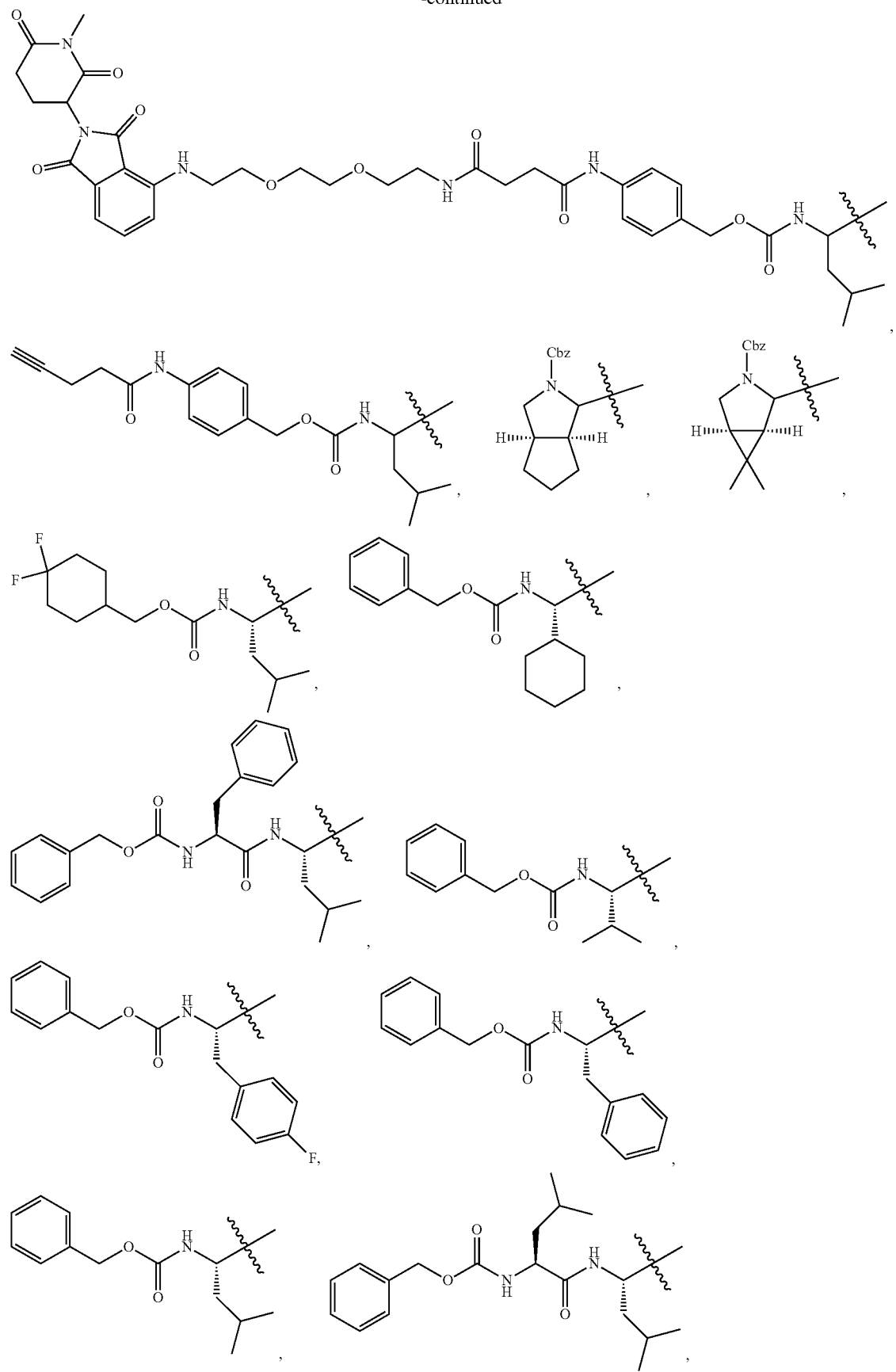

-continued

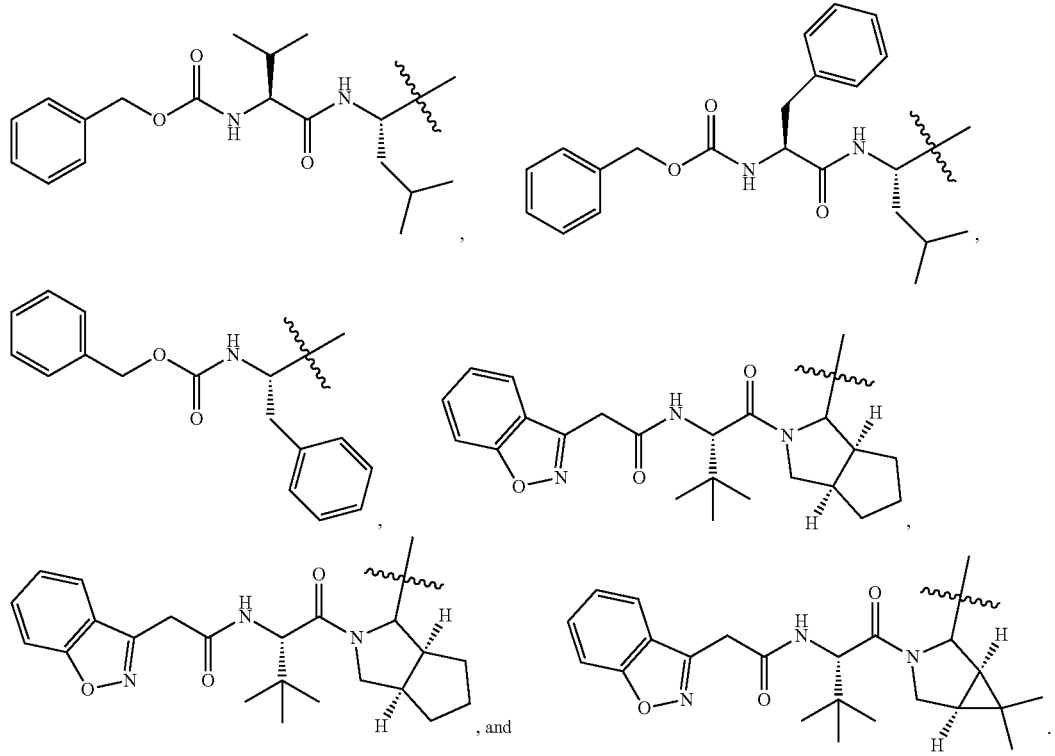

Such embodiments are not limited to a particular definition for R2.

In some embodiments, R2 is selected from hydrogen,

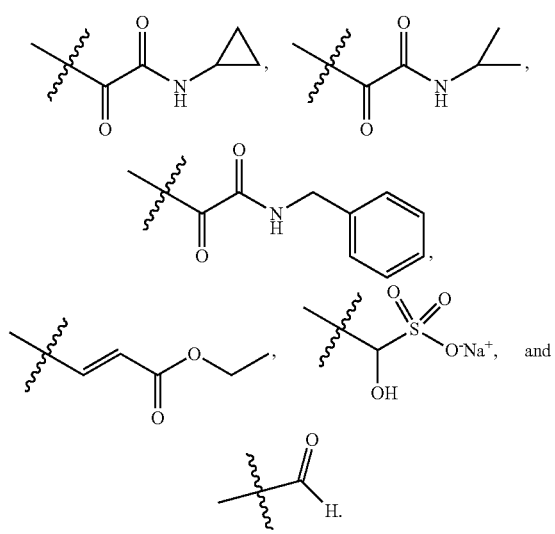

In some embodiments, the compound is recited in Table 1 (see, Example I).

The invention further provides processes for preparing any of the compounds of the present invention.

In certain embodiments, the present invention provides methods for administering a pharmaceutical composition comprising one or more compounds of the present invention to a subject (e.g., a human subject) (e.g., a human subject suffering from or at risk of suffering from a condition related to SARS-CoV-2 infection (e.g., COVID-19)) for purposes of treating, preventing and/or ameliorating the symptoms of a viral infection (e.g., SARS-CoV-2 infection (e.g., COVID-19)).

In such embodiments, the methods are not limited treating, preventing and/or ameliorating the symptoms of a particular type or kind of viral infection. In some embodiments, the viral infection is a SARS-CoV-2 related viral infection (e.g., COVID-19). In some embodiments, the viral infection is any infection related to influenza, HIV, HIV-1, HIV-2, drug-resistant HIV, Junin virus, Chikungunya virus, Yellow Fever virus, Dengue virus, Pichinde virus, Lassa virus, adenovirus, Measles virus, Punta Toro virus, Respiratory Syncytial virus, Rift Valley virus, RHDV, SARS coronavirus, Tacaribe virus, and West Nile virus. In some embodiments, the viral infection is associated with any virus having $PL^{pro}$ protease activity and/or expression. In some embodiments, the viral infection is associated with any virus having $M^{pro}$ protease activity and/or expression.

In such embodiments, administration of the pharmaceutical composition results in suppression of $PL^{pro}$ protease activity within the subject. In some embodiments, administration of the pharmaceutical composition results in suppression of any pathway related activity related to $PL^{pro}$ protease activity within the subject.

In such embodiments, administration of the pharmaceutical composition results in suppression of $M^{pro}$ protease activity within the subject. In some embodiments, administration of the pharmaceutical composition results in suppression of any pathway related activity related to $M^{pro}$ protease activity within the subject.

In some embodiments, the pharmaceutical composition comprising one or more compounds of the present invention is co-administered with one or more of hydroxychloroquine, dexamethasone, and remdesivir.

In certain embodiments, the present invention provides methods for treating, ameliorating and/or preventing a condition related to viral infection in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the viral infection is a SARS-CoV-2 viral infection.

In certain embodiments, the present invention provides methods for treating, ameliorating and/or preventing SARS-CoV-2 infection (e.g., COVID-19) in a subject, comprising administering to the subject a pharmaceutical composition comprising one or more compounds of the present invention. In some embodiments, the pharmaceutical composition comprising one or more compounds of the present invention is configured for oral administration. In some embodiments, the subject is a human subject.

In certain embodiments, the present invention provides methods for treating, ameliorating and/or preventing symptoms related to viral infection in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the subject is a human subject suffering from a SARS-CoV-2 viral infection. In some embodiments, the one or more symptoms related to viral infection includes, but is not limited to, fever, fatigue, dry cough, myalgias, dyspnea, acute respiratory distress syndrome, and pneumonia.

In certain embodiments, the present invention provides methods for treating, ameliorating and/or preventing symptoms related to SARS-CoV-2 infection (e.g., COVID-19) in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the one or more symptoms related to viral infection includes, but is not limited to, fever, fatigue, dry cough, myalgias, dyspnea, acute respiratory distress syndrome, and pneumonia.

In certain embodiments, the present invention provides methods for treating, ameliorating and/or preventing acute respiratory distress syndrome in a subject, comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the subject is a human subject suffering from a SARS-CoV-2 viral infection.

In certain embodiments, the present invention provides methods for treating, ameliorating and/or preventing acute respiratory distress syndrome related to SARS-CoV-2 infection (e.g., COVID-19) in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the subject is a human subject suffering from a SARS-CoV-2 viral infection.

In certain embodiments, the present invention provides methods for treating, ameliorating and/or preventing pneumonia in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the subject is a human subject suffering from a SARS-CoV-2 viral infection.

In certain embodiments, the present invention provides methods for treating, ameliorating and/or preventing pneumonia related to SARS-CoV-2 infection (e.g., COVID-19) in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the subject is a human subject suffering from a SARS-CoV-2 viral infection.

In some embodiments involving the treatment of acute respiratory distress syndrome and/or pneumonia, the pharmaceutical composition is administered in combination with a known agent to treat respiratory diseases. Known or standard agents or therapies that are used to treat respiratory diseases include, anti-asthma agent/therapies, anti-rhinitis agents/therapies, anti-sinusitis agents/therapies, anti-emphysema agents/therapies, anti-bronchitis agents/therapies or anti-chronic obstructive pulmonary disease agents/therapies. Anti-asthma agents/therapies include mast cell degranulation agents, leukotriene inhibitors, corticosteroids, beta-antagonists, IgE binding inhibitors, anti-CD23 antibody, tryptase inhibitors, and VIP agonists. Anti-allergic rhinitis agents/therapies include H1 antihistamines, alpha-adrenergic agents, and glucocorticoids. Anti-chronic sinusitis therapies include, but are not limited to surgery, corticosteroids, antibiotics, anti-fungal agents, salt-water nasal washes or sprays, anti-inflammatory agents, decongestants, guaifensesin, potassium iodide, luekotriene inhibitors, mast cell degranulating agents, topical moisterizing agents, hot air inhalation, mechanical breathing devices, enzymatic cleaners and antihistamine sprays. Anti-emphysema, anti-bronchitis or anti-chronic obstructive pulmonary disease agents/therapies include, but are not limited to oxygen, bronchodilator agents, mycolytic agents, steroids, antibiotics, anti-fungals, moisturization by nebulization, anti-tussives, respiratory stimulants, surgery and alpha 1 antitrypsin.

In certain embodiments, the present invention provides methods for inhibiting viral entry in a cell, comprising exposing the cell to a pharmaceutical composition comprising one or more compounds of the present invention. In some embodiments, the cell is at risk of viral infection (e.g., a cell at risk of SARS-CoV-2 infection). In some embodiments, the cell has been exposed to a virus (e.g., a cell currently exposed to SARS-CoV-2). In some embodiments, the cell is in culture. In some embodiments, the cell is a living cell in a subject (e.g., a human subject) (e.g., a human subject suffering from COVID-19) (e.g., a human subject at risk of suffering from COVID-19). In some embodiments, exposure of the cell to the pharmaceutical composition comprising one or more compounds of the present invention results in suppression of PL$^{pro}$ activity within the cell. In some embodiments, exposure of the cell to the pharmaceutical composition comprising one or more compounds of the present invention results in suppression of M$^{pro}$ activity within the cell.

In certain embodiments, the present invention provides kits comprising a pharmaceutical composition comprising one or more compounds of the present invention, and one or more of (1) a container, pack, or dispenser, (2) one or more additional agents selected from hydroxychloroquine, dexamethasone, and remdesivir, and (3) instructions for administration.

BRIEF DESCRIPTION OF THE DRAWINGS

FIGS. 4A-P: Enzymatic inhibition of GC-376, UAWJ9-36-1 and UAWJ9-36-3 against M$^{pro}$s from all seven human coronaviruses. Data fittings of the proteolytic reaction progression curves in the kinetic studies of SARS-CoV-2 M$^{pro}$ in the presence or absence of GC-376 (A); UAWJ9-36-1 (B); UAWJ9-36-3 (C); SARS-CoV M$^{pro}$ in the presence or absence of GC-376 (D); UAWJ9-36-1 (E); UAWJ9-36-3 (F); MERS-CoV M$^{pro}$ in the presence or absence of GC-376 (G); UAWJ9-36-1 (H); UAWJ9-36-3 (I) and dose response curves of GC-376, UAWJ9-36-1 and UAWJ9-36-3 against M$^{pro}$ from SARS-CoV-2 (J), SARS-CoV (K), MERS-CoV (L), HCoV-229E (M), HCoV-OC43 (N), HCoV-NL63 (O), and HCoV-HKU1 (P). The ratio of $k_2$ (second rate constant) over $K_I$ (equilibrium dissociation constant) from kinetic studies and IC$_{50}$ values from the dose response curves are listed in the table at the bottom. Data are mean±standard deviation of three replicates.

FIGS. 5A-G: Melting temperature shift ($\Delta T_m$) of M$^{pro}$s from all seven human coronaviruses in the presence of indicated concentrations of GC-376, UAWJ9-36-1 and UAWJ9-36-3. SARS-CoV-2 (A), SARS-CoV (B), MERS-CoV (C), HCoV-OC43 (D), HCoV-229E (E), HCoV-NL63 (F), HCoV-HKU1 (G). $\Delta T_m$ values of MP$^{pro}$s in the presence of 6 µM GC-376, UAWJ9-36-1 and UAWJ9-36-3 are listed in the table at the bottom. Data are mean±standard deviation of two replicates.

FIGS. 6A-G: Cellular protease inhibitory activity of UAWJ9-36-1 and UAWJ9-36-3 in the Flip-GFP M$^{pro}$ assay. (A) Principle of Flip-GFP assay; (B) Sequence of the flipped GFP β10-11 and construct of the Flip-GFP M$^{pro}$ plasmid; the corresponding SARS-CoV-2 M$^{pro}$ cleavage site between nsp4 and nsp5 was introduced into the plasmid, the arrow indicates the SARS-CoV-2 M$^{pro}$ cleavage site; (C) FlipGFP-M$^{pro}$ assay development. 293T cells were transfected with no plasmid (Ø); FlipGFP-PL$^{pro}$ and SARS-CoV-2 PL$^{pro}$ plasmids; FlipGFP-PL$^{pro}$ and SARS-CoV-2 M$^{pro}$ plasmids; FlipGFP-M$^{pro}$ and SARS-CoV-2 PL$^{pro}$ plasmids; FlipGFP-TEV and SARS-CoV-2 M$^{pro}$ plasmids; FlipGFP-M$^{pro}$ plasmid alone; FlipGFP-M$^{pro}$ and SARS-CoV-2 M$^{pro}$-C145A plasmids; and FlipGFP-M$^{pro}$ and SARS-CoV-2 M$^{pro}$ plasmids (details were described in the method sections). (D-F) Representative images of FlipGFP-M$^{pro}$ assay showed does-dependent decrease of GFP signal with the increasing concentration of compounds GC-376 (D), UAWJ9-36-1 (E), and UAWJ9-36-3 (F). (G) Dose-response curve plot of the inhibition of GFP signal over mCherry signal by compounds GC-376, UAWJ9-36-1 and UAWJ9-36-3; mCherry signal alone was used to calculate cytotoxicity.

FIGS. 7A-P: Antiviral activity of GC-376, UAWJ9-36-1, and UAWJ9-36-3 against SARS-CoV-2 and multiple HCoVs in cell culture. The antiviral activity of UAWJ9-36-1 (A, C), UAWJ9-36-3 (B, D) against SARS-CoV-2 in immunofluorescence assay was carried out in Vero E6 or Caco2-ACE2 cells. The antiviral activity of GC-376 (E, H), UAWJ9-36-1 (F, I), UAWJ9-36-3 (G, J) against HCoV-OC43 and HCoV-229E was performed in plaque assay and in CPE assay, respectively. The antiviral activity of GC-376 (K, N), UAWJ9-36-1 (L, O), UAWJ9-36-3 (M, P) against HCoV-NL63 in CPE assay was performed in Huh-7 cells or Vero cells in the presence or absence of P-glycoprotein inhibitor CP-100356. EC$_{50}$ values of GC-376, UAWJ9-36-1 and UAWJ9-36-3 against the coronaviruses tested in different types of cells and under different conditions are listed in the table at the bottom. EC$_{50}$ curve fittings were obtained using log (concentration of inhibitors) vs percentage of positive control with variable slopes in prism 8. The cellular cytotoxicity test was performed in each cell line used in the antiviral assays and the resulting curves were shown in blue. All data are mean±standard deviation of three replicates.

FIGS. 8A-B: Selectivity of UAWJ9-36-1 and UAWJ9-36-3 against host cysteine and serine proteases. (A) IC$_{50}$ values of UAWJ9-36-1 and UAWJ9-36-3 against host cysteine and serine proteases. Data=mean±standard error of two replications. $^a$data from reference[33], $^b$Pan-caspase inhibitor Z-VAD-FMK was included as a positive control and IC$_{50}$ was 0.10±0.04 µM). (B) Selectivity heat map.

FIGS. 9A-F: X-ray crystal structure of SARS-CoV-2 M$^{pro}$ with hybrid inhibitors UAWJ9-36-1 and UAWJ9-36-3. (A) X-ray crystal structure of SARS-CoV-2 M$^{pro}$ with GC-376 (PDB: 6WTT). (B) UAWJ-9-36-1 (PDB: 7LYH) and (C) UAWJ-9-36-3 (PDB ID: 7LYI) were both solved at 1.9 Å resolution. Unbiased Fo-Fc electron density map, shown in gray, is contoured at 2σ. (D) Design strategy for UAWJ-9-36-1 and UAWJ9-36-3. (E) Superimposed binding pose of telaprevir (violet) in SARS-CoV-2 M$^{pro}$ (PDB: 6XQS) with UAWJ-9-36-1 (cyan). (F) Superimposed binding pose of boceprevir in SARS-CoV-2 M$^{pro}$ (blue) (PDB: 6XQU) with UAWJ-9-36-3 (magenta).

DETAILED DESCRIPTION OF THE INVENTION

Figure 1:
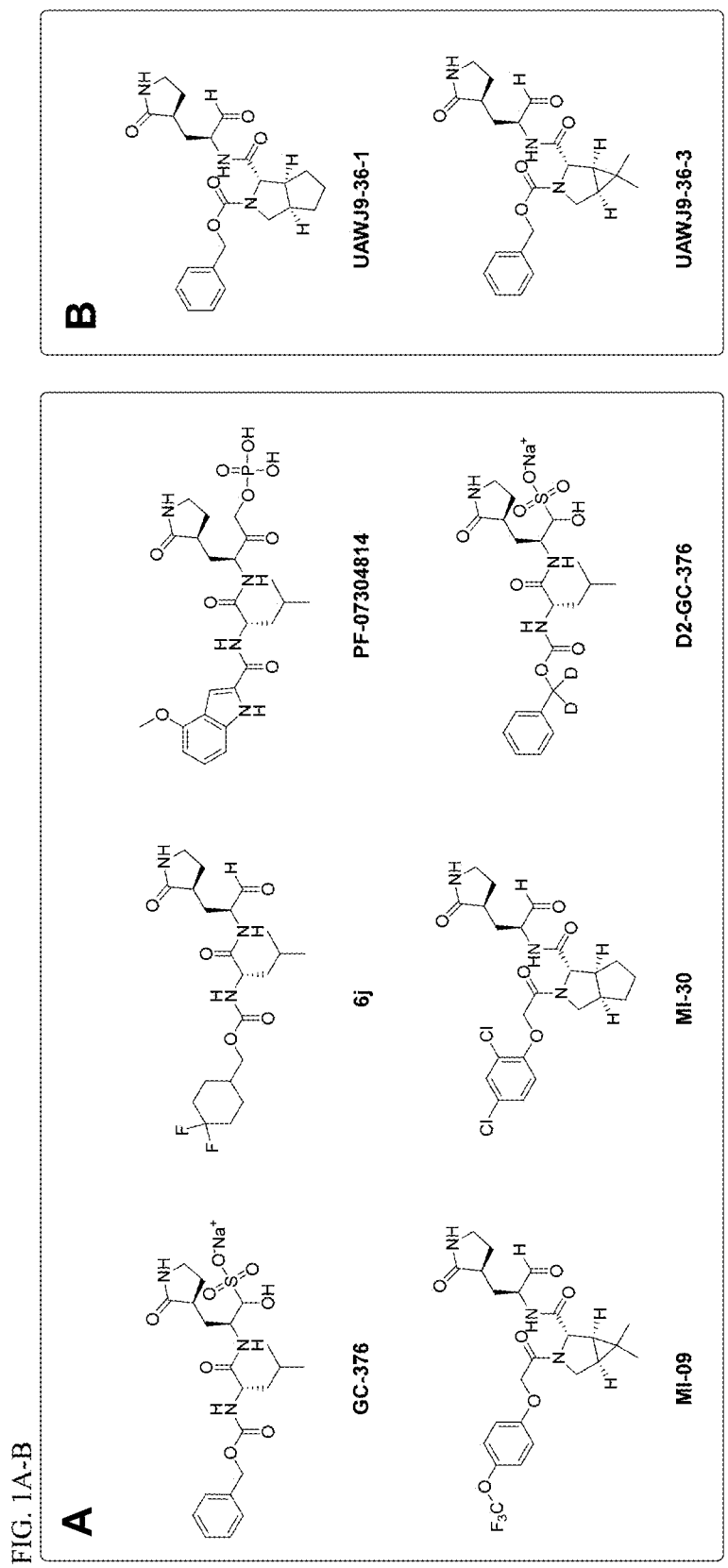
FIGS. 1A-B: SARS-CoV-2 M$^{pro}$ inhibitors. (A) Literature reported SARS-CoV-2 M$^{pro}$ inhibitors with in vivo antiviral efficacy. (B) Hybrid SARS-CoV-2 M$^{pro}$ inhibitors UAWJ9-36-1 and UAWJ9-36-3.

SARS-CoV-2 main protease)(M$^{pro}$) is a cysteine protease that mediates the cleavage of viral polyproteins and is a validated antiviral drug target. M$^{pro}$ is highly conserved among all seven human coronaviruses, with certain M$^{pro}$ inhibitors having broad-spectrum antiviral activity. Experiments conducted during the course of developing embodiments for the present invention resulted in the designing of two hybrid inhibitors UAWJ9-36-1 and UAWJ9-36-3 based on the superimposed X-ray crystal structures of SARS-CoV-2 M$^{pro}$ with GC-376, telaprevir and boceprevir. Both UAWJ9-36-1 and UAWJ9-36-3 showed potent binding and enzymatic inhibition against the M$^{pro}$s from SARS-CoV-2, SARS-CoV, MERS-CoV, HCoV-OC43, HCoV-NL63, HCoV-229E, and HCoV-HKU1. Cell-based Flip-GFP M$^{pro}$ assay found that UAWJ9-36-1 and UAWJ9-36-3 inhibited the intracellular protease activity of SARS-CoV-2 M$^{pro}$. In addition, UAWJ9-36-1 and UAWJ9-36-3 had potent antiviral activity against SARS-CoV-2, HCoV-OC43, HCoV-NL63, and HCoV-229E, with UAWJ9-36-3 more potent than GC-376 in inhibiting SARS-CoV-2. Selectivity profiling revealed that UAWJ9-36-1 and UAWJ9-36-3 had an improved selectivity index than GC-376 against host cysteine proteases calpain I and cathepsin L, but not cathepsin K. The X-ray crystal structures of SARS-CoV-2 M$^{pro}$ with UAWJ9-36-1 and UAWJ9-36-3 were both solved at 1.9 Å, which validated the design hypothesis. Overall, the hybrid inhibitors UAWJ9-36-1 and UAWJ9-36-3 are promising candidates to be further developed as broad-spectrum coronavirus antivirals.

Accordingly, the present invention relates to a new class of small-molecules having a pyrrolidinone-acetamide (or similar) structure which function as inhibitors of the SARS-CoV-2 papain-like protease (PL$^{pro}$), which function as inhibitors of the SARS-CoV-2 related viral 3CL protease (M$^{pro}$), which function as therapeutics for the treatment of viral infection characterized with PL$^{pro}$ and/or M$^{pro}$ protease activity and/or expression (e.g., COVID-19), and which function as therapeutics for the treatment of other conditions characterized with PL$^{pro}$ and/or M$^{pro}$ protease activity and/or expression.

In a particular embodiment, compounds encompassed within Formula I are provided:

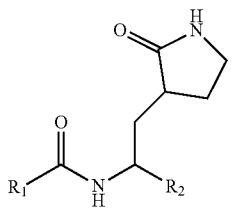

(Formula I), including pharmaceutically acceptable salts, solvates, and/or prodrugs thereof.

Formula I is not limited to a particular chemical moiety R1 and R2. In some embodiments, the particular chemical moiety for R1 and R2 independently include any chemical moiety that permits the resulting compound to inhibit PL$^{pro}$ protease activity. In some embodiments, the particular chemical moiety for R1 and R2 independently include any chemical moiety that permits the resulting compound to inhibit M$^{pro}$ protease activity. In some embodiments, the particular chemical moiety R1 and R2 independently include any chemical moiety that permits the resulting compound to prevent viral infection (e.g., COVID-19 infection).

Such embodiments are not limited to a particular definition for R1.

In some embodiments, R1 is selected from hydrogen,

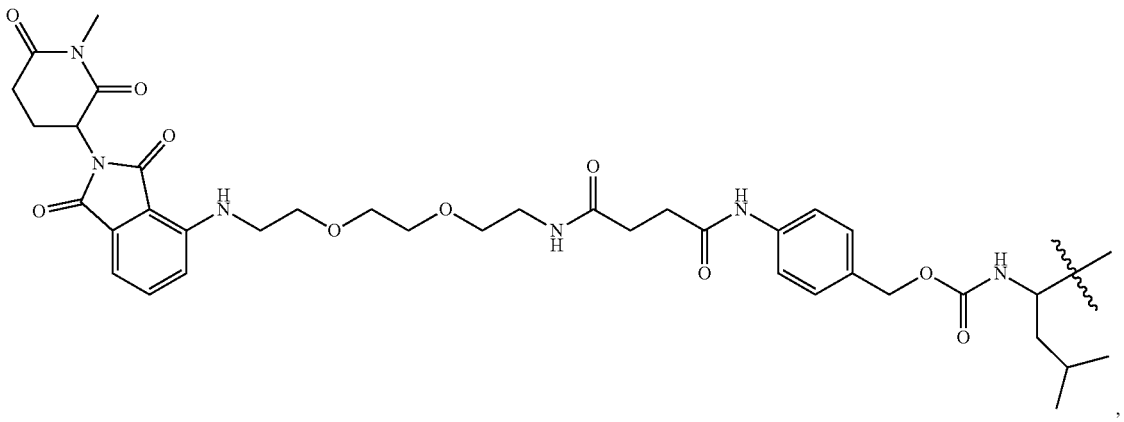

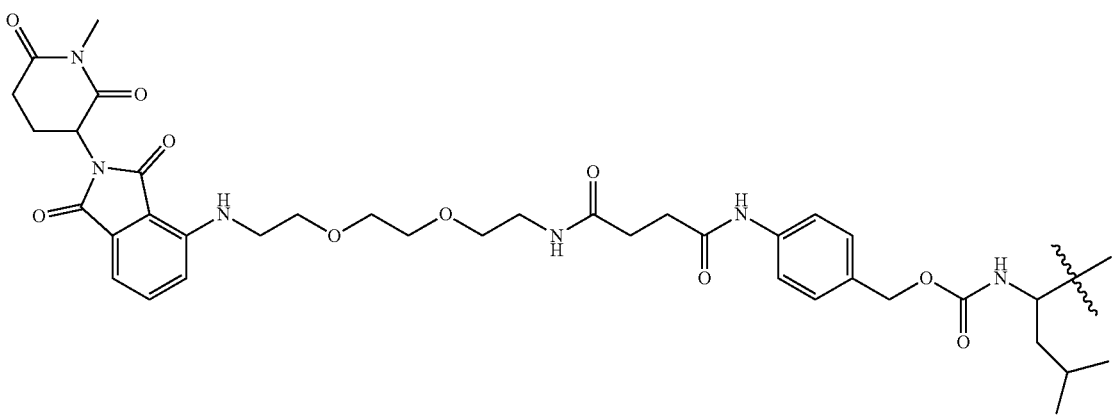

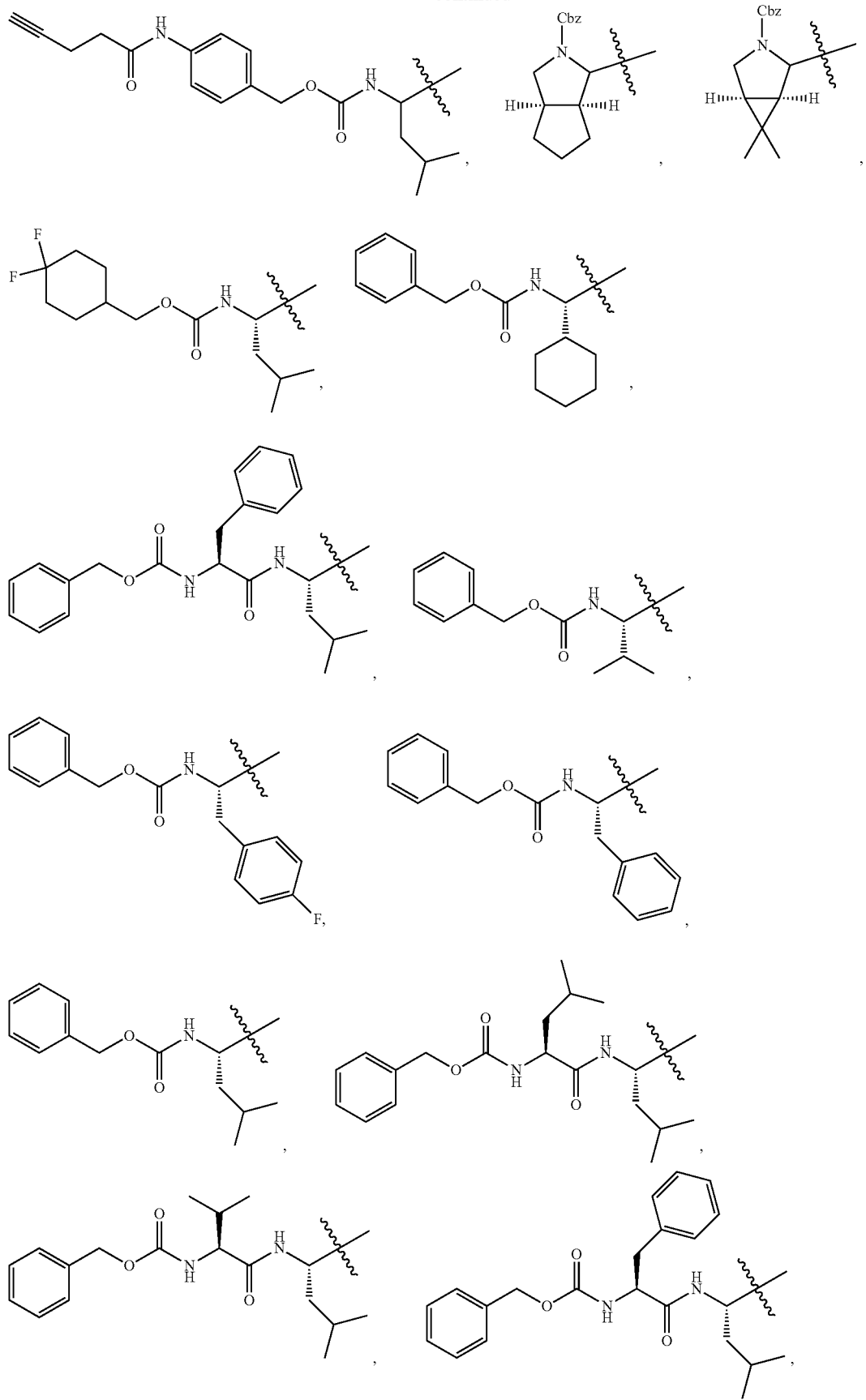

-continued

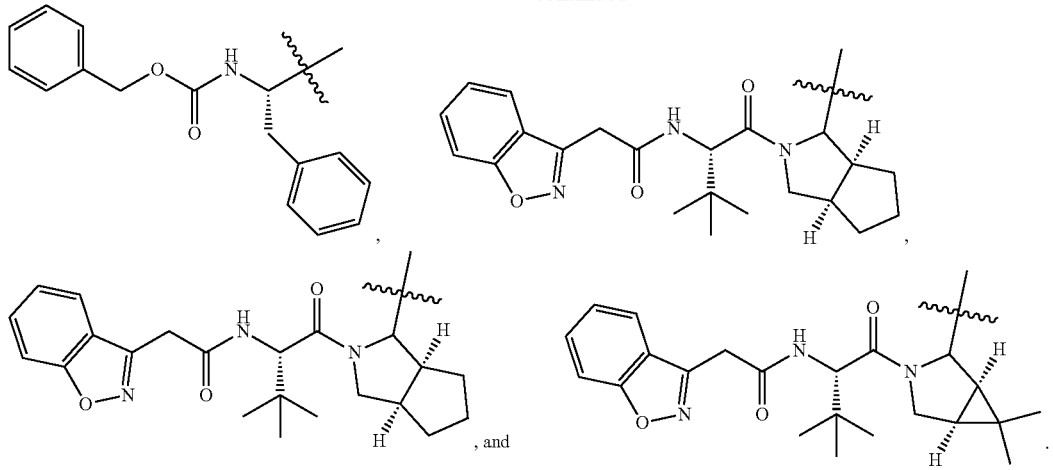

Such embodiments are not limited to a particular definition for R2.

In some embodiments, R2 is selected from hydrogen,

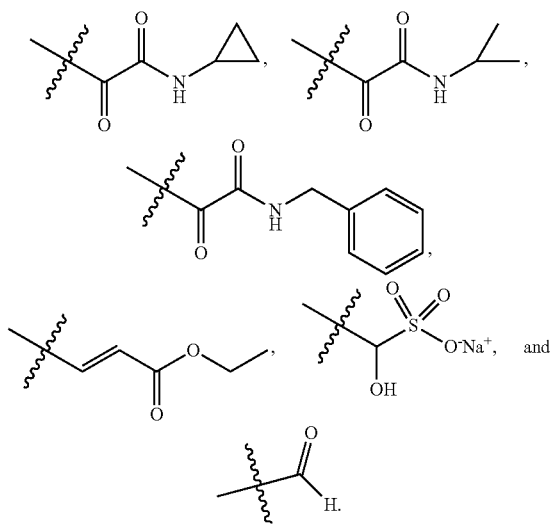

In some embodiments, the compound is recited in Table 1 (see, Example I).

An important aspect of the present invention is that the pharmaceutical compositions comprising one or more of compounds of the present invention are useful in treating viral infection (e.g., SARS-CoV-2 infection) and symptoms related to such a viral infection (e.g., fever, fatigue, dry cough, myalgias, dyspnea, acute respiratory distress syndrome, and pneumonia).

Some embodiments of the present invention provide methods for administering an effective amount of a pharmaceutical composition comprising one or more compounds of the present invention and at least one additional therapeutic agent (including, but not limited to, any pharmaceutical agent useful in treating SARS-CoV-2 infection and/or symptoms related to such a viral infection (e.g., fever, fatigue, dry cough, myalgias, dyspnea, acute respiratory distress syndrome, and pneumonia). In some embodiments, the additional agent is one or more of hydroxychloroquine, dexamethasone, and remdesivir.

In certain embodiments, the present invention provides methods for administering a pharmaceutical composition comprising one or more compounds of the present invention to a subject (e.g., a human subject) (e.g., a human subject suffering from or at risk of suffering from a condition related to SARS-CoV-2 infection (e.g., COVID-19)) for purposes of treating, preventing and/or ameliorating the symptoms of a viral infection (e.g., SARS-CoV-2 infection (e.g., COVID-19)).

In such embodiments, the methods are not limited treating, preventing and/or ameliorating the symptoms of a particular type or kind of viral infection. In some embodiments, the viral infection is a SARS-CoV-2 related viral infection (e.g., COVID-19). In some embodiments, the viral infection is any infection related to influenza, HIV, HIV-1, HIV-2, drug-resistant HIV, Junin virus, Chikungunya virus, Yellow Fever virus, Dengue virus, Pichinde virus, Lassa virus, adenovirus, Measles virus, Punta Toro virus, Respiratory Syncytial virus, Rift Valley virus, RHDV, SARS coronavirus, Tacaribe virus, and West Nile virus. In some embodiments, the viral infection is associated with any virus having PL$^{pro}$ protease activity and/or expression.

In such embodiments, administration of the pharmaceutical composition results in suppression of PL$^{pro}$ protease activity within the subject. In some embodiments, administration of the pharmaceutical composition results in suppression of any pathway related activity related to PL$^{pro}$ protease activity within the subject.

In such embodiments, administration of the pharmaceutical composition results in suppression of M$^{pro}$ protease activity within the subject. In some embodiments, administration of the pharmaceutical composition results in suppression of any pathway related activity related to M$^{pro}$ protease activity within the subject.

In some embodiments, the pharmaceutical composition comprising one or more compounds of the present invention is co-administered with one or more of hydroxychloroquine, dexamethasone, and remdesivir.

In certain embodiments, the present invention provides methods for treating, ameliorating and/or preventing a condition related to viral infection in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the viral infection is a SARS-CoV-2 viral infection.

In certain embodiments, the present invention provides methods for treating, ameliorating and/or preventing SARS-CoV-2 infection (e.g., COVID-19) in a subject, comprising administering to the subject a pharmaceutical composition comprising one or more compounds of the present invention. In some embodiments, the pharmaceutical composition comprising one or more compounds of the present invention is configured for oral administration. In some embodiments, the subject is a human subject.

In certain embodiments, the present invention provides methods for treating, ameliorating and/or preventing symptoms related to viral infection in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the subject is a human subject suffering from a SARS-CoV-2 viral infection. In some embodiments, the one or more symptoms related to viral infection includes, but is not limited to, fever, fatigue, dry cough, myalgias, dyspnea, acute respiratory distress syndrome, and pneumonia.

In certain embodiments, the present invention provides methods for treating, ameliorating and/or preventing symptoms related to SARS-CoV-2 infection (e.g., COVID-19) in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the one or more symptoms related to viral infection includes, but is not limited to, fever, fatigue, dry cough, myalgias, dyspnea, acute respiratory distress syndrome, and pneumonia.

In certain embodiments, the present invention provides methods for treating, ameliorating and/or preventing acute respiratory distress syndrome in a subject, comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the subject is a human subject suffering from a SARS-CoV-2 viral infection.

In certain embodiments, the present invention provides methods for treating, ameliorating and/or preventing acute respiratory distress syndrome related to SARS-CoV-2 infection (e.g., COVID-19) in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the subject is a human subject suffering from a SARS-CoV-2 viral infection.

In certain embodiments, the present invention provides methods for treating, ameliorating and/or preventing pneumonia in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the subject is a human subject suffering from a SARS-CoV-2 viral infection.

In certain embodiments, the present invention provides methods for treating, ameliorating and/or preventing pneumonia related to SARS-CoV-2 infection (e.g., COVID-19) in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the subject is a human subject suffering from a SARS-CoV-2 viral infection.

In some embodiments involving the treatment of acute respiratory distress syndrome and/or pneumonia, the pharmaceutical composition is administered in combination with a known agent to treat respiratory diseases. Known or standard agents or therapies that are used to treat respiratory diseases include, anti-asthma agent/therapies, anti-rhinitis agents/therapies, anti-sinusitis agents/therapies, anti-emphysema agents/therapies, anti-bronchitis agents/therapies or anti-chronic obstructive pulmonary disease agents/therapies. Anti-asthma agents/therapies include mast cell degranulation agents, leukotriene inhibitors, corticosteroids, beta-antagonists, IgE binding inhibitors, anti-CD23 antibody, tryptase inhibitors, and VIP agonists. Anti-allergic rhinitis agents/therapies include H1 antihistamines, alpha-adrenergic agents, and glucocorticoids. Anti-chronic sinusitis therapies include, but are not limited to surgery, corticosteroids, antibiotics, anti-fungal agents, salt-water nasal washes or sprays, anti-inflammatory agents, decongestants, guaifensesin, potassium iodide, luekotriene inhibitors, mast cell degranulating agents, topical moisterizing agents, hot air inhalation, mechanical breathing devices, enzymatic cleaners and antihistamine sprays. Anti-emphysema, anti-bronchitis or anti-chronic obstructive pulmonary disease agents/therapies include, but are not limited to oxygen, bronchodilator agents, mycolytic agents, steroids, antibiotics, anti-fungals, moisturization by nebulization, anti-tussives, respiratory stimulants, surgery and alpha 1 antitrypsin.

In certain embodiments, the present invention provides methods for inhibiting viral entry in a cell, comprising exposing the cell to a pharmaceutical composition comprising one or more compounds of the present invention. In some embodiments, the cell is at risk of viral infection (e.g., a cell at risk of SARS-CoV-2 infection). In some embodiments, the cell has been exposed to a virus (e.g., a cell currently exposed to SARS-CoV-2). In some embodiments, the cell is in culture. In some embodiments, the cell is a living cell in a subject (e.g., a human subject) (e.g., a human subject suffering from COVID-19) (e.g., a human subject at risk of suffering from COVID-19). In some embodiments, exposure of the cell to the pharmaceutical composition comprising one or more compounds of the present invention results in suppression of $PL^{pro}$ activity within the cell. In some embodiments, exposure of the cell to the pharmaceutical composition comprising one or more compounds of the present invention results in suppression of $M^{pro}$ activity within the cell.

In certain embodiments, the present invention provides kits comprising a pharmaceutical composition comprising one or more compounds of the present invention, and one or more of (1) a container, pack, or dispenser, (2) one or more additional agents selected from hydroxychloroquine, dexamethasone, and remdesivir, and (3) instructions for administration.

Compositions within the scope of this invention include all pharmaceutical compositions contained in an amount that is effective to achieve its intended purpose. While individual needs vary, determination of optimal ranges of effective amounts of each component is within the skill of the art. Typically, the pharmaceutical agents which function as inhibitors of $PL^{pro}$ and/or $M^{pro}$ protease activity may be administered to mammals, e.g. humans, orally at a dose of 0.0025 to 50 mg/kg, or an equivalent amount of the pharmaceutically acceptable salt thereof, per day of the body weight of the mammal being treated. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the inhibiting agent. The unit dose may be administered one or more times daily as one or more tablets or capsules each containing from about 0.1 to about 10 mg, conveniently about 0.25 to 50 mg of the agent (e.g., small molecule) or its solvates.

In a topical formulation, a compound of the present invention (e.g., a compound having a methyl-acetamido-propanamide structure) may be present at a concentration of about 0.01 to 100 mg per gram of carrier. In a one embodiment, such a compound is present at a concentration of about 0.07-1.0 mg/ml, for example, about 0.1-0.5 mg/ml, and in one embodiment, about 0.4 mg/ml.

In addition to administering a compound of the present invention (e.g., a compound having a methyl-acetamido-propanamide structure) as a raw chemical, it may be administered as part of a pharmaceutical preparation containing suitable pharmaceutically acceptable carriers comprising excipients and auxiliaries which facilitate processing of the compound into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active mimetic peptide(s), together with the excipient.

The pharmaceutical compositions of the invention may be administered to any patient that may experience the beneficial effects of one or more of compounds of the present invention (e.g., compounds having a methyl-acetamido-propanamide structure). Foremost among such patients are mammals, e.g., humans, although the invention is not intended to be so limited. Other patients include veterinary animals (cows, sheep, pigs, horses, dogs, cats and the like).

The pharmaceutical compositions comprising a compound of the present invention (e.g., a compound having a methyl-acetamido-propanamide structure) may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner that is itself known, for example, by means of conventional mixing, granulating, dragee-making, dissolving, or lyophilizing processes. Thus, pharmaceutical preparations for oral use can be obtained by combining the active mimetic peptides with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye-stuffs or pigments may be added to the tablets or dragee coatings, for example, for identification or in order to characterize combinations of active mimetic peptide doses.

Other pharmaceutical preparations that can be used orally include push-fit capsules made of gelatin, as well as soft, sealed capsules made of gelatin and a plasticizer such as glycerol or sorbitol. The push-fit capsules can contain the active mimetic peptides in the form of granules that may be mixed with fillers such as lactose, binders such as starches, and/or lubricants such as talc or magnesium stearate and, optionally, stabilizers. In soft capsules, the active mimetic peptides are in one embodiment dissolved or suspended in suitable liquids, such as fatty oils, or liquid paraffin. In addition, stabilizers may be added.

Possible pharmaceutical preparations that can be used rectally include, for example, suppositories, which consist of a combination of one or more of the active mimetic peptides with a suppository base. Suitable suppository bases are, for example, natural or synthetic triglycerides, or paraffin hydrocarbons. In addition, it is also possible to use gelatin rectal capsules that consist of a combination of the active mimetic peptides with a base. Possible base materials include, for example, liquid triglycerides, polyethylene glycols, or paraffin hydrocarbons.

Suitable formulations for parenteral administration include aqueous solutions of the active mimetic peptides in water-soluble form, for example, water-soluble salts and alkaline solutions. In addition, suspensions of the active mimetic peptides as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Ointments may be formulated by mixing a solution of the active ingredient in a vegetable oil such as almond oil with warm soft paraffin and allowing the mixture to cool. A typical example of such an ointment is one that includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXPERIMENTAL

Example I

Rational Design of SARS-CoV-2 $M^{pro}$ Inhibitors

The superimposed co-crystal structures of GC-376 with telaprevir showed that the pyrrolidone from GC-376 and the norvaline from telaprevir fit in the 51 pocket (FIGS. 2A-C). Consistent with its Gln substrate preference, pyrrolidone is a preferred substitution at the P1 position where it forms two or three hydrogen bonds with the H163, E166, and F140 in the S1 pocket, while norvaline from telaprevir does not form any specific interaction. The leucine from GC-376 and the cyclopentylproline from telaprevir fit in the S2 hydrophobic pocket (FIGS. 2A-C). Since cyclopentylproline forms more hydrophobic interactions than leucine in the S2 pocket, we hypothesize that it might be a preferred substitution at the P2 position. The tert-leucine substitution at the P3 position of telaprevir was solvent exposed. Because previous structure-activity relationship studies have shown that P3 substitution does not contribute significantly to the enzymatic inhibition,[10] we (the inventors) decided to omit P3 substitution. The carboxybenzyl (Cbz) group from GC-376 and the cyclohexane from telaprevir fit in the S4 pocket, and both are engaged in hydrophobic interactions. Based on the overlaying structures, we designed the hybrid inhibitor UAWJ9-36-1, which integrates the favorable substitutions pyrrolidone at the P1, cyclopentylproline at P2, and benzyl at P4 position (FIG. 2D). Using a similar strategy, UAWJ9-36-3 was designed as a hybrid of GC-376 and boceprevir, which contains dimethylcyclopropylproline at the P2 position (FIGS. 2A, 2E-G).

Synthesis of Hybrid Inhibitors UAWJ9-63-1 and UAWJ9-63-3

Figure 3:
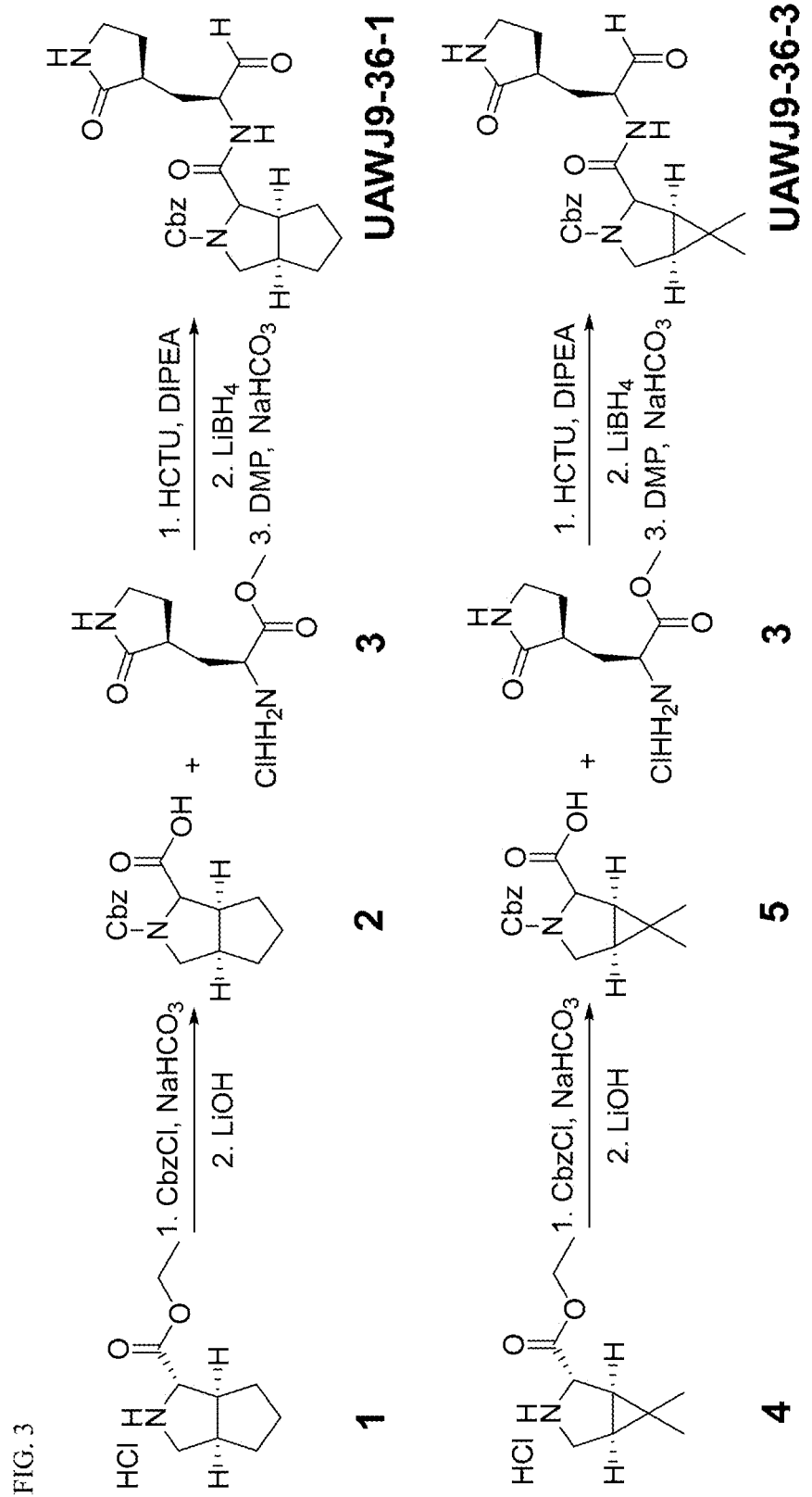
FIG. 3: Synthesis of the hybrid inhibitors UAWJ9-36-1 and UAWJ9-36-3.

The synthesis of UAWJ9-63-1 and UAWJ9-63-3 started with commercially available amino esters 1 and 4 (FIG. 3). Protecting the amine with the Cbz and subsequent hydrolysis of the ester gave the carboxylic acid intermediates 2 and 5. Subsequent coupling with the pyrrolidone intermediate 3, followed by reduction and oxidation gave the final products UAWJ9-36-1 and UAWJ9-36-3.

Figure 5G:
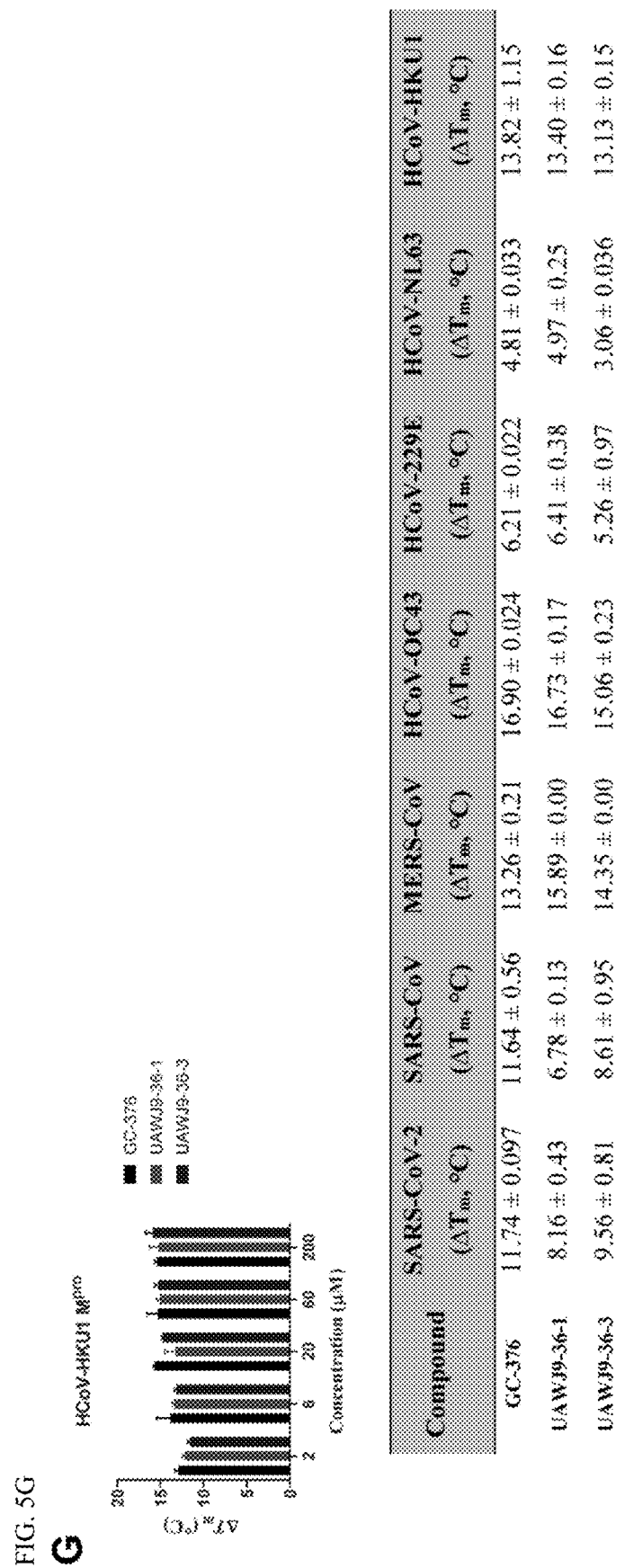

Enzymatic Inhibition of UAWJ9-36-1 and UAWJ9-36-3 Against the $M^{pro}$s From Seven Human Coronaviruses The enzymatic inhibition of UAWJ9-36-1 and UAWJ9-36-3 against the $M^{pro}$s from all seven human coronaviruses including SARS-CoV-2, SARS-CoV, MERS-CoV, HCoV-OC43, HCoV-229E, HCoV-NL63, and HCoV-HKU1 was tested in the FRET-based enzymatic assay (FIG. 4). GC-376 was included as a control since it represents one of the most potent SARS-CoV-2 $M^{pro}$ reported so far. It was found that UAWJ9-36-1 and UAWJ9-36-3 were equally potent and had comparable enzymatic inhibition as GC-376 for all seven $M^{pro}$s tested (FIG. 4). UAWJ9-36-1 and UAWJ9-36-3 inhibited the HCoV-NL63 $M^{pro}$ with $IC_{50}$ values of 0.36 and 0.45 µM, respectively, which were less potent compared to their inhibition of other $M^{pro}$s. A thermal shift binding assay showed that UAWJ9-36-1 and UAWJ9-36-3 significantly increased melting temperature shift ($\Delta T_m$) (FIG. 5), indicating protein stabilization. Consistent with the enzymatic assay results, UAWJ9-36-1 and UAWJ9-36-3 were less potent in binding to the HCoV-NL63 $M^{pro}$ compared to others. Overall, the enzymatic assay and the thermal shift-binding assay found that UAWJ9-36-1 and UAWJ9-36-3 are potent inhibitors of the $M^{pro}$s from all seven human coronaviruses.

Cellular Protease Inhibitory Activity of UAWJ9-36-1 and UAWJ9-36-3 in the Flip-GFP $M^{pro}$ Assay Although the FRET-based enzymatic assay is commonly used as a primary assay for the testing of SARS-CoV-2 $M^{pro}$ inhibitors, the in vitro results from this assay might not have a direct correlation with the cellular activity due to issues with drug efflux, cytotoxicity, membrane permeability, metabolism, off-target binding and etc.[23-25] As such, we adapt the Flip-GFP assay to quantify the cellular protease inhibitory activity of UAWJ9-36-1 and UAWJ9-36-3 against the SARS-CoV-2 $M^{pro}$ (FIG. 6). In the Flip-GFP assay, 293T cells were transfected with two plasmids, one expressing the SARS-CoV-2 $M^{pro}$, another expressing the Flip-GFP construct with the $M^{pro}$ cleavage site (Flip-GFP $M^{pro}$) (FIGS. 6A-B).[26-27] Specifically, the Flip-GFP $M^{pro}$ construct expresses two GFP fragments, the β10-11 fragment and the β1-9 template. The β10-11 fragment contains a $M^{pro}$ cleavage sequence (AVLQ↓SGFR). Upon cleavage by the $M^{pro}$, the β11 strand will be able to assemble with the (β1-9 template together with the β10 strand, leading to the restoration of green fluorescence signal (FIG. 6A). The Flip-GFP $M^{pro}$ also expresses the mCherry red fluorescence protein, which serves as an internal control for the normalization of the protein expression level (FIG. 6B). As shown in FIG. 6C, strong green fluorescence signals were only observed when there is a match between the protease and its cleavage site (second and eight rows). No or minimal GFP signal was observed in cases there is a mismatch between the protease and its cleavage site (third, fourth, and fifth rows), or no $M^{pro}$ (sixth row), or the inactive $M^{pro}$ (C145A) (seventh row). GC-376 showed dose dependent inhibition in the Flip-GFP assay with an $IC_{50}$ of 4.83 µM (FIGS. 6D and 6G). UAWJ9-36-1 was less active showing an $IC_{50}$ of 11.10 µM (FIGS. 6E and 6G), while UAWJ9-36-3 was more potent than GC-376 and had an $IC_{50}$ value of 3.40 µM (FIGS. 6D and 6G). Overall, the Flip-GFP $M^{pro}$ assay suggested that the UAWJ9-36-1 and UAWJ9-36-1 might have the cellular antiviral activity with rank of potency in the order of UAWJ9-36-3>GC-376>UAWJ9-36-1.

Broad-Spectrum Antiviral Activity of UAW/19-36-1 and UAW/J9-36-3 Against SARS-CoV-2 and Human Coronaviruses HCoV-OC43, HCoV-229E, and HCoV-NL63

The antiviral activity of UAWJ9-36-1 and UAWJ9-36-3 against SARS-CoV-2 was tested using immunofluorescence assay in two cell lines, Vero E6 and Caco2-ACE2 (FIGS. 7A-D). Caco2-ACE2 expresses TMPRSS2, and is a physiologically relevant cell line for SARS-CoV-2 replication.[28-30] It was found that UAWJ9-36-1 was less potent than GC-376 in inhibiting SARS-CoV-2 in both cell lines. Gratifyingly, UAWJ9-36-3 had improved antiviral activity than GC-376 and inhibited SARS-CoV-2 replication in Vero E6 cells and Caco2-ACE2 cells with $EC_{50}$ values of 0.37 and 1.06 µM (FIGS. 7A-D). The relative antiviral activity of these three compounds was in agreement with the results from the cell-based Flip-GFP $M^{pro}$ assay (FIG. 6), suggesting that the Flip-GFP $M^{pro}$ assay represents a viable assay to screen $M^{pro}$ inhibitors. The antiviral activity of UAWJ9-36-1 and UAWJ9-36-3 against HCoV-OC43 was tested in the plaque assay and both were highly potent with $EC_{50}$ values of 46 and 59 nM, respectively (FIGS. 7F-G). In comparison, GC-376 inhibited HCoV-OC43 with an $EC_{50}$ value of 60 nM (FIG. 7E). Their antiviral activity against HCoV-229E and HCoV-NL63 was tested in the CPE assay (FIGS. 7H-P). UAWJ9-36-1 and UAWJ9-36-3 were equally potent in inhibiting HCoV-229E with $EC_{50}$ values of 0.17 and 0.13 µM, respectively (FIGS. 7I-J). The antiviral activity of these two compounds against HCoV-NL63 was tested in two cell lines, Vero E6 and Huh-7 (FIGS. 7K-P). UAWJ9-36-1 and UAWJ9-36-3 were less potent in the Vero E6 cells than in the Huh-7 cells, which might be due to the drug efflux pump P-glycoprotein (P-gp) expressed on the Vero E6 cells.[31] GC-376 and its analogs were previously shown to be the substrates of P-gp.[15, 23, 32] To test this hypothesis, we repeated the antiviral assay in the presence of P-gp inhibitor CP-100356. It was found that the antiviral activity of UAWJ9-36-1 and UAWJ9-36-3 against HCoV-NL63 in Vero E6 cells increased in the presence of CP-100356 (FIGS. 7O-P).

Selectivity of UAWJ9-36-1 and UAWJ9-36-3 Against Human Cysteine and Serine Proteases Previous studies showed that GC-376 and its analogs also inhibit cathepsin L in addition to the SARS-CoV-2 $M^{pro}$.[23, 32] In addition, all three compounds GC-376, UAWJ9-36-1 and UAWJ9-36-3 contain aldehydes as a reactive warhead; therefore, they might be a potential concern with the off-target effect in inhibiting host cysteine proteases. To test this hypothesis, we profiled the selectivity of these two hybrid compounds against host cysteine proteases calpain I, cathepsin K, cathepsin L, and caspase-3, as well as the serine protease trypsin (FIG. 8). GC-376 was included as a control. GC-376 was a potent inhibitor of calpain I with an $IC_{50}$ of 0.074 µM, while UAWJ9-36-1 and UAWJ9-36-3 had drastically reduced inhibition with $IC_{50}$ values of 16.56 and >20 µM, respectively (FIG. 8A). Consistent with previous results, GC-376 was also a potent inhibitor of cathepsin L with an $IC_{50}$ of 4.4 nM,[23, 32] while UAWJ9-36-1 and UAWJ9-36-3 were weak inhibitors of cathepsin L with $IC_{50}$ values of 1.37 and 1.81 µM, respectively. GC-376 had potent inhibition against cathepsin K with an $IC_{50}$ of 0.26 nM, and UAWJ9-36-1 and UAWJ9-36-3 had slightly improved selectivity but still had potent inhibition with $IC_{50}$ values of 6.5 and 42 nM, respectively. All three compounds did not inhibit caspase-3 or trypsin ($IC_{50}$>20 µM). Overall, UAWJ9-36-1 and UAWJ9-36-3 had an improved selectivity index than GC-376 in inhibiting calpain I and cathepsin L, but not cathepsin K.

X-Ray Crystal Structures of SARS-CoV-2 $M^{pro}$ in Complex With UAWJ9-36-1 and UAWJ9-36-3

Figure 2:
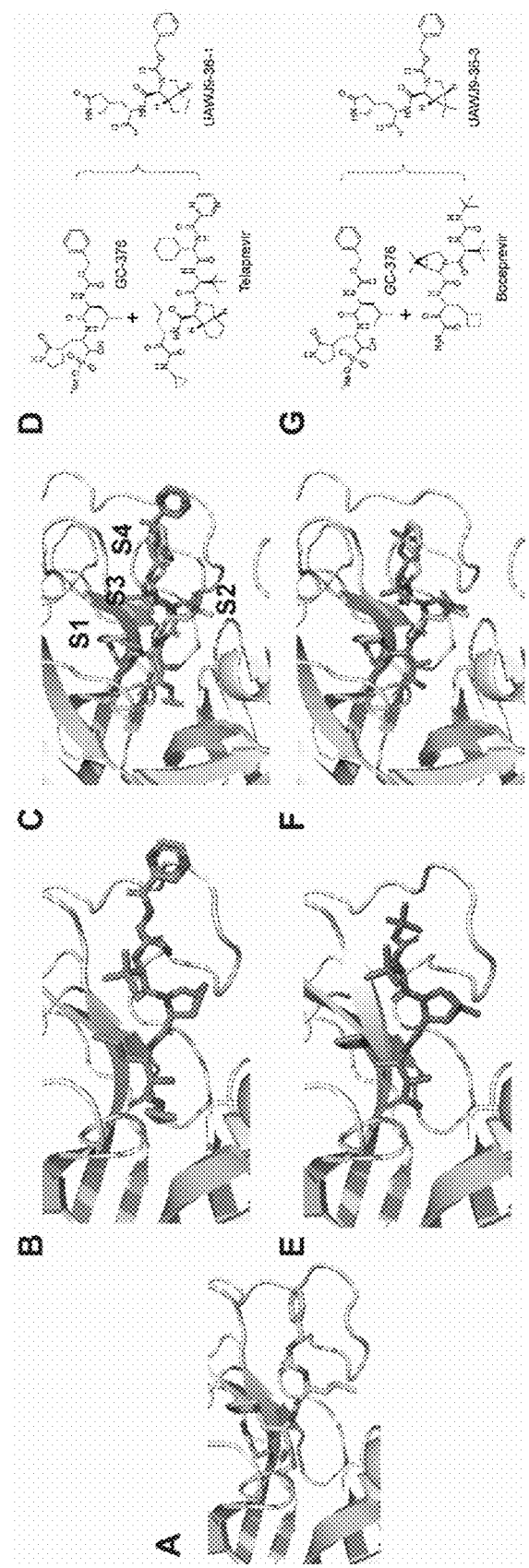
FIGS. 2A-G: Structure-guided design of SARS-CoV-2 M$^{pro}$ hybrid inhibitors based on superimposed X-ray crystal structures. (A) X-ray crystal structure of SARS-CoV-2 M$^{pro}$ with GC-376 (PDB: 6WTT). (B) X-ray crystal structure of SARS-CoV-2 M$^{pro}$ with telaprevir (PDB: 6XQS). (C) Overlaying X-ray crystal structures of M$^{pro}$ in complex with GC-376 and telaprevir. (D) Design UAWJ9-36-1 as a hybrid of GC-376 and telaprevir. (E) X-ray crystal structure of SARS-CoV-2 M$^{pro}$ with boceprevir (PDB: 6XQU). (F) Overlaying X-ray crystal structures of M$^{pro}$ in complex with GC-376 and boceprevir. (G) Design UAWJ9-36-3 as a hybrid of GC-376 and boceprevir.

X-ray crystal structures of UAWJ9-36-1 and UAWJ9-36-3 with SARS-CoV-2 $M^{pro}$ were both solved at 1.9 Å resolution (FIG. 9, Table 1), revealing a binding pose that is consistent with our projections (FIG. 2). In the P1 position, we found the pyrroldinone ring interacts with the S1 pocket, forming H-bonds with E166, H163, and the mainchain of F140. The cyclopentylproline and dimethylcyclopropylproline moieties of UAWJ9-36-1 and UAWJ9-36-3 occupy the hydrophobic S2 sites almost identically to their telaprevir and boceprevir analogues (FIGS. 9E, 9F). Interestingly, the Cbz group adopts two different poses in UAWJ9-36-1 and UAWJ9-36-3. In UAWJ9-36-1, the Cbz group adheres to the substrate groove, covering the amide binding segment of the S3 and S4 sites (FIG. 9B). In UAWJ9-36-3 the Cbz flips up towards the weakly defined S3 site (FIG. 9C). The variable binding conformation of the Cbz group has been observed in multiple structures of GC-376 and GC-376 analogues.[10] It is not entirely clear what determines this pose, but given the nonspecific nature of the interactions at the S3 and S4 subsites, it is possible these populations exists in dynamic equilibrium, with individual poses promoted by the crystallization condition and nearby residues. Two different constructs of $M^{pro}$ from our previous studies were used: the native $M^{pro}$ for UAWJ9-36-1, and HM-$M^{pro}$ (with two extra residues in the N-terminus) for UAWJ9-36-3. As the N-terminus of one protomer is in close proximity to the active site of the other protomer in the $M^{pro}$ dimer, this has resulted in differences in the conformation of E166 that interacts with the pyrroldinone ring of the inhibitor, which may in turn influence the conformation of the Cbz ring in a specific crystal structure. However, based on previous $M^{pro}$ complex structures, both conformations of the Cbz may be relevant to the activity of the inhibitor, due to the flexible nature and the favorable protein interactions of both conformations.

TABLE 1

Crystallization Statistics. Values in parentheses correspond to the highest-resolution shell.

|  | PDB ID 7LYI | PDB ID 7LYH |
|---|---|---|
| Data Collection |  |  |
| Inhibitor | UAWJ9-36-3 | UAWJ9-36-1 |
| Space Group | C 1 2 1 | I 1 2 1 |
| Cell Dimension |  |  |
| a, b, c (Å) | 113.9, 54.31, 45.17 | 45.62, 53.02, 112.96 |
| α, β, γ (°) | 90, 101.1, 90 | 90, 100.71, 90 |
| Resolution (Å) | 48.90-1.90 (1.94-1.90) | 47.89-1.90 (1.94-1.90) |
| $R_{merge}$ | 0.061 (0.225) | 0.105 (0.441) |
| $<I>/\sigma<I>$ | 6.5 (3.0) | 8.7 (4.0) |
| Completeness (%) | 93.0 (89.7) | 96.2 (98.2) |
| Multiplicity | 2.5 (2.3) | 4.3 (4.4) |

TABLE 1-continued

Crystallization Statistics. Values in parentheses correspond to the highest-resolution shell.

|  | PDB ID 7LYI | PDB ID 7LYH |
|---|---|---|
| Refinement |  |  |
| Resolution (Å) | 48.70-1.90 (1.97-1.90) | 47.84-1.90 (1.97-1.90) |
| No. reflections/free | 18899/983 | 20154/2030 |
| $R_{work}/R_{free}$ | 0.1799/0.2219 | 0.1853/0.2250 |
| No. Atoms | 2513 | 2689 |
| Protein | 2364 | 2449 |
| Ligand/Ion | 38 | 43 |
| Water | 111 | 197 |
| B-Factors (Å²) | 39.72 | 21.78 |
| Protein | 39.77 | 20.98 |
| Ligand/Ion | 27.66 | 25.67 |
| Solvent | 42.74 | 30.84 |
| RMS Deviations |  |  |
| Bond Lengths (Å) | 0.015 | 0.014 |
| Bond Angles (°) | 1.92 | 1.79 |
| Ramachandran Favored (%) | 98.01 | 98.01 |
| Ramachandran Allowed (%) | 1.99 | 1.99 |
| Ramachandran Outliers (%) | 0.00 | 0.00 |
| Rotameric Outliers (%) | 1.91 | 1.83 |
| Clashscore | 3.18 | 4.27 |

Table 2 shows cytotoxicity and inhibition values of $PL^{pro}$ and/or $M^{pro}$ protease activity for compounds of the present invention.

TABLE 2

|  | Cytotoxicity |
|---|---|

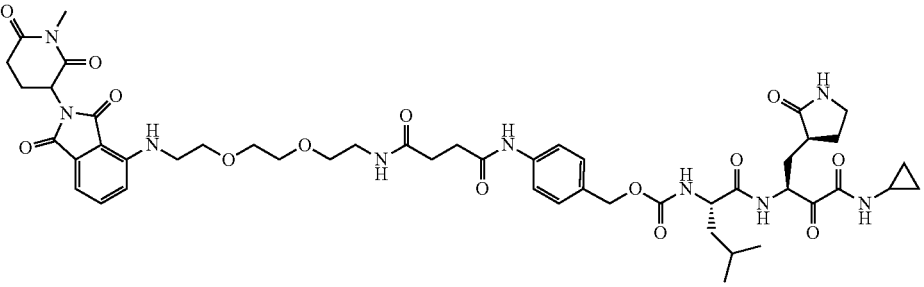

SARS-CoV-2 $M^{pro}$ IC$_{50}$ = 0.11 μM

Jun9-73-2

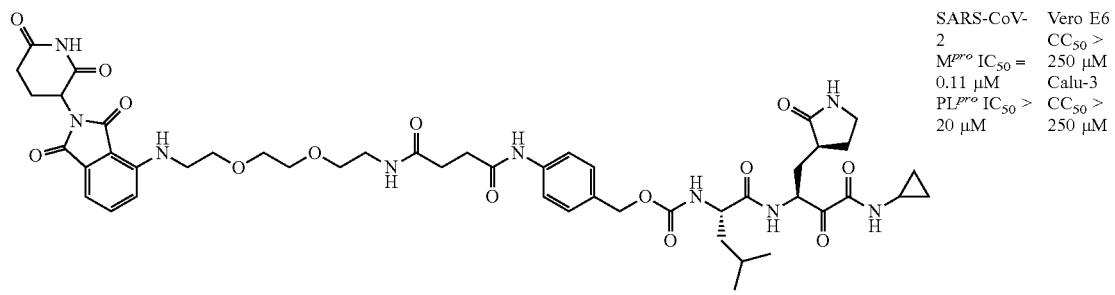

SARS-CoV-2 $M^{pro}$ IC$_{50}$ = 0.11 μM
$PL^{pro}$ IC$_{50}$ > 20 μM

Vero E6 CC$_{50}$ > 250 μM
Calu-3 CC$_{50}$ > 250 μM

ZX-132

TABLE 2-continued
| | Cytotoxicity |
|---|---|
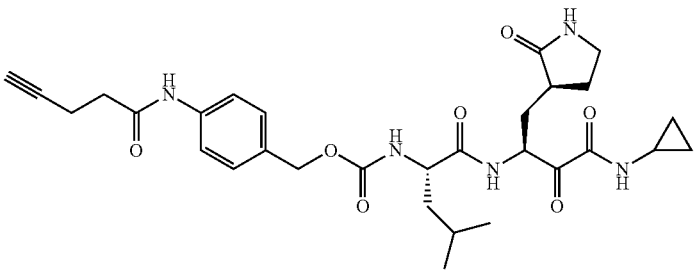
Jun9-58-3
SARS-CoV-2 $M^{pro}$ $IC_{50}$ = 0.15 μM
$PL^{pro}$ $IC_{50}$ > 20μM
Vero E6 $CC_{50}$ > 250 μM
Calu-3 $CC_{50}$ > 250 μM
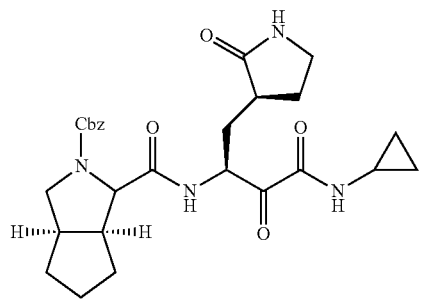
Jun9-36-2
SARS-CoV-2 $M^{pro}$ $IC_{50}$ = 0.13 μM
Vero E6 $CC_{50}$ > 250 μM
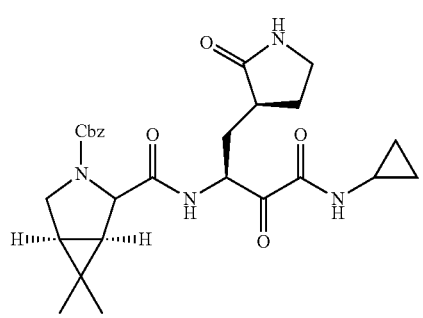
Jun9-36-4
SARS-CoV-2 $M^{pro}$ $IC_{50}$ = 0.20 μM
Vero E6 $CC_{50}$ > 250 μM
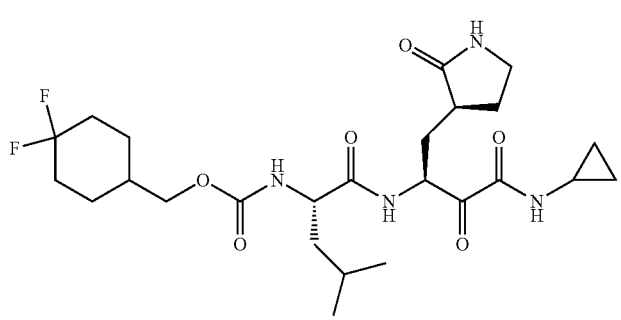
Jun9-9-3
SARS-CoV-2 $M^{pro}$ $IC_{50}$ = 0.06 μM
Antiviral activity in Calu-3 cells $EC_{50}$ = 2.6 μM
Vero E6 $CC_{50}$ > 250 μM TABLE 2-continued

| Structure | Cytotoxicity |
|---|---|
| Jun8-51-2 | SARS-CoV-2 $M^{pro}$ IC$_{50}$ = 0.38 μM; PL$^{pro}$ IC$_{50}$ > 20 μM |
| Jun8-51-3 | SARS-CoV-2 MP$^{pro}$ IC$_{50}$ = 0.13 μM; PL$^{pro}$ IC$_{50}$ > 20 μM |
| Jun8-51-4 | SARS-CoV-2 $M^{pro}$ IC$_{50}$ = 0.09 μM; PL$^{pro}$ IC$_{50}$ > 20 μM |
| Jun8-37-1 | SARS-CoV-2 $M^{pro}$ IC$_{50}$ = 1.29 μM |

TABLE 2-continued
| Structure | | Cytotoxicity |
|---|---|---|
| 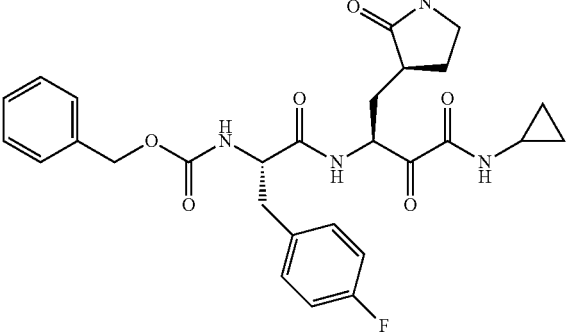  Jun8-37-2 | SARS-CoV-2 $M^{pro}$ IC$_{50}$ = 5.50 μM | |
| 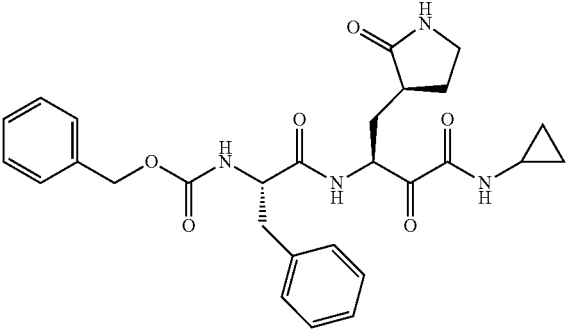  Jun8-24-5 (UAWJ246) | SARS-CoV-2 $M^{pro}$ IC$_{50}$ = 0.78 ± 0.16 μM | Caco2 CC$_{50}$ > 100 μM  A549 CC$_{50}$ > 100 μM |
| 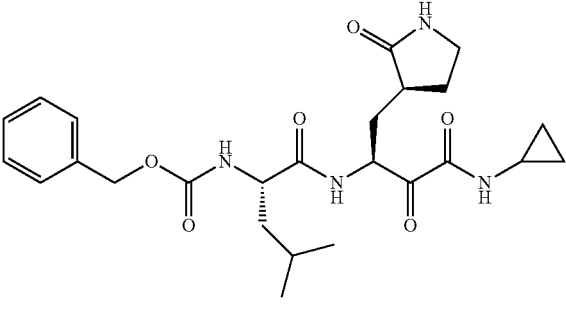  Jun8-24-3 | SARS-CoV-2 $M^{pro}$ IC$_{50}$ = 0.045 ± 0.012 μM | Caco2 CC$_{50}$ > 100 μM  A549 CC$_{50}$ > 100 μM |
| 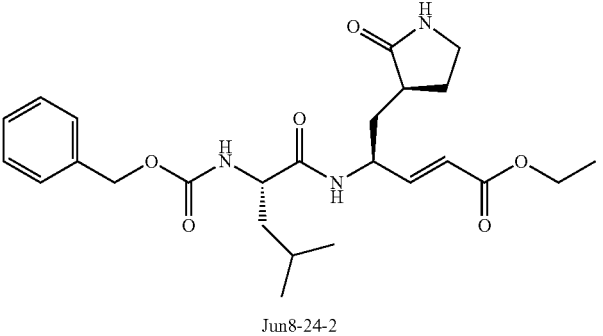 [SMILES: CCOC(=O)/C=C/[C@H](C[C@@H]1CCNC1=O)NC(=O)[C@H](CC(C)C)NC(=O)OCc1ccccc1]  Jun8-24-2 | SARS-CoV-2 $M^{pro}$ IC$_{50}$ = 1.71 ± 0.20 μM | |

TABLE 2-continued
| | Cytotoxicity |
|---|---|
| 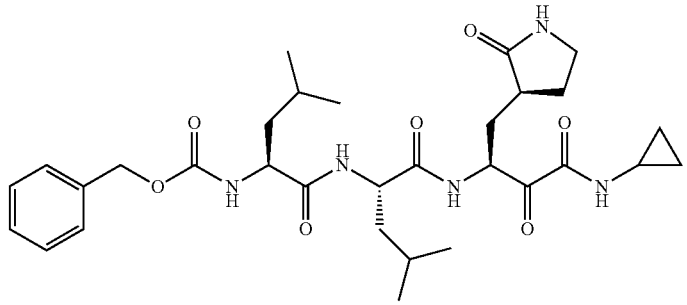\nJun8-37-3 (UAWJ248) | SARS-CoV-2 $M^{pro}$ IC$_{50}$ = 0.012 μM |
| 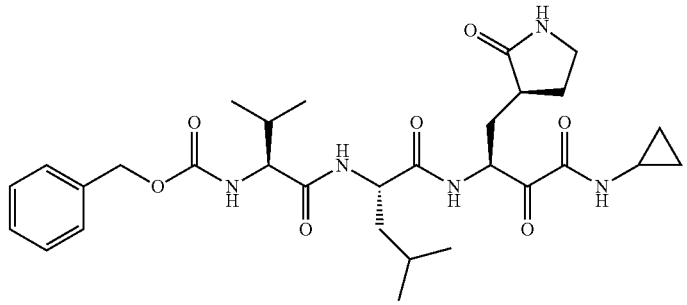\nJun8-37-4 | SARS-CoV-2 $M^{pro}$ IC$_{50}$ = 0.014 μM |
| 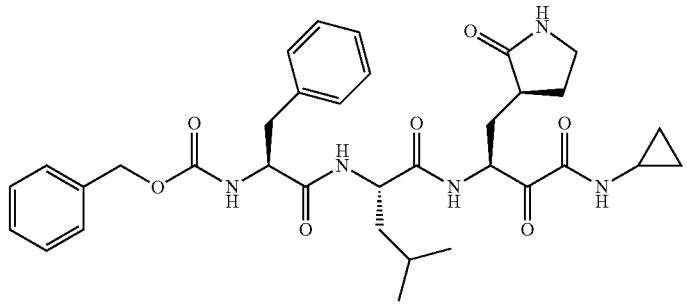\nJun8-37-5 | SARS-CoV-2 $M^{pro}$ IC$_{50}$ = 0.013 μM |
| 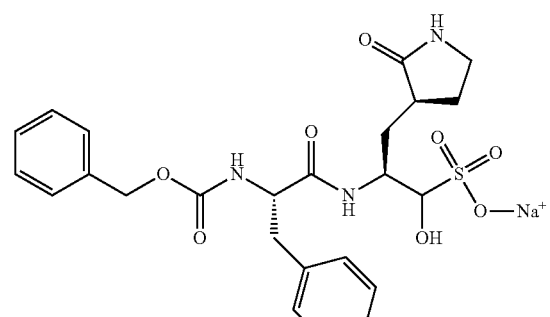\nJun8-34-2 (UAWJ247) | SARS-CoV-2 $M^{pro}$ IC$_{50}$ = 0.04 μM |

TABLE 2-continued

Cytotoxicity

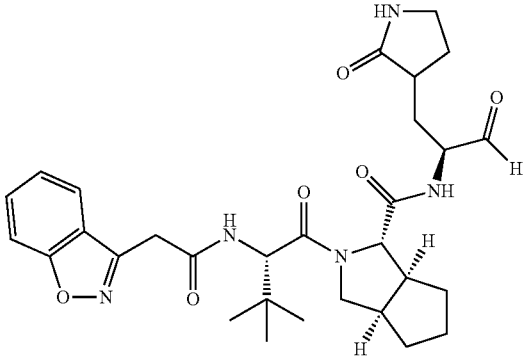 [SMILES: CC(C)(C)[C@H](NC(=O)Cc1noc2ccccc12)C(=O)N1C[C@@H]2CCC[C@@H]2[C@H]1C(=O)N[C@H](C=O)CC1CCNC1=O]

CONCLUSION

In parallel to our study, two compounds MI-09 and MI-30 (FIG. 1) with a similar design were reported to have both in vitro and in vivo antiviral activity against SARS-CoV-2 infection.[16] The results from the hybrid molecules designed in this study UAWJ9-36-1 and UAWJ9-36-3 provided additional evidence to support the translational potential of this series of compounds. Highlights from this study include: 1) we solved the X-ray crystal structure of SARS-CoV-2 M$^{pro}$ in complex with both the cyclopentylproline-containing UAWJ9-36-1 and the dimethylcyclopropylproline-containing UAWJ9-36-3, while the previous study only solved the X-ray crystal structure of the cyclopentylproline-containing analog MI-23.[16] Since UAWJ9-36-3 demonstrated superior antiviral activity than UAWJ9-36-1, the co-crystal structure with UAWJ9-36-3 is valuable in guiding the design of next generation of SARS-CoV-2 M$^{pro}$ inhibitors. 2) we have shown that the cell-based Flip-GFP M$^{pro}$ assay is a viable assay that can be used to predict the cellular antiviral activity of M$^{pro}$ inhibitors in the BSL-2 setting. 3) UAWJ9-36-1 and UAWJ9-36-3 demonstrated broad-spectrum antiviral activity against not only SARS-CoV-2, but also the common human coronaviruses HCoV-OC43, HCoV-NL63, and HCoV-229E. In addition, both UAWJ9-36-1 and UAWJ9-36-3 also had potent enzymatic inhibition against SARS-CoV and MERS-CoV M$^{pro}$s, suggesting they might have antiviral activity against these two viruses. 4) Among the GC-376 analogs reported to date,[10, 14, 16, 34-35] UWAJ9-36-3 has superior cellular antiviral activity. 5) we profiled the selectivity of UAWJ9-36-1 and UAWJ9-36-3 against host cysteine proteases and showed that both compounds had an improved selectivity index than GC-376 against host proteases calpain I and cathepsin L, but not cathepsin K. Although GC-376 analogs such as MI-09, MI-23,[16] and D2-GC-376[17] were reported to have in vivo antiviral efficacy in a SARS-CoV-2 infection mouse model, their target selectivity and potential cytotoxicity have not been systematically studied and their long term side effects are unknown. As all these compounds contain an aldehyde as the reactive warhead, more attention should be given to profiling the selectivity against host cysteine proteases. Only one FDA approved drug voxelotor contains an aldehyde, and many aldehyde-containing drug candidates dropped out clinical trials due to off-target effects.[36]

In summary, results from the hybrid inhibitors designed in this study UAWJ9-36-1 and UAWJ9-36-3, coupled with the in vivo antiviral efficacy from analogs MI-09 and MI-30 reported recently,[16] demonstrated that this series of compounds have great potential to be further developed as broad-spectrum coronavirus antivirals with an improved selectivity index.

MATERIALS AND METHODS

Chemistry.

Chemicals were ordered from commercial sources and were used without further purification. Synthesis procedures for reactions described in FIG. 3 were shown below. All final compounds were purified by flash column chromatography. $^1$H and $^{13}$C NMR spectra were recorded on a Bruker-400 spectrometer. Chemical shifts are reported in parts per million referenced with respect to residual solvent CDCl$_3$ 7.26 ppm from internal standard tetramethylsilane (TMS) 0.00 ppm. The following abbreviations were used in reporting spectra: s, singlet; d, doublet; t, triplet; q, quartet; m, multiplet; dd, doublet of doublets. All reactions were carried out under N$_2$ atmosphere unless otherwise stated. HPLC-grade solvents were used for all reactions. Flash column chromatography was performed using silica gel (230-400 mesh, Merck). Low-resolution mass spectra were obtained using an ESI technique on a 3200 Q Trap LC/MS/MS system (Applied Biosystems). The purity was assessed by using Shimadzu LC-MS with Waters XTerra MS C-18 column (part #186000538), 50×2.1 mm, at a flow rate of 0.3 mL/min; λ=250 and 220 nm; mobile phase A, 0.1% formic acid in H$_2$O, and mobile phase B', 0.1% formic in 60% isopropanol, 30% CH$_3$CN and 9.9% H$_2$O. All compounds submitted for testing were confirmed to be >95.0% purity by LC-MS traces.

The solution of (1S,3aR,6aS)-ethyl octahydrocyclopenta [c] pyrrole-1-carboxylate hydrochloride (1) (5 mmol) and NaHCO$_3$ (12 mmol) in THF/H$_2$O (30 mL, THF/H$_2$O=2:1) was cooled with ice batch and CbzCl (6 mmol) was added. The reaction was stirred until TLC shows complete consumption of the starting material. The mixture was extracted with CH$_2$Cl$_2$. The combined organic layer was separated, dried over anhydrous Na$_2$SO$_4$, filtered and concentrated under reduced pressure. The crude product was used for the next step directly. NMRs showed a diastereomer (dr) mixture was obtained (dr=1:1). $^1$H NMR (400 MHz, CDCl$_3$) δ7.41-7.30 (m, 5H), 5.22-5.01 (m, 2H), 4.26-4.00 (m, 3H), 3.82-3.74 (m, 1H), 3.43, 3.36 (dd, J=10.8, 3.2 Hz, 1H), 2.80-2.62 (m, 2H), 2.05-1.95 (m, 1H), 1.90-1.74 (m, 2H), 1.67-1.45 (m, 3H), 1.29, 1.17 (t, J=7.2 Hz, 3H). $^{13}$C NMR (100 MHz, CDCl$_3$) δ 172.82, 172.67, 155.16, 154.57, 136.76, 136.60, 128.72, 128.58, 128.44, 128.38, 127.90, 127.48, 126.93, 66.96, 65.96, 65.69, 61.01, 60.96, 53.30, 52.78, 49.33, 48.16, 42.47, 41.51, 32.95, 32.84, 32.35, 32.26, 25.53, 14.18, 14.10. C$_{18}$H$_{24}$NO$_4$ ESI-MS: m/z (M+H$^+$): 318.2 (calculated), 318.2 (found).

To the solution of the above crude product in THF/H$_2$O (30 mL, THF/H$_2$O=2:1) at room temperature was added LiOH (7.5 mmol). The reaction was stirred until TLC shows complete consumption of the starting material. After removing THF, the aqueous layer was washed with hexane/ethyl acetate (hexane/ethyl acetate=4:1) and the organic layer was discarded. Then, the aqueous layer was adjusted to slightly acidic pH with 1 N HCl and the mixture was extracted with CH$_2$Cl$_2$/MeOH (CH$_2$Cl$_2$/MeOH=15:1). The combined organic layer was separated, dried over anhydrous Na$_2$SO$_4$, filtered and concentrated under reduced pressure. The obtained acid 2 was pure enough for later steps.

The solution of the acid 2 (1.05 mmol) and the amine salt 3 (1 mmol) in DMF was cooled to 0° C. with ice batch. DIPEA (4 mmol) was added, followed by HCTU (1.1 mmol). The reaction was warmed to room temperature and stirred overnight. The reaction was added brine and extracted with ethyl acetate. The combined organic layer was washed with 1 N HCl, saturated aqueous NaHCO$_3$ and brine successively. Then, the organic layer was dried over anhydrous Na$_2$SO$_4$, filtered and concentrated under reduced pressure. The crude product was used for the next step directly.

The solution of the above crude product in THF (20 mL) was cooled with ice batch. LiBH$_4$ (5 mmol) was added, followed by ethanol (5 mL). The reaction was warmed to room temperature and stirred overnight. After removing THF, the residue was dissolved in water and was adjusted to slightly acidic pH with 1 N HCl and the mixture was extracted with CH$_2$Cl$_2$/MeOH (CH$_2$Cl$_2$/MeOH=15:1). The combined organic layer was separated, dried over anhydrous Na$_2$SO$_4$, filtered and concentrated under reduced pressure. The crude product was used for the next step directly.

The solution of the above crude product in CH$_2$Cl$_2$ (20 mL) was cooled to 0° C. with ice batch. NaHCO$_3$ (1.5 mmol) was added, followed by Dess-Martin Periodinane (DMP) (1.5 mmol). The reaction was warmed to room temperature and stirred until TLC shows complete consumption of the starting material. The reaction was quenched with saturated aqueous Na$_2$S$_2$O$_3$, followed by saturated aqueous NaHCO$_3$. The mixture was extracted with CH$_2$Cl$_2$/MeOH (CH$_2$Cl$_2$/MeOH=15:1). The combined organic layer was separated, dried over anhydrous Na$_2$SO$_4$, filtered and concentrated under reduced pressure. The residue was purified by silica gel flash column chromatography (CH$_2$C$_2$ to CH$_2$C$_2$/MeOH=15:1) to afford the target product UAWJ9-36-1.

UAWJ9-36-1 Yield: 58% from the carboxylic acid 2. $^1$H NMR (400 MHz, CDCl$_3$, isomers) δ δ 9.53, 9.19 (s, 1H), 8.52, 8.13 (s, 1H), 7.35 (m, 5H), 6.24, 6.02 (s, 1H), 5.31-4.97 (m, 2H), 4.51-4.02 (m, 2H), 3.89-3.69 (m, 1H), 3.47-3.23 (m, 3H), 2.85-2.65 (m, 2H), 2.57-2.12 (m, 2H), 2.12-1.91 (m, 2H), 1.90-1.78 (m, 4H), 1.70-1.58 (m, 2H), 1.56-1.44 (m, 1H). $^{13}$C NMR (100 MHz, CDCl$_3$, isomers) δ 200.11, 199.86, 180.06), 173.99, 173.50, 155.41, 154.73, 136.67, 128.54, 128.45, 127.96, 127.83, 127.79, 67.35-66.77 (m), 58.24, 57.81, 55.08, 53.29-52.96 (m), 50.11, 50.07, 48.23, 48.18, 42.70, 42.63, 41.74, 41.66, 40.60, 40.46, 38.51, 38.05, 32.59, 32.55, 31.84, 31.53, 29.70, 29.60, 28.98, 28.82, 25.41, 25.26. C$_{23}$H$_{30}$N$_3$O$_5$ ESI-MS: m/z (M+H$^+$): 428.2 (calculated), 428.2 (found).

UAWJ9-36-3 was synthesized using the same procedure described above. The installation of Cbz also afforded dr mixture (dr=1:1). $^1$H NMR (400 MHz, CDCl$_3$) δ 7.39-7.26 (m, 5H), 5.24-4.97 (m, 2H), 3.77, 3.62 (s, 3H), 3.76-3.72 (m, 1H), 3.55, 3.52 (d, J=10.8 Hz, 1H), 1.90-1.81 (m, 1H), 1.46-1.39 (m, 2H), 1.05 (s, 3H), 0.98, 0.98 (s, 3H). $^{13}$C NMR (100 MHz, CDCl$_3$) δ 172.67, 1172.52, 154.20, 153.63, 136.68, 136.58, 128.71, 128.56, 127.91, 127.63, 127.59, 66.98, 66.92, 59.88, 59.54, 52.31, 52.17, 46.89, 46.34, 32.04, 31.07, 27.32, 26.49, 26.26, 26.24, 19.41, 19.36, 12.55. $C_{17}H_{22}NO_4$ ESI-MS: m/z (M+H$^+$): 304.2 (calculated), 304.2 (found).

UAWJ9-36-3 Yield: 52% from the carboxylic acid 5. $^1$H NMR (400 MHz, CDCl$_3$, isomers) δ 9.53, 9.14, (s, 1H) 8.67, 8.20 (d, J=4.0 Hz, 1H), 7.41-7.28 (m, 5H), 6.35-5.90 (m, 1H), 5.36-4.93 (m, 2H), 4.45-4.07 (m, 2H), 3.89-3.71 (m, 1H), 3.71-3.16 (m, 4H), 2.54-1.78 (m, 5H), 1.62-1.36 (m, 2H), 1.07 (s, 3H), 0.96, 0.94 (s, 3H). $^{13}$C NMR (100 MHz, CDCl$_3$, isomers) δ 200.15, 199.84, 180.09, 180.07, 173.49, 172.88, 154.54, 153.93, 136.65, 136.58, 128.57, 12845, 128.44, 128.04, 127.99, 127.95, 127.58, 98.46 (hemiacetal), 67.47, 67.12, 67.04, 61.44, 61.40, 58.48, 57.92, 55.17, 53.07, 50.83, 47.25, 46.83, 40.72, 40.57, 38.67, 38.08, 32.96, 31.50, 29.79, 29.55, 29.07, 28.83, 27.44, 27.36, 26.31, 26.23, 26.15, 25.96, 19.32, 19.20, 12.62, 12.58. $C_{23}H_{30}N_3O_5$ ESI-MS: m/z (M+H$^+$): 428.2 (calculated), 428.2 (found).

Cell Lines and Viruses

Human rhabdomyosarcoma (RD, ATCC® CCL-136™), Vero C1008 (ATCC® CRL-1586™), Huh-7 (a kind gift from Dr. Tianyi Wang at University of Pittsburgh), and HEK293T expressing ACE2 (293T-ACE2, BEI Resources, NR-52511) cell lines were maintained in Dulbecco's modified eagle's medium (DMEM); Human fibroblast Cell Line, MRC-5 (ATCC® CCL-171™) was maintained in eagle's minimum essential medium (EMEM, ATCC® 30-2003™). Both media were supplemented with 10% fetal bovine serum (FBS) and 1% penicillin-streptomycin antibiotics. Cells were kept at cell culture incubator (humidified, 5% $CO_2$/95% air, 37° C.). The following reagents were obtained through BEI Resources, NIAID, NIH: human coronavirus, OC43, NR-52725; human coronavirus, NL63, NR-470. HCoV-OC43 was propagated in RD cell line; HCoV-NL63 was initially propagated in 293T-ACE2 cell line and accommodated in Vero E6 cell line. HCoV-229E was obtained from Dr. Bart Tarbet (Utah State University) and amplified in Huh-7 or MRC-5 cell lines.

Protein Expression and Purification

The genes encoding SARS-CoV-2 main protease (Accession No.: 7BUY_A), SARS-CoV main protease (Accession No.: 6W79_A), MERS-CoV main protease (Accession No.: 5C3N_B), HCoV-229E main protease (Accession No.: P0C6X1), HCoV-OC43 main protease (Accession No.: QDH43723), HCoV-NL63 main protease (Accession No.: 5GWY_A), HCoV-HKU1 main protease (Accession No.: 3D23_D) were purchased from GenScript (Piscataway, NJ) with *E. Coli* codon optimization and inserted into pET29a(+) plasmid. The M$^{pro}$ genes were then subcloned into pE-SUMO plasmid as previously described.[10] The expression and purification of all MP's followed the same procedures as previously described.[32] Cathepsin K (Catlog #219461) and Cathepsin L (Catalog #219402) were purchased from EMD Millipore, Calpain I (Catalog #C6108) and trypsin (Cataloxy #T6763) were purchased from Sigma-Aldrich, and Caspas-3 (Catalog #1083-25) was purchased from BioVision (Milpitas, CA).

Differential Scanning Fluorimetry (DSF)

Direct binding of GC-376, UAWJ9-36-1 and UAWJ9-36-3 with SARS-CoV-2, SARS-CoV, MERS-CoV, HCoV-OC43, HCoV-229E, HCoV-NL63, HCoV-HKU1 M$^{pro}$s was detected by differential scanning fluorimetry (DSF) using a Thermal Fisher QuantStudio 5 Real-Time PCR System as previously described[32] with minor modifications. M$^{pro}$s were diluted in a buffer containing 20 mM HEPES, pH 6.5, 120 mM NaCl, 0.4 mM EDTA, 4 mM DTT, and 20% glycerol to a final concentration of 4 µM and incubated with serial concentrations of compounds (0.06-200 µM) at 30° C. for 1 hr. DMSO was included as a reference. 1×SYPRO orange (Thermal Fisher, Cat. #: S6650) was added and the fluorescence signal was recorded under a temperature gradient ranging from 20 to 95° C. (incremental step of 0.05° C. s$^{-1}$). The melting temperature ($T_m$) was calculated as the mid log of the transition phase from the native to the denatured protein using a Boltzmann model in Protein Thermal Shift Software v1.3. $\Delta T_m$ was calculated by subtracting reference melting temperature of proteins in the presence of DMSO from the $T_m$ in the presence of compounds.

Enzymatic Assays

To determine IC$_{50}$ values for GC-376, UAWJ9-36-1 and UAWJ9-36-3, 100 nM SARS-CoV-2, MERS-CoV, SARS-CoV, HCoV-OC43, HCoV-229E, HCoV-NL63, or HCoV-HKU1 M$^{pro}$ was incubated with serial concentrations of the compounds at 30° C. for 30 min in the reaction buffer containing 20 mM HEPES, pH 6.5, 120 mM NaCl, 0.4 mM EDTA, 4 mM DTT, and 20% glycerol. The proteolytic reactions were initiated by adding 10 µM of substrate peptide and recorded in Cytation 5 imaging reader (Thermo Fisher Scientific) with filters for excitation at 360/40 nm and emission at 460/40 nm for 1 hr. The initial velocity of the proteolytic reaction was calculated by linear regression for the first 15 min of the kinetic progress curves. IC$_{50}$ curve fittings were performed using log (concentration of compounds) vs the initial velocity with variable slopes in Prism 8.

Kinetic studies of the proteolytic reaction progress curves with GC-376, UAWJ9-36-1 and UAWJ9-36-3 were carried out as follows: 5 nM SARS-CoV-2 M$^{pro}$, 60 nM MERS-CoV M$^{pro}$ or 5 nM SARS-CoV M$^{pro}$ was added into 20 µM substrate peptide pre-mixed with serial concentrations of the compounds in 200 µl of reaction buffer at 30° C. to initiate the proteolytic reaction. The reaction was monitored for 4 hr. The progression curves were fitted as previously described.[32] The first 90 min of the kinetic curves were used in the curve fittings as substrate depletion was observed when proteolytic reactions carried out longer than 90 min.

Trypsin assay reactions were carried out as previously described,[33] with minor modifications. 100 µl reaction solution containing 100 nM Trypsin (Millipore sigma, Cat. No.: T6763), 50 mM HEPES (pH7.6), and serial concentrations of GC-376, UAWJ9-36-1 and UAWJ9-36-3 (0, 0.02, 0.06, 0.2, 0.6, 2, 6, 20 µM) or Camostat (0, 0.002, 0.006, 0.02, 0.06, 0.2, 0.6, 2 µM) were incubated at 30° C. for 30 mins. The reactions were initiated by adding 100 µM Bz-Arg-AMC·HCl(BACHEM, Product No.: 4002540.0050). Fluorescence signal intensities were recorded for 20 mins using a Biotek Cytation™ 3 plate reader (Thermo Fisher Scientific) with filters for excitation at 360/40 nm and emission at 460/40 nm, and the initial velocity was calculated for the first 10 min by linear regression. The IC$_{50}$ s were determined by curve fittings using log (concentration of compounds) vs the initial velocity with variable slopes in Prism 8.

Calpain I, Cathepsin L and Cathepsin K enzymatic assays were carried as previously described.[33]

Caspase-3 enzymatic assay was carried out as follows: 1 unit Caspase-3 protein was diluted into 1600 µl reaction buffer (20 mM HEPES pH7.4, 2 mM EDTA, 0.1% CHAPS and 5 mM DTT); 100 µl diluted protein was incubated with 1 µl various concentration of testing compounds for 30 min at 30° C.; the enzymatic reaction was initiated by adding 1 µl of 2 mM Ac-DEVD-AFC (Medchemexpress, Catalog #HY-P1005). The reaction was monitored a Molecular Devices SpectraMax iD3 plate reader with excitation at 400 nm and emission at 505 nm at 30° C. for 1 hour. The $IC_{50}$ values were calculated as described in the previous section.

Cellular Based FlipGFP $M^{pro}$ Assay

Plasmid pcDNA3-TEV-flipGFP-T2A-mCherry was purchased from Addgene (Cat #124429). SARS-CoV-2 $M^{pro}$ cleavage site (AVLQSGFR) and SARS-CoV-2 $PL^{pro}$ cleavage site (LRGGAPTK) were introduced into pcDNA3-flipGFP-T2A-mCherry via overlapping PCRs to generate a fragment with SacI and HindIII sites at the ends. SARS-CoV-2 $M^{pro}$ and $PL^{pro}$ expression plasmids pcDNA3.1 SARS-CoV-2 $M^{pro}$ and pcDNA3.1 SARS-CoV-2 $PL^{pro}$ was ordered from Genscript (Piscataway NJ) with codon optimization. pcDNA3.1 SARS-CoV-2 $M^{pro}$-C145A was generated by site-directed Quikchange mutagenesis.

293T cells were seeded in 96-well black, clear bottom Greiner plate (catalog #655090) and reached 70 to 90% confluency overnight. 50 ng pcDNA3-flipGFP-T2A-mCherry plasmid with TEV, $PL^{pro}$ or $M^{pro}$ cleavage site and 50 ng protease expression plasmid pcDNA3.1 SARS-CoV-2 $M^{pro}$ or SARS-CoV-2 $PL^{pro}$ was transfected into 293T cells with transfection reagent TransIT-293 (Mirus Catalog #MIR 2700) according to the manufacturer protocol. 3 hrs after transfection, 1 µl testing compound was added to each well at 100-fold dilution. 2 days after transfection, Images were taken with Cytation 5 imaging reader (Biotek) GFP and mCherry channels via 10× objective lens; and were analyzed with Gen5 3.10 software (Biotek). SARS-CoV-2 $M^{pro}$ protease activity was assessed by the ratio of GFP signal sum intensity over mCherry signal sum intensity. Testing compounds efficacy ($IC_{50}$) in cells was calculated by plotting GFP/mCherry signal over the applied compound concentration with a 4 parameters dose-response function in prism 8. The mCherry signal alone in the presence of testing compounds was utilized to evaluate the compound cytotoxicity.

Antiviral Assays

The antiviral activity of GC-376, UAWJ9-36-1 and UAWJ9-36-3 against HCoV-229E and HCoV-NL63 was detected in CPE assay as previously described.[32,37] Briefly, near confluent MRC-5 cells and Vero C1008 cells in 96-well plates were infected with 100 µl of HCoV-229E and HCoV-NL63 at desired dilutions and incubated at 33 or 37° C. for 1 h. Different concentrations of testing compounds (0, 0.015, 0.05, 0.15, 0.5, 1.5, 3, 5,15 µM) were added and the infected cells were incubated for another 3 to 5 days until significant cytopathic effect was observed in the wells without compound (virus only). Growth medium was removed and cells were stained with 0.1 mg/mL neutral red for 2 h and excess dye was rinsed from the cells with PBS. The uptaken neutral red dye was extracted from the cells with a buffer containing 50% ethanol and 1% glacial acetic acid. The absorbance of neutral red dye at 540 nm was measured on a spectrometer. The antiviral activity of GC-376, UAWJ9-36-1 and UAWJ9-36-3 was tested against HCoV-OC43 in plaque assay. RD cells were infected with HCoV-OC43 and incubated at 33° C. for 1 h to allow virus adsorption. The viral inoculum was removed and an overlay containing 0.2% Avicel supplemented with 2% FBS in DMEM containing serial concentrations of testing compounds (0, 0.001, 0.003, 0.01, 0.03, 0.1, 0.3, 1 µM) was added and incubated in the 33° C. incubator for 4 to 5 days. The plaque formation was detected by staining the cell monolayer with crystal violet and the plaque areas were quantified using Image J. $EC_{50}$ values were determined by plotting percent CPE versus $\log_{10}$ compound concentrations from best-fit dose response curves with variable slope in Prism 8.

SARS-CoV-2 $M^{pro}$ Crystallization and Structure Determination

SARS-CoV-2 $M^{pro}$ and HM-$M^{pro}$ protein was purified and crystals were grown as previously described.[9-10] X-ray diffraction data was collected on the Structural Biology Center 19-ID beamline at the Advanced Photon Source in Argonne, IL and processed with the iMosflm. The CCP4 version of MOLREP was used to solve the structure of UAWJ9-36-1+SARS-CoV-2 $M^{pro}$ using 7KX5 as a reference model and UAWJ9-36-3+SARS-CoV-2 HM-$M^{pro}$ with 6XBI as a reference model. Structures were then refined with REFMACS and built with COOT.[38-39] All protein structure figures were generated with PyMOL (Schrödinger LLC).

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

INCORPORATION BY REFERENCE

The entire disclosure of each of the patent documents and scientific articles referred to herein is incorporated by reference for all purposes. The following references, identified numerically throughout the application, are incorporated by reference:

1. Petersen, E.; Koopmans, M.; Go, U.; Hamer, D. H.; Petrosillo, N.; Castelli, F.; Storgaard, M.; Al Khalili, S.; Simonsen, L., Comparing SARS-CoV-2 with SARS-CoV and influenza pandemics. *Lancet Infect Dis* 2020, 20 (9), e238-e244.
2. Morse, J. S.; Lalonde, T.; Xu, S.; Liu, W. R., Learning from the Past: Possible Urgent Prevention and Treatment Options for Severe Acute Respiratory Infections Caused by 2019-nCoV. *Chembiochem* 2020, 21 (5), 730-738.
3. Beigel, J. H.; Tomashek, K. M.; Dodd, L. E.; Mehta, A. K.; Zingman, B. S.; Kalil, A. C.; Hohmann, E.; Chu, H. Y.; Luetkemeyer, A.; Kline, S.; Lopez de Castilla, D.; Finberg, R. W.; Dierberg, K.; Tapson, V.; Hsieh, L.; Patterson, T. F.; Paredes, R.; Sweeney, D. A.; Short, W. R.; Touloumi, G.; Lye, D. C.; Ohmagari, N.; Oh, M. D.; Ruiz-Palacios, G. M.; Benfield, T.; Fatkenheuer, G.; Kortepeter, M. G.; Atmar, R. L.; Creech, C. B.; Lundgren, J.; Babiker, A. G.; Pett, S.; Neaton, J. D.; Burgess, T. H.; Bonnett, T.; Green, M.; Makowski, M.; Osinusi, A.; Nayak, S.; Lane, H. C.; Members, A.-S. G., Remdesivir for the Treatment of Covid-19—Final Report. *N Engl J Med* 2020, 383 (19), 1813-1826.
4. Spinner, C. D.; Gottlieb, R. L.; Criner, G. J.; Arribas López, J. R.; Cattelan, A. M.; Soriano Viladomiu, A.; Ogbuagu, O.; Malhotra, P.; Mullane, K. M.; Castagna, A.; Chai, L. Y. A.; Roestenberg, M.; Tsang, O. T. Y.; Bernasconi, E.; Le Turnier, P.; Chang, S.-C.; SenGupta, D.; Hyland, R. H.; Osinusi, A. O.; Cao, H.; Blair, C.; Wang, H.; Gaggar, A.; Brainard, D. M.; McPhail, M. J.; Bhagani, S.; Ahn, M. Y.; Sanyal, A. J.; Huhn, G.; Marty, F. M.; Investigators, f. t. G.-U.-.-. Effect of Remdesivir vs Standard Care on Clinical Status at 11 Days in Patients With Moderate COVID-19: A Randomized Clinical Trial. *JAMA* 2020, 324 (11), 1048-1057.

5. Consortium, W. H. O. S. T.; Pan, H.; Peto, R.; Henao-Restrepo, A. M.; Preziosi, M. P.; Sathiyamoorthy, V.; Abdool Karim, Q.; Alejandria, M. M.; Hernandez Garcia, C.; Kieny, M. P.; Malekzadeh, R.; Murthy, S.; Reddy, K. S.; Roses Periago, M.; Abi Hanna, P.; Ader, F.; Al-Bader, A. M.; Alhasawi, A.; Allum, E.; Alotaibi, A.; Alvarez-Moreno, C. A.; Appadoo, S.; Asiri, A.; Aukrust, P.; Barratt-Due, A.; Bellani, S.; Branca, M.; Cappel-Porter, H. B. C.; Cerrato, N.; Chow, T. S.; Como, N.; Eustace, J.; Garcia, P. J.; Godbole, S.; Gotuzzo, E.; Griskevicius, L.; Hamra, R.; Hassan, M.; Hassany, M.; Hutton, D.; Irmansyah, I.; Jancoriene, L.; Kirwan, J.; Kumar, S.; Lennon, P.; Lopardo, G.; Lydon, P.; Magrini, N.; Maguire, T.; Manevska, S.; Manuel, O.; McGinty, S.; Medina, M. T.; Mesa Rubio, M. L.; Miranda-Montoya, M. C.; Nel, J.; Nunes, E. P.; Perola, M.; Portoles, A.; Rasmin, M. R.; Raza, A.; Rees, H.; Reges, P. P. S.; Rogers, C. A.; Salami, K.; Salvadori, M. I.; Sinani, N.; Sterne, J. A. C.; Stevanovikj, M.; Tacconelli, E.; Tikkinen, K. A. O.; Trelle, S.; Zaid, H.; Rottingen, J. A.; Swaminathan, S., Repurposed Antiviral Drugs for Covid-19-Interim WHO Solidarity Trial Results. *N Engl J Med* 2021, 384 (6), 497-511.

6. Sheahan, T. P.; Sims, A. C.; Zhou, S.; Graham, R. L.; Pruijssers, A. J.; Agostini, M. L.; Leist, S. R.; Schafer, A.; Dinnon, K. H., 3rd; Stevens, L. J.; Chappell, J. D.; Lu, X.; Hughes, T. M.; George, A. S.; Hill, C. S.; Montgomery, S. A.; Brown, A. J.; Bluemling, G. R.; Natchus, M. G.; Saindane, M.; Kolykhalov, A. A.; Painter, G.; Harcourt, J.; Tamin, A.; Thornburg, N. J.; Swanstrom, R.; Denison, M. R.; Baric, R. S., An orally bioavailable broad-spectrum antiviral inhibits SARS-CoV-2 in human airway epithelial cell cultures and multiple coronaviruses in mice. *Sci Transl Med* 2020, 12 (541), eabb5883.

7. Cox, R. M.; Wolf, J. D.; Plemper, R. K., Therapeutically administered ribonucleoside analogue MK-4482/EIDD-2801 blocks SARS-CoV-2 transmission in ferrets. *Nat Microbiol* 2021, 6 (1), 11-18.

8. Toots, M.; Yoon, J.-J.; Cox, R. M.; Hart, M.; Sticher, Z. M.; Makhsous, N.; Plesker, R.; Barrena, A. H.; Reddy, P. G.; Mitchell, D. G.; Shean, R. C.; Bluemling, G. R.; Kolykhalov, A. A.; Greninger, A. L.; Natchus, M. G.; Painter, G. R.; Plemper, R. K., Characterization of orally efficacious influenza drug with high resistance barrier in ferrets and human airway epithelia. *Sci Transl Med* 2019, 11 (515), eaax5866.

9. Ma, C.; Sacco, M. D.; Hurst, B.; Townsend, J. A.; Hu, Y.; Szeto, T.; Zhang, X.; Tarbet, B.; Marty, M. T.; Chen, Y.; Wang, J., Boceprevir, GC-376, and calpain inhibitors II, XII inhibit SARS-CoV-2 viral replication by targeting the viral main protease. *Cell Res* 2020, 30 (8), 678-692.

10. Sacco, M. D.; Ma, C.; Lagarias, P.; Gao, A.; Townsend, J. A.; Meng, X.; Dube, P.; Zhang, X.; Hu, Y.; Kitamura, N.; Hurst, B.; Tarbet, B.; Marty, M. T.; Kolocouris, A.; Xiang, Y.; Chen, Y.; Wang, J., Structure and inhibition of the SARS-CoV-2 main protease reveal strategy for developing dual inhibitors against M(pro) and cathepsin L. *Sci Adv* 2020, 6 (50), eabe0751.

11. Freitas, B. T.; Durie, I. A.; Murray, J.; Longo, J. E.; Miller, H. C.; Crich, D.; Hogan, R. J.; Tripp, R. A.; Pegan, S. D., Characterization and Noncovalent Inhibition of the Deubiquitinase and deISGylase Activity of SARS-CoV-2 Papain-Like Protease. *ACS Infect Dis* 2020, 6 (8), 2099-2109.

12. Shin, D.; Mukherjee, R.; Grewe, D.; Bojkova, D.; Baek, K.; Bhattacharya, A.; Schulz, L.; Widera, M.; Mehdipour, A. R.; Tascher, G.; Geurink, P. P.; Wilhelm, A.; van der Heden van Noort, G. J.; Ovaa, H.; Müller, S.; Knobeloch, K.-P.; Rajalingam, K.; Schulman, B. A.; Cinatl, J.; Hummer, G.; Ciesek, S.; Dikic, I., Papain-like protease regulates SARS-CoV-2 viral spread and innate immunity. *Nature* 2020, 587 (7835), 657-662.

13. Klemm, T.; Ebert, G.; Calleja, D. J.; Allison, C. C.; Richardson, L. W.; Bernardini, J. P.; Lu, B. G.; Kuchel, N. W.; Grohmann, C.; Shibata, Y.; Gan, Z. Y.; Cooney, J. P.; Doerflinger, M.; Au, A. E.; Blackmore, T. R.; van der Heden van Noort, G. J.; Geurink, P. P.; Ovaa, H.; Newman, J.; Riboldi-Tunnicliffe, A.; Czabotar, P. E.; Mitchell, J. P.; Feltham, R.; Lechtenberg, B. C.; Lowes, K. N.; Dewson, G.; Pellegrini, M.; Lessene, G.; Komander, D., Mechanism and inhibition of the papain-like protease, PLpro, of SARS-CoV-2. *EMBO J* 2020, 39 (18), e106275.

14. Rathnayake, A. D.; Zheng, J.; Kim, Y.; Perera, K. D.; Mackin, S.; Meyerholz, D. K.; Kashipathy, M. M.; Battaile, K. P.; Lovell, S.; Perlman, S.; Groutas, W. C.; Chang, K. O., 3C-like protease inhibitors block coronavirus replication in vitro and improve survival in MERS-CoV-infected mice. *Sci Transl Med* 2020, 12 (557), eabc5332.

15. Boras, B.; Jones, R. M.; Anson, B. J.; Arenson, D.; Aschenbrenner, L.; Bakowski, M. A.; Beutler, N.; Binder, J.; Chen, E.; Eng, H.; Hammond, J.; Hoffman, R.; Kadar, E. P.; Kania, R.; Kimoto, E.; Kirkpatrick, M. G.; Lanyon, L.; Lendy, E. K.; Lillis, J. R.; Luthra, S. A.; Ma, C.; Noell, S.; Obach, R. S.; O'Brien, M. N.; O'Connor, R.; Ogilvie, K.; Owen, D.; Pettersson, M.; Reese, M. R.; Rogers, T.; Rossulek, M. I.; Sathish, J. G.; Steppan, C.; Ticehurst, M.; Updyke, L. W.; Zhu, Y.; Wang, J.; Chatterjee, A. K.; Mesecar, A. D.; Anderson, A. S.; Allerton, C., Discovery of a Novel Inhibitor of Coronavirus 3CL Protease as a Clinical Candidate for the Potential Treatment of COVID-19. *bioRxiv* 2020, 2020.09.12.293498.

16. Qiao, J.; Li, Y. S.; Zeng, R.; Liu, F. L.; Luo, R. H.; Huang, C.; Wang, Y. F.; Zhang, J.; Quan, B.; Shen, C.; Mao, X.; Liu, X.; Sun, W.; Yang, W.; Ni, X.; Wang, K.; Xu, L.; Duan, Z. L.; Zou, Q. C.; Zhang, H. L.; Qu, W.; Long, Y. H.; Li, M. H.; Yang, R. C.; Liu, X.; You, J.; Zhou, Y.; Yao, R.; Li, W. P.; Liu, J. M.; Chen, P.; Liu, Y.; Lin, G. F.; Yang, X.; Zou, J.; Li, L.; Hu, Y.; Lu, G. W.; Li, W. M.; Wei, Y. Q.; Zheng, Y. T.; Lei, J.; Yang, S., SARS-CoV-2 M(pro) inhibitors with antiviral activity in a transgenic mouse model. *Science* 2021, 371, 1374-1378.

17. Dampalla, C. S.; Zhang, J.; Perera, K. D.; Wong, L.-Y. R.; Meyerholz, D. K.; Nguyen, H. N.; Kashipathy, M. M.; Battaile, K. P.; Lovell, S.; Kim, Y.; Perlman, S.; Groutas, W. C.; Chang, K.-O., Post-infection treatment with a protease inhibitor increases survival of mice with a fatal SARS-CoV-2 infection. *bioRxiv* 2021, 2021.02.05.429937.

18. Pedersen, N. C.; Kim, Y.; Liu, H.; Galasiti Kankanamalage, A. C.; Eckstrand, C.; Groutas, W. C.; Bannasch, M.; Meadows, J. M.; Chang, K. O., Efficacy of a 3C-like protease inhibitor in treating various forms of acquired feline infectious peritonitis. *J Feline Med Surg* 2018, 20 (4), 378-392.

19. Kim, Y.; Liu, H.; Galasiti Kankanamalage, A. C.; Weerasekara, S.; Hua, D. H.; Groutas, W. C.; Chang, K. O.; Pedersen, N. C., Reversal of the Progression of Fatal Coronavirus Infection in Cats by a Broad-Spectrum Coronavirus Protease Inhibitor. *PLoS Pathog* 2016, 12 (3), e1005531.
20. Fu, L.; Ye, F.; Feng, Y.; Yu, F.; Wang, Q.; Wu, Y.; Zhao, C.; Sun, H.; Huang, B.; Niu, P.; Song, H.; Shi, Y.; Li, X.; Tan, W.; Qi, J.; Gao, G. F., Both Boceprevir and GC376 efficaciously inhibit SARS-CoV-2 by targeting its main protease. *Nat Commun* 2020, 11 (1), 4417.
21. Vuong, W.; Khan, M. B.; Fischer, C.; Arutyunova, E.; Lamer, T.; Shields, J.; Saffran, H. A.; McKay, R. T.; van Belkum, M. J.; Joyce, M. A.; Young, H. S.; Tyrrell, D. L.; Vederas, J. C.; Lemieux, M. J., Feline coronavirus drug inhibits the main protease of SARS-CoV-2 and blocks virus replication. *Nat Commun* 2020, 11 (1), 4282.
22. Kneller, D. W.; Galanie, S.; Phillips, G.; O'Neill, H. M.; Coates, L.; Kovalevsky, A., Malleability of the SARS-CoV-2 3CL Mpro Active-Site Cavity Facilitates Binding of Clinical Antivirals. *Structure* 2020, 28 (12), 1313-1320.e3.
23. Steuten, K.; Kim, H.; Widen, J. C.; Babin, B. M.; Onguka, O.; Lovell, S.; Bolgi, O.; Cerikan, B.; Neufeldt, C. J.; Cortese, M.; Muir, R. K.; Bennett, J. M.; Geiss-Friedlander, R.; Peters, C.; Bartenschlager, R.; Bogyo, M., Challenges for Targeting SARS-CoV-2 Proteases as a Therapeutic Strategy for COVID-19. *ACS Infect Dis* 2021.
24. Ma, C.; Hu, Y.; Townsend, J. A.; Lagarias, P. I.; Marty, M. T.; Kolocouris, A.; Wang, J., Ebselen, Disulfiram, Carmofur, PX-12, Tideglusib, and Shikonin Are Nonspecific Promiscuous SARS-CoV-2 Main Protease Inhibitors. *ACS Pharmacol Transl Sci* 2020, 3 (6), 1265-1277.
25. Ma, C.; Wang, J., Dipyridamole, chloroquine, montelukast sodium, candesartan, oxytetracycline, and atazanavir are not SARS-CoV-2 main protease inhibitors. *Proc Natl Acad Sci USA* 2021, 118 (8), e2024420118.
26. Li, X.; Lidsky, P.; Xiao, Y.; Wu, C.-T.; Garcia-Knight, M.; Yang, J.; Nakayama, T.; Nayak, J. V.; Jackson, P. K.; Andino, R.; Shu, X., Ethacridine inhibits SARS-CoV-2 by inactivating viral particles in cellular models. *bioRxiv* 2020, 2020.10.28.359042.
27. Froggatt, H. M.; Heaton, B. E.; Heaton, N. S., Development of a Fluorescence-Based, High-Throughput SARS-CoV-2 3CLpro Reporter Assay. *J Virol* 2020, 94 (22), e01265-20.
28. Hoffmann, M.; Kleine-Weber, H.; Schroeder, S.; Kruger, N.; Herrler, T.; Erichsen, S.; Schiergens, T. S.; Herrler, G.; Wu, N. H.; Nitsche, A.; Muller, M. A.; Drosten, C.; Pohlmann, S., SARS-CoV-2 Cell Entry Depends on ACE2 and TMPRSS2 and Is Blocked by a Clinically Proven Protease Inhibitor. *Cell* 2020, 181 (2), 271-280 e8.
29. Bertram, S.; Glowacka, I.; Blazejewska, P.; Soilleux, E.; Allen, P.; Danisch, S.; Steffen, I.; Choi, S. Y.; Park, Y.; Schneider, H.; Schughart, K.; Pohlmann, S., TMPRSS2 and TMPRSS4 facilitate trypsin-independent spread of influenza virus in Caco-2 cells. *J Virol* 2010, 84 (19), 10016-25.
30. Stanifer, M. L.; Kee, C.; Cortese, M.; Zumaran, C. M.; Triana, S.; Mukenhim, M.; Kraeusslich, H. G.; Alexandrov, T.; Bartenschlager, R.; Boulant, S., Critical Role of Type III Interferon in Controlling SARS-CoV-2 Infection in Human Intestinal Epithelial Cells. *Cell Rep* 2020, 32 (1), 107863.
31. De Rosa, M. F.; Sillence, D.; Ackerley, C.; Lingwood, C., Role of multiple drug resistance protein 1 in neutral but not acidic glycosphingolipid biosynthesis. *J Biol Chem* 2004, 279 (9), 7867-76.
32. Hu, Y.; Ma, C.; Szeto, T.; Hurst, B.; Tarbet, B.; Wang, J., Boceprevir, Calpain Inhibitors II and XII, and GC-376 Have Broad-Spectrum Antiviral Activity against Coronaviruses. *ACS Infect Dis* 2021, 7 (3), 586-597.
33. Naoya Kitamura; Michael Dominic Sacco; Chunlong Ma; Yanmei Hu; Julia Alma Townsend; Xiangzhi Meng; Fushun Zhang; Xiujun Zhang; Adis Kukuljac; Michael Thomas Marty; David; Schultz; Sara Cherry; Yan Xiang; Yu Chen, J. W., An expedited approach towards the rationale design of non-covalent SARS-CoV-2 main protease inhibitors with in vitro antiviral activity *bioRxiv* 2021, 2020.12.19.423537.
34. Vatansever, E. C.; Yang, K. S.; Drelich, A. K.; Kratch, K. C.; Cho, C.-C.; Kempaiah, K. R.; Hsu, J. C.; Mellott, D. M.; Xu, S.; Tseng, C.-T. K.; Liu, W. R., Bepridil is potent against SARS-CoV-2 in vitro. *Proc Natl Acad Sci USA* 2021, 118 (10), e2012201118.
35. Zhang, L.; Lin, D.; Kusov, Y.; Nian, Y.; Ma, Q.; Wang, J.; von Brunn, A.; Leyssen, P.; Lanko, K.; Neyts, J.; de Wilde, A.; Snijder, E. J.; Liu, H.; Hilgenfeld, R., alpha-Ketoamides as Broad-Spectrum Inhibitors of Coronavirus and Enterovirus Replication: Structure-Based Design, Synthesis, and Activity Assessment. *J Med Chem* 2020, 63 (9), 4562-4578.
36. Siklos, M.; BenAissa, M.; Thatcher, G. R. J., Cysteine proteases as therapeutic targets: does selectivity matter? A systematic review of calpain and cathepsin inhibitors. *Acta Pharm Sin B* 2015, 5 (6), 506-519.
37. Hu, Y.; Meng, X.; Zhang, F.; Xiang, Y.; Wang, J., The in vitro antiviral activity of lactoferrin against common human coronaviruses and SARS-CoV-2 is mediated by targeting the heparan sulfate co-receptor. *Emerg Microbes Infect* 2021, 10, 317-330.
38. Murshudov, G. N.; Skubak, P.; Lebedev, A. A.; Pannu, N. S.; Steiner, R. A.; Nicholls, R. A.; Winn, M. D.; Long, F.; Vagin, A. A., REFMACS for the refinement of macromolecular crystal structures. *Acta Crystallogr D* 2011, 67, 355-367.
39. Emsley, P.; Cowtan, K., Coot: model-building tools for molecular graphics. *Acta Crystallogr D* 2004, 60, 2126-2132.

SEQUENCE LISTING

<160> NUMBER OF SEQ ID NOS: 1

<210> SEQ ID NO 1
<211> LENGTH: 130
<212> TYPE: PRT
<213> ORGANISM: Artificial sequence
<220> FEATURE:
<223> OTHER INFORMATION: synthetic

<400> SEQUENCE: 1

| | | | | | | | | | | | | |
|---|---|---|---|---|---|---|---|---|---|---|---|---|
| Met<br>1 | Asp | Leu | Pro | Asp<br>5 | Asp | His | Tyr | Leu | Ser<br>10 | Thr | Gln | Thr | Ile | Leu<br>15 | Ser |
| Lys | Asp | Leu | Asn<br>20 | Ser | Gly | Leu | Arg | Ser<br>25 | Gly | Ser | Gly | Leu | Glu<br>30 | Met | Glu |
| Val | Ser | Ala<br>35 | Leu | Glu | Lys | Glu | Val<br>40 | Ser | Ala | Leu | Glu | Lys<br>45 | Glu | Val | Ser |
| Ala | Leu<br>50 | Glu | Lys | Glu | Val | Ser<br>55 | Ala | Leu | Glu | Lys | Glu<br>60 | Val | Ser | Ala | Leu |
| Glu<br>65 | Lys | Glu | Lys | Arg | Asp<br>70 | His | Met | Val | Leu | Leu<br>75 | Glu | Tyr | Val | Thr | Ala<br>80 |
| Ala | Gly | Ile | Thr | Asp<br>85 | Ala | Ser | Ala | Val | Leu<br>90 | Gln | Ser | Gly | Phe | Arg<br>95 | Lys |
| Val | Ser | Ala | Leu<br>100 | Lys | Glu | Lys | Val | Ser<br>105 | Ala | Leu | Lys | Glu | Lys<br>110 | Val | Ser |
| Ala | Leu | Lys<br>115 | Glu | Lys | Val | Ser | Ala<br>120 | Leu | Lys | Glu | Lys | Val<br>125 | Ser | Ala | Leu |
| Lys | Glu<br>130 | | | | | | | | | | | |

What is claimed is:

1. A composition comprising a compound of Formula I:

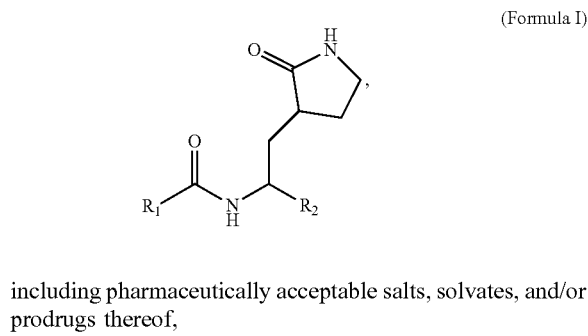

(Formula I)

including pharmaceutically acceptable salts, solvates, and/or prodrugs thereof, wherein R1 is selected from hydrogen,

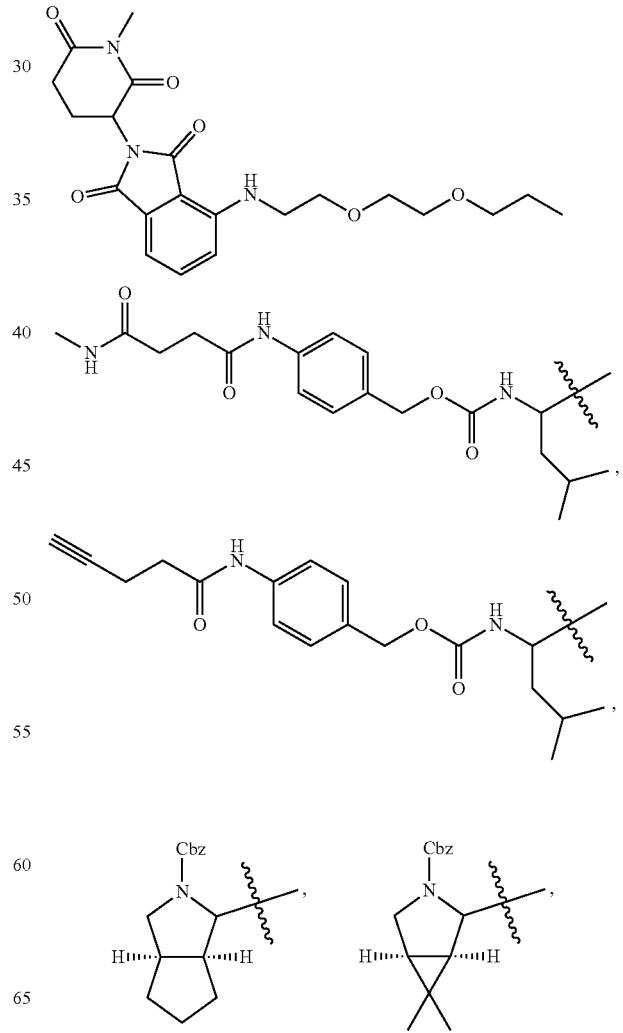

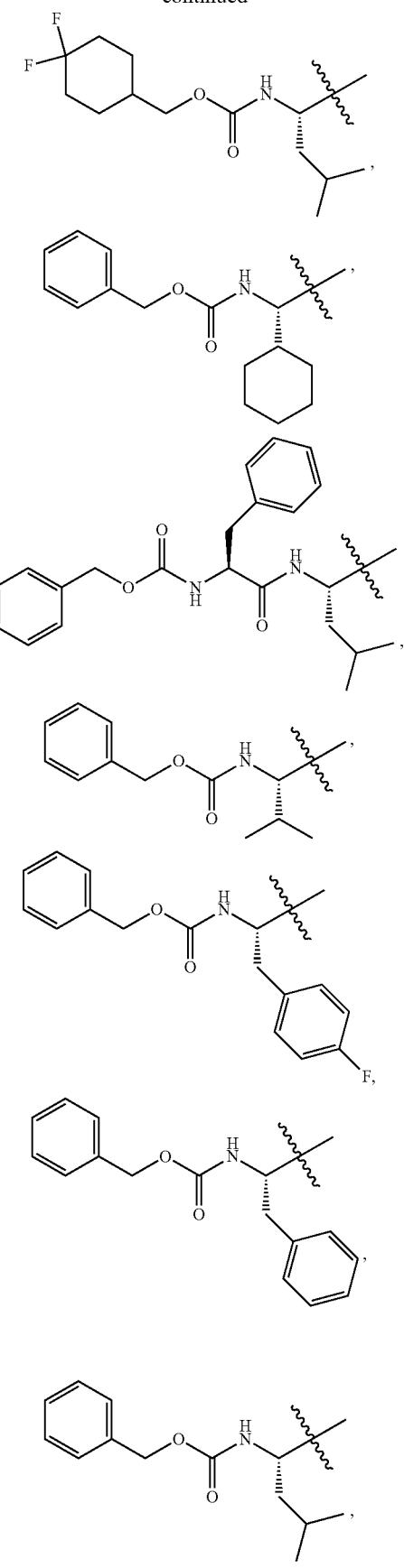
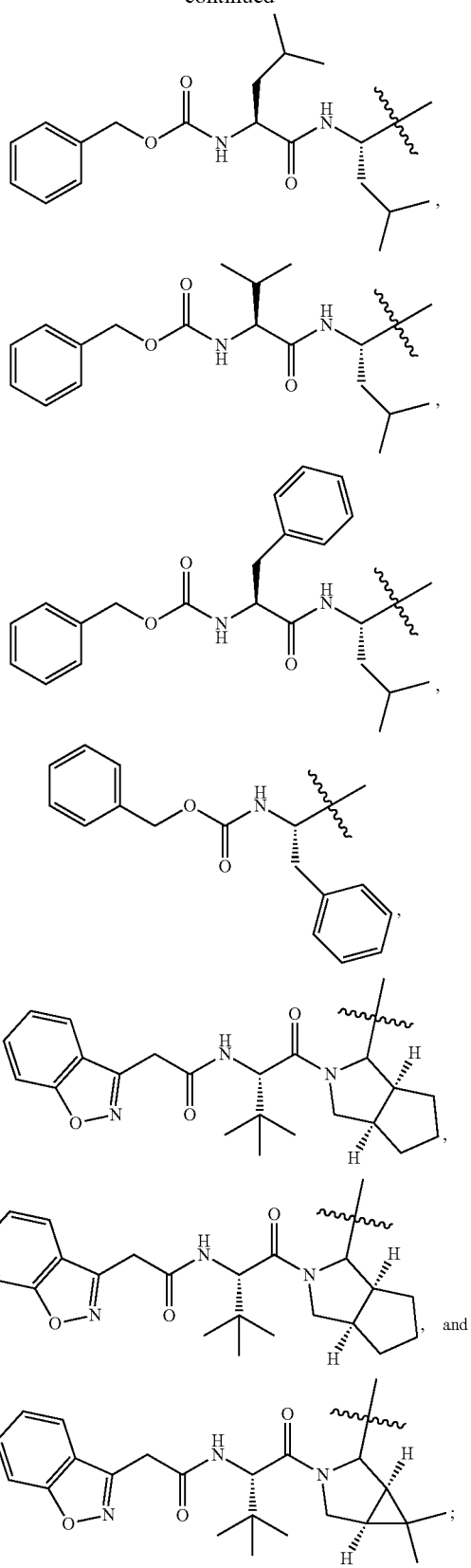
wherein R2 is selected from the group consisting of hydrogen,

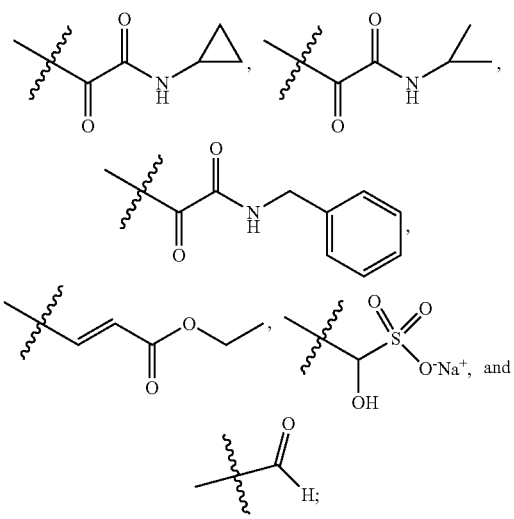
and
wherein if R1 is
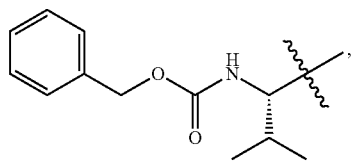 [SMILES: *[C@@H](NC(=O)OCc1ccccc1)C(C)C]
then R2 cannot be
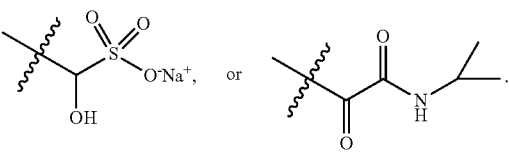
2. The composition of claim 1, wherein said compound is selected from the group consisting of:
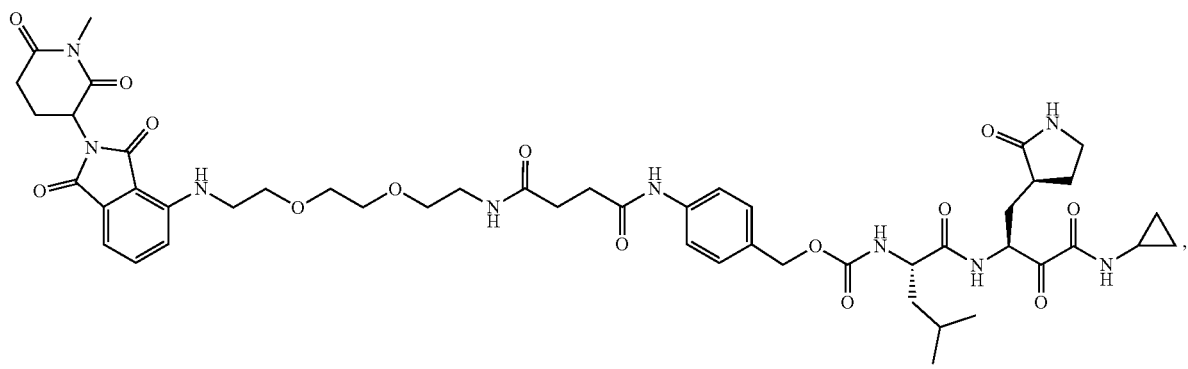
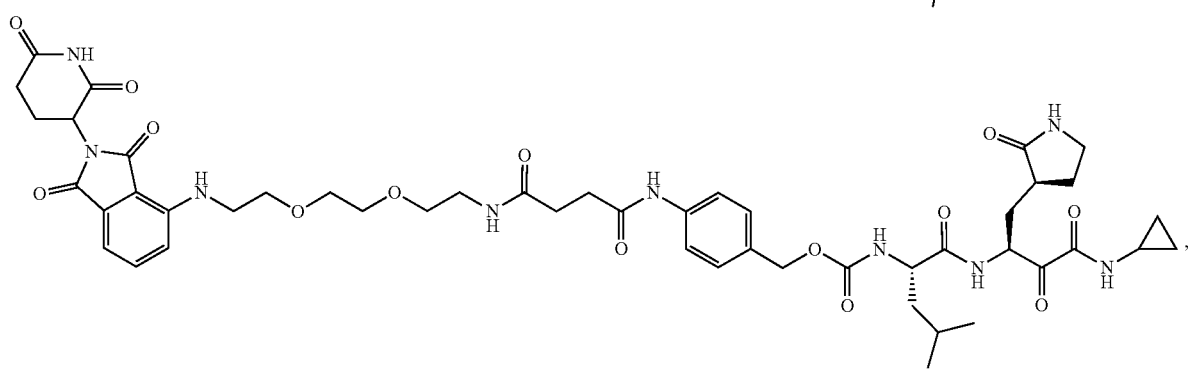
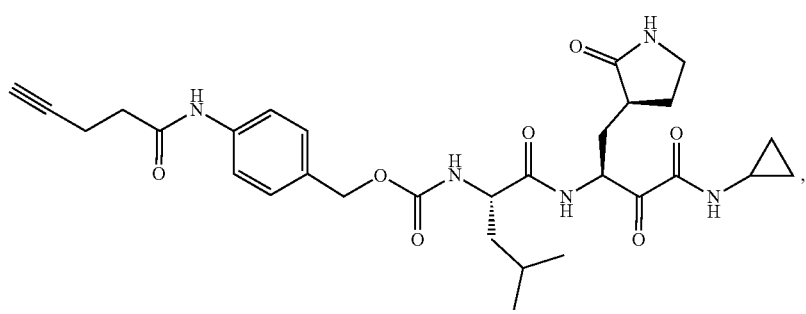

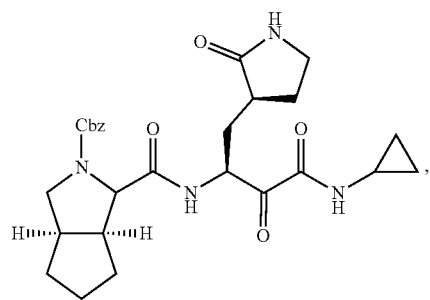
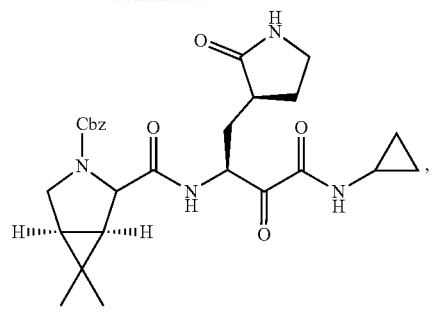
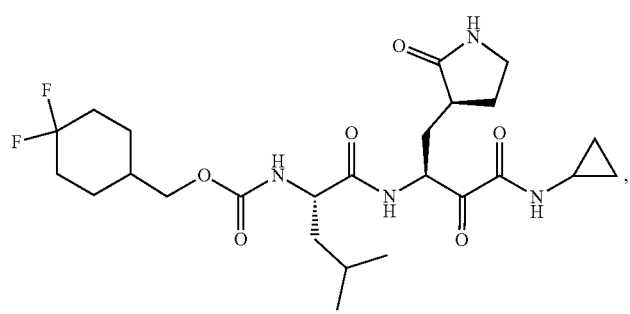
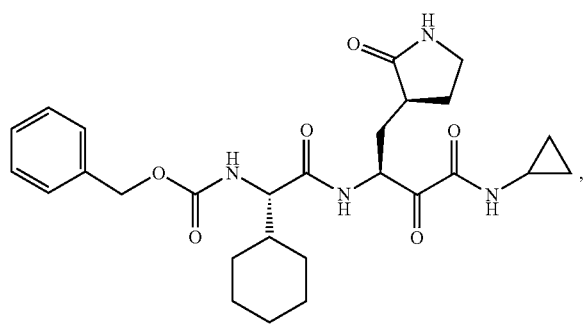
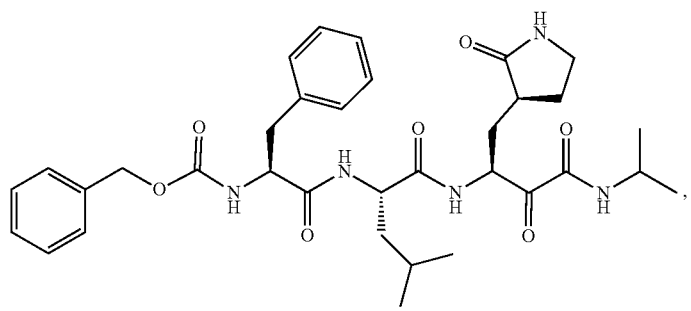
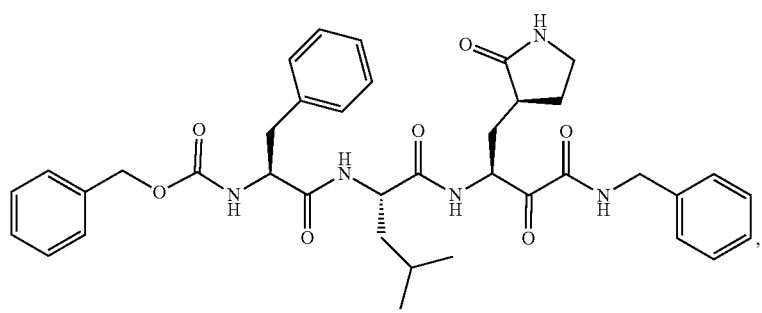

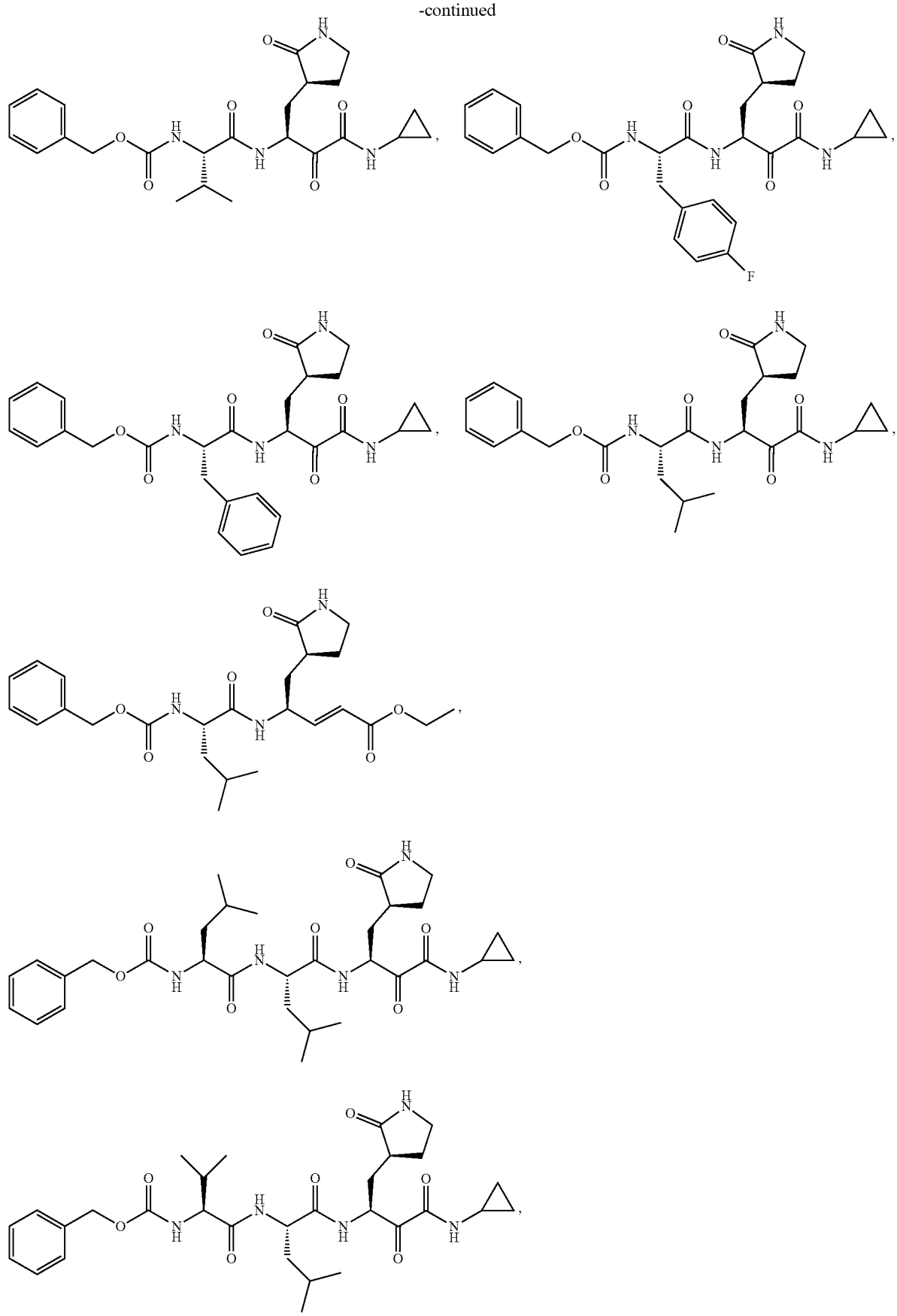

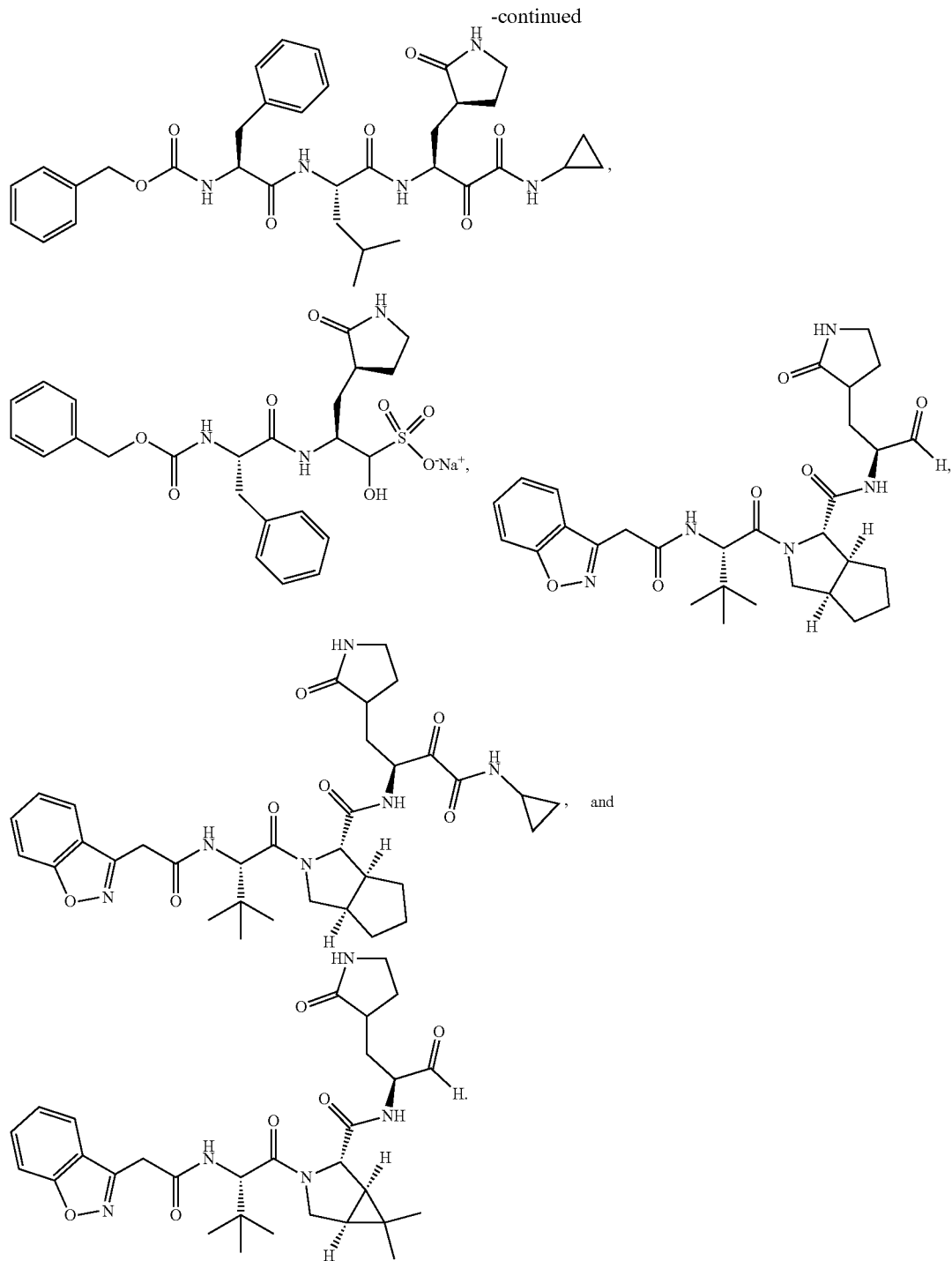

3. The composition of claim 1, wherein composition is a pharmaceutical composition.

4. A method for treating and/or ameliorating a condition related to viral infection in a subject, comprising administering to the subject a therapeutically effective amount of the pharmaceutical composition of claim 3.

5. The method of claim 4, wherein the condition related to viral infection is SARS-CoV-2 infection.

6. The method of claim 4, wherein the subject is a human subject suffering from or at risk of suffering from a condition related to SARS-CoV-2 infection.

7. The method of claim 4, wherein the subject is experiencing symptoms related to the viral infection, wherein the symptoms are one or more of fever, fatigue, dry cough, myalgias, dyspnea, acute respiratory distress syndrome, and pneumonia.

8. The method of claim 7, wherein the administering treats and/or ameliorates the symptoms related to the viral infection.

9. The method of claim 3, wherein the pharmaceutical composition is dispersed in a pharmaceutically acceptable carrier.

10. The method of claim 3, wherein the administering is oral, intravenous, or topical.

11. The method of claim 3, further comprising administering to the subject one or more of hydroxychloroquine, dexamethasone, and remdesivir.

12. The method of claim 4, wherein administration of the pharmaceutical composition results in suppression of $M^{pro}$ protease activity and/or suppression of $PL^{pro}$ protease activity.

13. A composition comprising compound selected from the group consisting of:

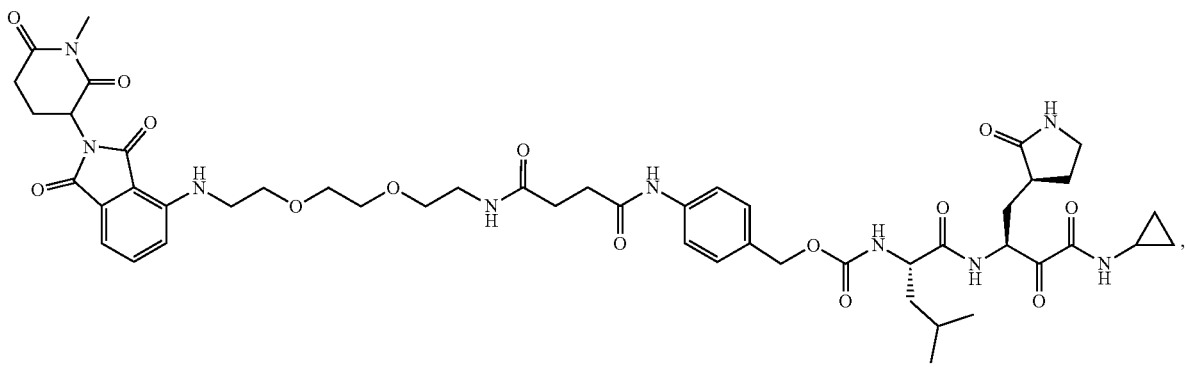

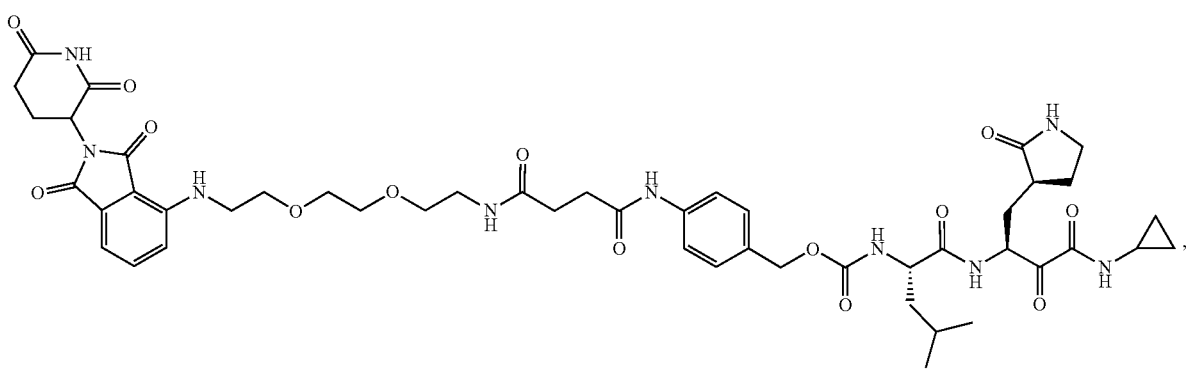

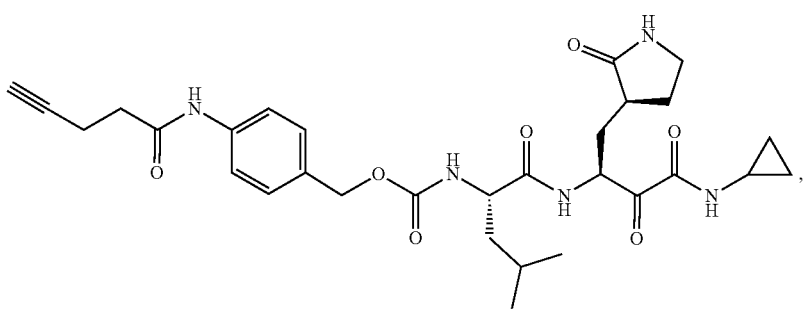

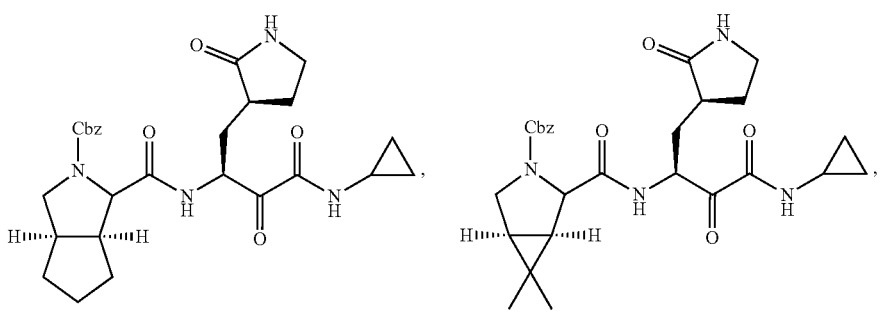

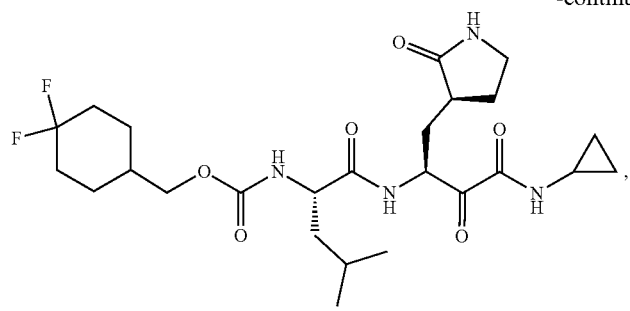
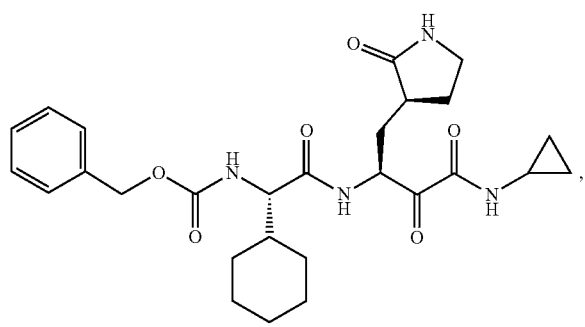
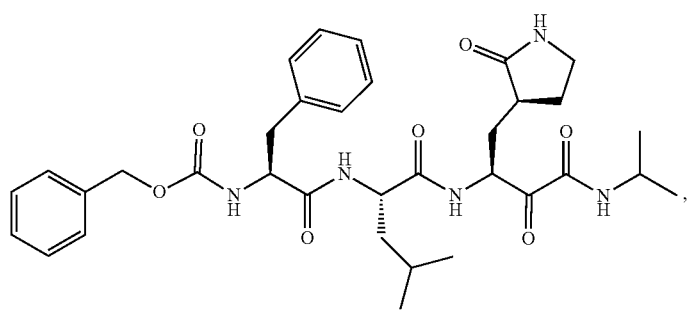
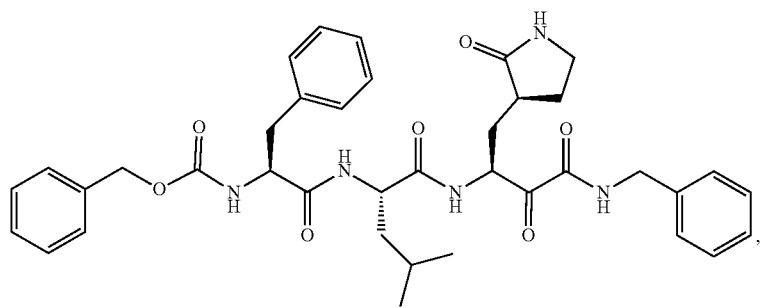
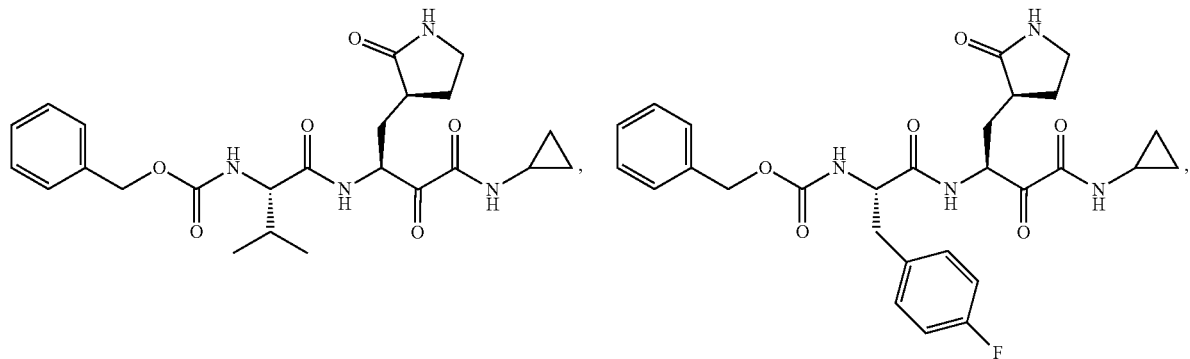

-continued
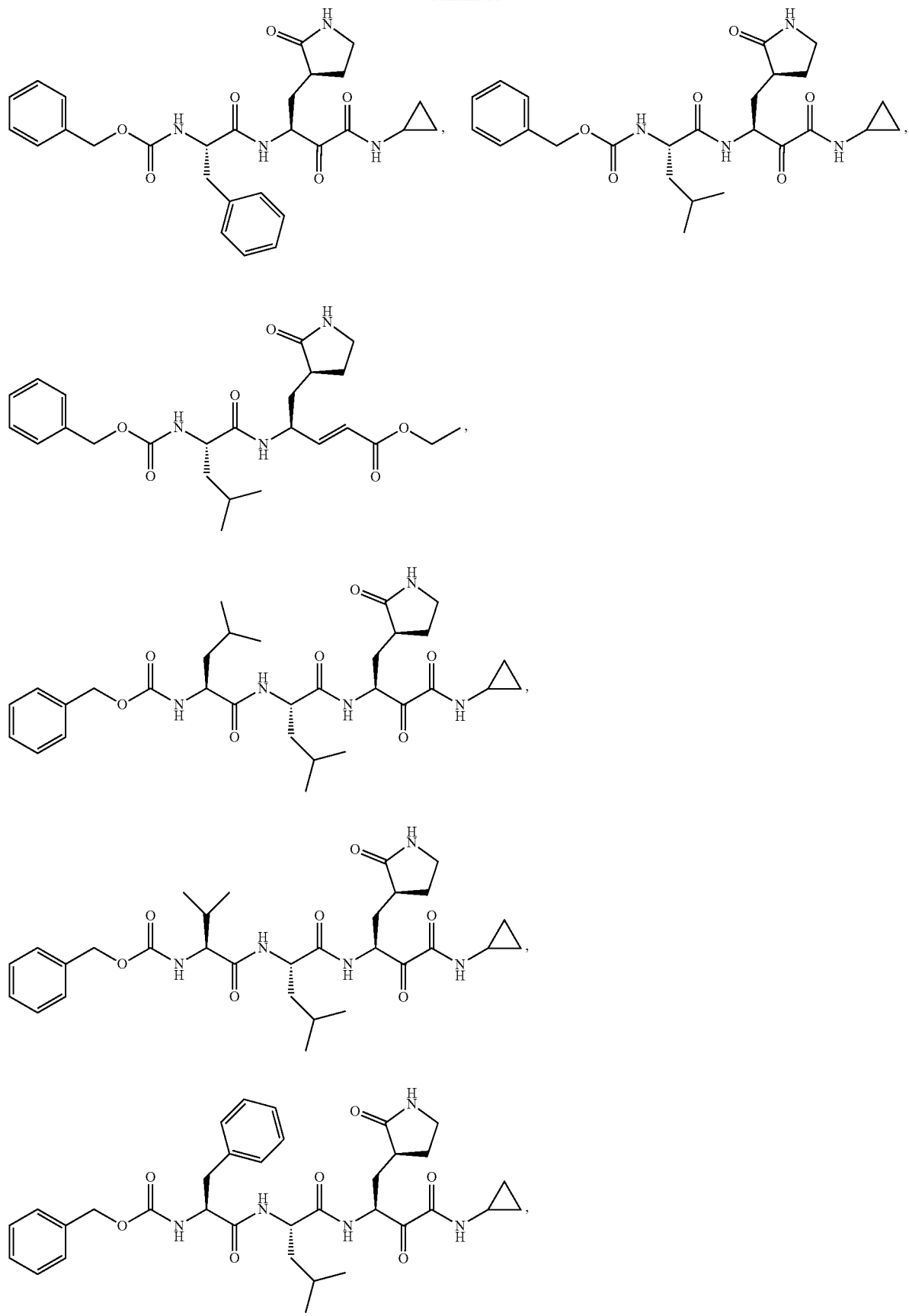

-continued
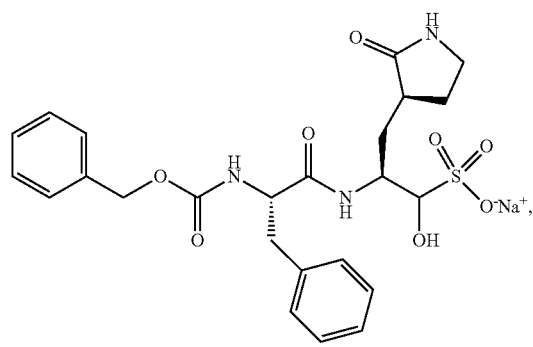
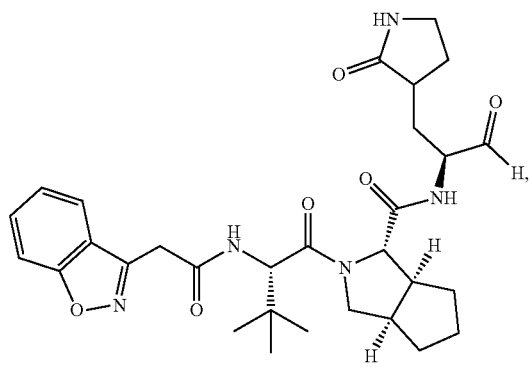
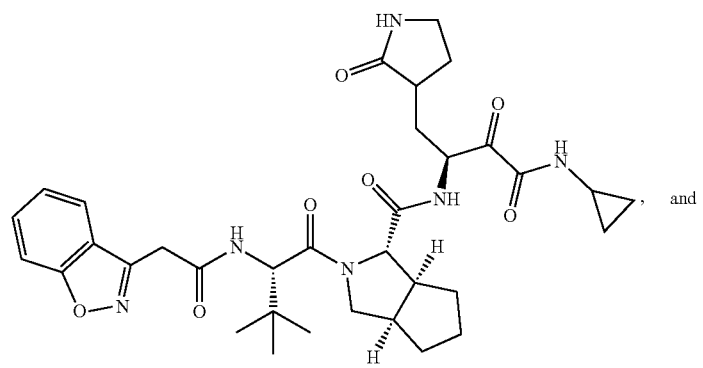
, and
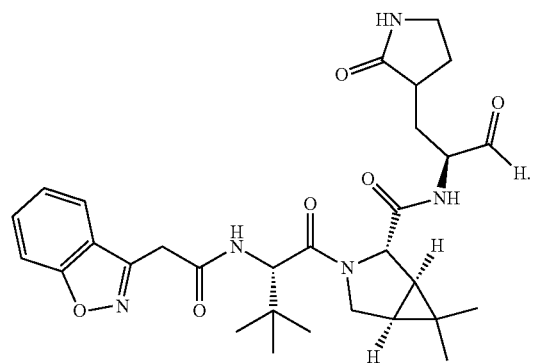
* * * * *